US011197935B2

(12) United States Patent
Kim et al.

(10) Patent No.: US 11,197,935 B2
(45) Date of Patent: Dec. 14, 2021

(54) TALEN TARGETING BLOOD COAGULATION FACTOR VIII INTRON 1 INVERSION GENE AND COMPOSITION FOR TREATING HEMOPHILIA COMPRISING SAME

(71) Applicants: INDUSTRY-ACADEMIC COOPERATION FOUNDATION, YONSEI UNIVERSITY, Seoul (KR); INSTITUTE FOR BASIC SCIENCE, Daejeon (KR)

(72) Inventors: Dong Wook Kim, Seoul (KR); Jin Soo Kim, Seoul (KR); Chul Yong Park, Seoul (KR); Duk Hyoung Kim, Gyeonggi-do (KR); Jung Eun Kim, Seoul (KR); Jiyeon Kweon, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 612 days.

(21) Appl. No.: 15/807,850

(22) Filed: Nov. 9, 2017

(65) Prior Publication Data
US 2018/0055951 A1    Mar. 1, 2018

Related U.S. Application Data

(63) Continuation of application No. 15/541,784, filed as application No. PCT/KR2016/000101 on Jan. 6, 2016.

(30) Foreign Application Priority Data

Jan. 6, 2015  (KR) .................. 10-2015-0001391
Jan. 6, 2015  (KR) .................. 10-2015-0001392

(51) Int. Cl.
| | |
|---|---|
| *A61K 48/00* | (2006.01) |
| *C12N 5/074* | (2010.01) |
| *C12N 9/22* | (2006.01) |
| *C12N 15/11* | (2006.01) |
| *A61K 35/545* | (2015.01) |
| *C07K 14/755* | (2006.01) |
| *C12N 15/113* | (2010.01) |
| *A61K 35/12* | (2015.01) |

(52) U.S. Cl.
CPC ............ *A61K 48/005* (2013.01); *A61K 35/12* (2013.01); *A61K 35/545* (2013.01); *A61K 48/00* (2013.01); *C07K 14/755* (2013.01); *C12N 5/0696* (2013.01); *C12N 9/22* (2013.01); *C12N 15/11* (2013.01); *C12N 15/113* (2013.01); *C12N 2310/20* (2017.05); *C12N 2501/73* (2013.01); *C12N 2506/09* (2013.01)

(58) Field of Classification Search
None
See application file for complete search history.

(56) References Cited

U.S. PATENT DOCUMENTS 10,272,163 B2    4/2019  Laterza et al.

FOREIGN PATENT DOCUMENTS

| WO | WO 2012-051343 | 4/2012 | ............ C07K 14/00 |
| WO | WO 2014-089541 | 6/2014 | ............ H01F 5/04 |
| WO | WO-2014-089541 A2 | 6/2014 | |

OTHER PUBLICATIONS

Office Action from corresponding Japanese Patent Application No. 2017-536342, dated Aug. 28, 2018.
Extended European Search Report from corresponding EP Patent Application No. 16735167.5, dated Sep. 21, 2018.
C.-Y. Park et al., "Targeted inversion and reversion of the blood coagulation factor 8 gene in human iPS cells using TALENs", Proceedings of the National Academy of Sciences, US, (Jun. 9, 2014), vol. 111, No. 25, doi:10.1073/pnas.1323941111, ISSN 0027-8424, pp. 9253-9258.
S. W. Cho et al., "Analysis of off-target effects of CRISPR/Cas-derived RNA-guided endonucleases and nickases", Genome Research, US, (Nov. 19, 2013), vol. 24, No. 1, doi:10.1101/gr.162339.113, ISSN 1088-9051, pp. 132-141.
Chul-Yong Park et al., "Functional Correction of Large Factor VIII Gene Chromosomal Inversions in Hemophilia A Patient-Derived iPSCs Using CRISPR-Cas9", Cell Stem Cell, Amsterdam, NL, (Aug. 1, 2015), vol. 17, No. 2, doi:10.1016/j.stem.2015.07.001, ISSN 1934-5909, pp. 213-220.

(Continued)

*Primary Examiner* — James D Schultz
*Assistant Examiner* — J. Douglas Schultz
(74) *Attorney, Agent, or Firm* — Harness, Dickey & Pierce, P.L.C.

(57) ABSTRACT

The present invention provides a method for inducing an inversion of normal blood coagulation factor VIII (F8) gene, a method for correcting an inversion of blood coagulation factor VIII gene in which the inversion has occurred, and a Hemophilia A patient-derived induced pluripotent stem cell in which the inversion is corrected, constructed using the same. The method of the present invention effectively reproduces the inversion of intron 1 and intron 22 of the F8 gene, which is responsible for the majority of severe hemophilia A, and thereby may be effectively used for studying the development mechanism of hemophilia A and as a research tool for screening therapeutic agents. The inversion-corrected induced pluripotent stem cell constructed according the method of the present invention enables an efficient and fundamental treatment for hemophilia A by restoring a genotype in which mutation has occurred to a wild type-like state, without limitation via normal gene or protein delivery.

11 Claims, 40 Drawing Sheets

Specification includes a Sequence Listing.

(56) References Cited

OTHER PUBLICATIONS

International Search Report from corresponding PCT Application No. PCT/KR2016/000101 dated Jun. 29, 2016 and its English translation.
Park et al., "Targeted inversion and reversion of the blood coagulation factor 8 gene in human iPS cells using TALENs", PNAS, vol. 111, No. 25, pp. 9253-9258, Jun. 24, 2014.
Lee, H.J et al., "Targeted Chromosomal Duplications and Inversions in the Human Genome Using Zinc Finger Nucleases", Genome Research, 2012, vol. 22, pp. 539-548.
Xiao, A. et al., "Chromosomal Deletions and Inversions Mediated by TALENs and CRISPR/Cas in Zebrafish", Nucleic Acids Research, 2013, vol. 41, No. 14, e141, inner pp. 1-11.
Extended European Search Report from corresponding European Patent Application No. 19152493.3, dated Mar. 4, 2019.
Database Geneseq [Online] Jul. 27, 2017 (Jul. 27, 2017), "Human HLA-A gene targeted gRNA, Seq ID 981.", XP002789940, retrieved from EBI accession No. GSN:BDZ41019 Database accession No. BDZ41019.
Bagnall, et al. (2002) "Recurrent inversion breaking intron 1 of the factor VIII gene is a frequent cause of severe hemophilia A.", *Blood*, (Jan. 1, 2002), 99(1):168-174.

FIG. 3F

TALEN target site (Homolog 1)
WT ...caTAAAGTATAATGAAAACTGTtggacacacaagGAGAGACTGGCCAATCTATAgt... (SEQ ID NO: 112)

Breakpoint Junction 1
Clone 1 ...caTAAAGTATAATGAAAACTGTtggacacacaagGAGAGACTGGCCAATCTATAgt... (SEQ ID NO: 112)
Clone 2 ...caTAAAGTATAATGAAAACTGTtggacacacaagGAGAGACTGGCCAATCTATAgt... (SEQ ID NO: 112)
Clone 3 ...caTAAAGTATAATGAAAACTGTtggacacacaagGAGAGACTGGCCAATCTATAgt... (SEQ ID NO: 112)
Clone 4 ...caTAAAGTATAATGAAAACTGTtggacacacaagGAGAGACTGGCCAATCTATAgt... (SEQ ID NO: 112)

TALEN target site (Homolog 2)
WT acTATAGATTGGCCAGTCTCTCttgtgtgtccaACAGTTTCATTATACTTATgt... (SEQ ID NO: 113)

Breakpoint Junction 2
Clone 1 acTATAGATTGGCCAGTCTCTCttgtgtgtccaACAGTTTCATTATACTTAgt... (SEQ ID NO: 113)
Clone 2 acTATAGATTGGCCAGTCTCTCttgtgtgtccaACAGTTTCATTATACTTAgt... (SEQ ID NO: 113)
Clone 3 acTATAGATTGGCCAGTCTCTCttgtgtgtccaACAGTTTCATTATACTTAgt... (SEQ ID NO: 113)
Clone 4 acTATAGATTGGCCAGTCTCTCttgtgtgtccaACAGTTTCATTATACTTAgt... (SEQ ID NO: 113)

FIG. 7B

Inversion
Clone 1 ...ca<u>TAAACTATAATGAAAACTCT</u>tggacacacaag<u>GAGAGACTGGCCAATCTATA</u>gt... (SEQ ID NO: 112)

Reverted            Homolog 1 (Breakpoint)
Clone 1 ...ca<u>TAAACTATAATGAAAACTCT</u>tggac--acaag<u>GAGAGACTGGCCAATCTATA</u>gt... (SEQ ID NO: 114)
Clone 2 ...ca<u>TAAACTATAATGAAAACTCT</u>tggac--acaag<u>GAGAGACTGGCCAATCTATA</u>gt... (SEQ ID NO: 114)
Clone 3 ...ca<u>TAAACTATAATGAAAACTCT</u>tggacacacaag<u>GAGAGACTGGCCAATCTATA</u>gt... (SEQ ID NO: 112)
Clone 4 ...ca<u>TAAACTATAATGAAAACTCT</u>tggacacacaag<u>GAGAGACTGGCCAATCTATA</u>gt... (SEQ ID NO: 112)

Inversion        TALEN target site (Junction 2)
Clone 1 ...ac<u>TATAGATTGGCCAGTCTCTC</u>cttgtgtgtcca<u>AGAGTTTCATTATAGTTTA</u>gt... (SEQ ID NO: 113)

Reverted           Homolog 2 (Breakpoint)
Clone 1 ...ac<u>TATAGATTGGCCAGTCTCTC</u>cttgt--gtcca<u>AGAGTTTCATTATAGTTTA</u>gt... (SEQ ID NO: 115)
Clone 2 ...ac<u>TATAGATTGGCCAGTCTCTC</u>cttgt--gtcca<u>AGAGTTTCATTATAGTTTA</u>gt... (SEQ ID NO: 115)
Clone 3 ...ac<u>TATAGATTGGCCAGTCTCTC</u>cttgtgtgtcca<u>AGAGTTTCATTATAGTTTA</u>gt... (SEQ ID NO: 113)
Clone 4 ...ac<u>TATAGATTGGCCAGTCTCTC</u>cttgtgtgtcca<u>AGAGTTTCATTATAGTTTA</u>gt... (SEQ ID NO: 113)

FIG. 8B

| Nucleases | Frequency (%) | | |
|---|---|---|---|
| | Estimate | Upper limits | Lower limits |
| ZFN-224 | 5 | 7 | 3 |
| Z10 | 0.25 | 0.4 | 0.2 |
| TALEN01 | 1.9 | 2.8 | 1.2 |

FIG. 11B

SEQUENCE LISTING

<160> NUMBER OF SEQ ID NOS: 121

<210> SEQ ID NO 1
<211> LENGTH: 20
<212> TYPE: DNA
<213> ORGANISM: homo sapiens

<400> SEQUENCE: 1
cccgtataac tcttaaacac					20

<210> SEQ ID NO 2
<211> LENGTH: 20
<212> TYPE: DNA
<213> ORGANISM: homo sapiens

<400> SEQUENCE: 2
tggtaagagt accggtggga					20

<210> SEQ ID NO 3
<211> LENGTH: 20
<212> TYPE: DNA
<213> ORGANISM: homo sapiens

<400> SEQUENCE: 3
ggtccccggg gttgtgcccc					20

<210> SEQ ID NO 4
<211> LENGTH: 1041
<212> TYPE: DNA
<213> ORGANISM: homo sapiens

<400> SEQUENCE: 4
cagttgtcag tatgtgaaca atgttggaaa catgttattt tgtctgattt cctttgggag			60 aattcattgc cagctataaa tctgtggaaa cgctgccaca caatcttagc acacaagatt			120 ggcagaaaat cgcttagaaa cactgaaaac atgtgacaaa gtgctttccg tgaaaagggt			180 ggatgcgaag cagtaaggac cccttcatg aagcacgcgg tcaccctcca gccaccagaa			240 ccagaggaac gctgtggtaa ctgagggaaa acgcatctag gcacacgtca cggtggcacc			300 ttccagcagg tccccggggt tgtgccctg gagctctgac aaagagtgtg gcccggaaat			360 gtgatgtttg gactgcaagt tttggtgaga ataacaatg catcaggttg cagacaaagc			420 agaccctgct ctgtgcgttt atgggagccg cgcccaacag gaaccacagg gaatgatcga			480 aaggagaggg acggacacaa acagacacac cagagagagg ttctcaggag gaggctctgt			540 ggcctccaga ccacgtcaaa gccaaggcag aaaggatgaa ctgaggaaag gaggaaaatt			600 tccccttaag gaaggtaaaa tccagaaggg atccctaaaa tggtgagcag tttaaaccta			660 gcagttttgc attaattcac ataagtata atgaaaactg ttggacacac aaggagagac			720 tggccaatct atagtcacag aggaagacct tcacacccct tcacaggatc tcgcagcaga			780

```
ttggctgaaa agtctccttg aaactgcaga cctctctcaa ggagacccac tgagttgggc    840
aaaggtgggg ccgacttaat tcttgcctcc ctgctctccc acgtagccct gcatttcact    900
ccattccagg gtttctggga cacccgagaa agcacgtagt ccagggagca cgtctgccaa    960
ctgaaggcct tgacaaatga ctttctgtac tggctgaggg ccagggccca gcgtactgat   1020
aaggaagctc ttccagaaaa a                                              1041

<210> SEQ ID NO 5
<211> LENGTH: 20
<212> TYPE: DNA
<213> ORGANISM: Artificial Sequence
<220> FEATURE:
<223> OTHER INFORMATION: homolog 1-1F primer

<400> SEQUENCE: 5 aaatcacccca aggaagcaca                                                 20

<210> SEQ ID NO 6
<211> LENGTH: 24
<212> TYPE: DNA
<213> ORGANISM: Artificial Sequence
<220> FEATURE:
<223> OTHER INFORMATION: homolog 1-1R primer

<400> SEQUENCE: 6
tggcattaac gtattacttg gaga                                             24

<210> SEQ ID NO 7
<211> LENGTH: 21
<212> TYPE: DNA
<213> ORGANISM: Artificial Sequence
<220> FEATURE:
<223> OTHER INFORMATION: homolog 2-2F primer

<400> SEQUENCE: 7
ggcagggatc ttgttggtaa a                                                21

<210> SEQ ID NO 8
<211> LENGTH: 22
<212> TYPE: DNA
<213> ORGANISM: Artificial Sequence
<220> FEATURE:
<223> OTHER INFORMATION: homolog 2-2R primer

<400> SEQUENCE: 8
tgctgagcta gcaggtttaa tg                                               22

<210> SEQ ID NO 9
<211> LENGTH: 20
<212> TYPE: DNA
<213> ORGANISM: Artificial Sequence
<220> FEATURE:
<223> OTHER INFORMATION: forward primer 22-F1

<400> SEQUENCE: 9
tggggctgtg taaatttgct                                                  20

<210> SEQ ID NO 10
<211> LENGTH: 23
<212> TYPE: DNA
<213> ORGANISM: Artificial Sequence
<220> FEATURE:
<223> OTHER INFORMATION: reverse primer 22-R2

<400> SEQUENCE: 10
```
caaacgtagc attacctgat tgt 23

<210> SEQ ID NO 11
<211> LENGTH: 23
<212> TYPE: DNA
<213> ORGANISM: Artificial Sequence
<220> FEATURE:
<223> OTHER INFORMATION: forward primer 22-F2

<400> SEQUENCE: 11
acaaccagag cagaaatcaa tga 23

<210> SEQ ID NO 12
<211> LENGTH: 20
<212> TYPE: DNA
<213> ORGANISM: Artificial Sequence
<220> FEATURE:
<223> OTHER INFORMATION: reverse primer 22-R2

<400> SEQUENCE: 12
tttcaccaca tccacgccaa 20

<210> SEQ ID NO 13
<211> LENGTH: 23
<212> TYPE: DNA
<213> ORGANISM: Artificial Sequence
<220> FEATURE:
<223> OTHER INFORMATION: Forward primer GAPDH-F

<400> SEQUENCE: 13
cccctcaagg gcatcctggg cta 23

<210> SEQ ID NO 14
<211> LENGTH: 24
<212> TYPE: DNA
<213> ORGANISM: Artificial Sequence
<220> FEATURE:
<223> OTHER INFORMATION: Reverse primer GAPDH-R

<400> SEQUENCE: 14
gaggtccacc accctgttgc tgta 24

<210> SEQ ID NO 15
<211> LENGTH: 20
<212> TYPE: DNA
<213> ORGANISM: Artificial Sequence
<220> FEATURE:
<223> OTHER INFORMATION: Forward primer OCT4-F

<400> SEQUENCE: 15
cctcacttca ctgcactgta 20

<210> SEQ ID NO 16
<211> LENGTH: 20
<212> TYPE: DNA
<213> ORGANISM: Artificial Sequence
<220> FEATURE:
<223> OTHER INFORMATION: Reverse primer OCT4-R

<400> SEQUENCE: 16
caggttttct ttccctagct 20

<210> SEQ ID NO 17
<211> LENGTH: 25
<212> TYPE: DNA

```
<213> ORGANISM: Artificial Sequence
<220> FEATURE:
<223> OTHER INFORMATION: Forward primer LIN28-F

<400> SEQUENCE: 17
agccatatgg tagcctcatg tccgc                                    25

<210> SEQ ID NO 18
<211> LENGTH: 30
<212> TYPE: DNA
<213> ORGANISM: Artificial Sequence
<220> FEATURE:
<223> OTHER INFORMATION: Reverse primer LIN28-R

<400> SEQUENCE: 18
tcaattctgt gcctccggga gcagggtagg                               30

<210> SEQ ID NO 19
<211> LENGTH: 24
<212> TYPE: DNA
<213> ORGANISM: Artificial Sequence
<220> FEATURE:
<223> OTHER INFORMATION: Forward primer SOX2-F

<400> SEQUENCE: 19
ttcacatgtc ccagcactac caga                                     24

<210> SEQ ID NO 20
<211> LENGTH: 26
<212> TYPE: DNA
<213> ORGANISM: Artificial Sequence
<220> FEATURE:
<223> OTHER INFORMATION: Reverse primer SOX2-R

<400> SEQUENCE: 20
tcacatgtgt gagaggggca gtgtgc                                   26

<210> SEQ ID NO 21
<211> LENGTH: 20
<212> TYPE: DNA
<213> ORGANISM: Artificial Sequence
<220> FEATURE:
<223> OTHER INFORMATION: forward primer NANOG-F

<400> SEQUENCE: 21
tgaacctcag ctacaaacag                                          20

<210> SEQ ID NO 22
<211> LENGTH: 20
<212> TYPE: DNA
<213> ORGANISM: Artificial Sequence
<220> FEATURE:
<223> OTHER INFORMATION: Reverse primer NANOG-R

<400> SEQUENCE: 22
tggtggtagg aagagtaaag                                          20

<210> SEQ ID NO 23
<211> LENGTH: 22
<212> TYPE: DNA
<213> ORGANISM: Artificial Sequence
<220> FEATURE:
<223> OTHER INFORMATION: Forward primer F8-exon1-F

<400> SEQUENCE: 23
ctgctttagt gccaccagaa ga                                       22
```

```
<210> SEQ ID NO 24
<211> LENGTH: 20
<212> TYPE: DNA
<213> ORGANISM: Artificial Sequence
<220> FEATURE:
<223> OTHER INFORMATION: Reverse primer F8-exon3-R

<400> SEQUENCE: 24
gactgacagg atgggaagcc                                                 20

<210> SEQ ID NO 25
<211> LENGTH: 22
<212> TYPE: DNA
<213> ORGANISM: Artificial Sequence
<220> FEATURE:
<223> OTHER INFORMATION: Forward primer F8-exon21-F

<400> SEQUENCE: 25
ccggatcaat caatgcctgg ag                                              22

<210> SEQ ID NO 26
<211> LENGTH: 22
<212> TYPE: DNA
<213> ORGANISM: Artificial Sequence
<220> FEATURE:
<223> OTHER INFORMATION: Reverse primer F8-exon23-R

<400> SEQUENCE: 26
atgagttggg tgcaaacgga tg                                              22

<210> SEQ ID NO 27
<211> LENGTH: 23
<212> TYPE: DNA
<213> ORGANISM: Artificial Sequence
<220> FEATURE:
<223> OTHER INFORMATION: Forward primer Brachyury-F

<400> SEQUENCE: 27
atcacaaaga gatgatggag gaa                                             23

<210> SEQ ID NO 28
<211> LENGTH: 23
<212> TYPE: DNA
<213> ORGANISM: Artificial Sequence
<220> FEATURE:
<223> OTHER INFORMATION: Forward primer Brachyury-R

<400> SEQUENCE: 28
ggtgagttgt cagaataggt tgg                                             23

<210> SEQ ID NO 29
<211> LENGTH: 650
<212> TYPE: PRT
<213> ORGANISM: Artificial Sequence
<220> FEATURE:
<223> OTHER INFORMATION: left TAL effector

<400> SEQUENCE: 29

Leu Asn Leu Thr Pro Ala Gln Val Val Ala Ile Ala Ser Asn Ile Gly
 1               5                  10                  15

Gly Lys Gln Ala Leu Glu Thr Val Gln Arg Leu Leu Pro Val Leu Cys
             20                  25                  30

Gln Asp His Gly Leu Thr Pro Ala Gln Val Val Ala Ile Ala Ser Asn
         35                  40                  45
```

```
Gly Gly Gly Lys Gln Ala Leu Glu Thr Val Gln Arg Leu Leu Pro Val
         50                  55                  60

Leu Cys Gln Asp His Gly Leu Thr Pro Asp Gln Val Val Ala Ile Ala
 65                  70                  75                  80

Ser Asn Ile Gly Gly Lys Gln Ala Leu Glu Thr Val Gln Arg Leu Leu
                 85                  90                  95

Pro Val Leu Cys Gln Asp His Gly Leu Thr Pro Ala Gln Val Val Ala
            100                 105                 110

Ile Ala Ser Asn Asn Gly Gly Lys Gln Ala Leu Glu Thr Val Gln Arg
            115                 120                 125

Leu Leu Pro Val Leu Cys Gln Asp His Gly Leu Thr Pro Ala Gln Val
        130                 135                 140

Val Ala Ile Ala Ser Asn Ile Gly Gly Lys Gln Ala Leu Glu Thr Val
145                 150                 155                 160

Gln Arg Leu Leu Pro Val Leu Cys Gln Ala His Gly Leu Thr Pro Glu
                165                 170                 175

Gln Val Val Ala Ile Ala Ser Asn Gly Gly Gly Lys Gln Ala Leu Glu
            180                 185                 190

Thr Val Gln Arg Leu Leu Pro Val Leu Cys Gln Ala His Gly Leu Thr
            195                 200                 205

Pro Glu Gln Val Val Ala Ile Ala Ser Asn Gly Gly Gly Lys Gln Ala
        210                 215                 220

Leu Glu Thr Val Gln Arg Leu Leu Pro Val Leu Cys Gln Ala His Gly
225                 230                 235                 240

Leu Thr Pro Ala Gln Val Val Ala Ile Ala Ser Asn Asn Gly Gly Lys
                245                 250                 255

Gln Ala Leu Glu Thr Val Gln Arg Leu Leu Pro Val Leu Cys Gln Asp
            260                 265                 270

His Gly Leu Thr Pro Asp Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Ala His Gly Leu Thr Pro Ala Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Asp His Gly Leu Thr Pro Asp Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Ala His Gly Leu Thr Pro Asp Gln Val Val Ala
    370                 375                 380

Ile Ala Ser Asn Ile Gly Gly Lys Gln Ala Leu Glu Thr Val Gln Arg
385                 390                 395                 400

Leu Leu Pro Val Leu Cys Gln Ala His Gly Leu Thr Pro Ala Gln Val
                405                 410                 415

Val Ala Ile Ala Ser Asn Asn Gly Gly Lys Gln Ala Leu Glu Thr Val
            420                 425                 430

Gln Arg Leu Leu Pro Val Leu Cys Gln Asp His Gly Leu Thr Pro Ala
        435                 440                 445

Gln Val Val Ala Ile Ala Ser Asn Gly Gly Gly Lys Gln Ala Leu Glu
    450                 455                 460
```

```
Thr Val Gln Arg Leu Leu Pro Val Leu Cys Gln Ala His Gly Leu Thr
465                 470                 475                 480

Pro Asp Gln Val Val Ala Ile Ala Ser His Asp Gly Lys Gln Ala
            485                 490                 495

Leu Glu Thr Val Gln Arg Leu Leu Pro Val Leu Cys Gln Asp His Gly
        500                 505                 510

Leu Thr Pro Glu Gln Val Val Ala Ile Ala Ser Asn Gly Gly Lys
        515                 520                 525

Gln Ala Leu Glu Thr Val Gln Arg Leu Leu Pro Val Leu Cys Gln Ala
        530                 535                 540

His Gly Leu Thr Pro Asp Gln Val Val Ala Ile Ala Ser His Asp Gly
545                 550                 555                 560

Gly Lys Gln Ala Leu Glu Thr Val Gln Arg Leu Leu Pro Val Leu Cys
            565                 570                 575

Gln Asp His Gly Leu Thr Pro Asp Gln Val Val Ala Ile Ala Ser Asn
            580                 585                 590

Gly Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
        610                 615                 620

Ser His Asp Gly Gly Lys Gln Ala Leu Glu Ser Ile Val Ala Gln Leu
625                 630                 635                 640

Ser Arg Pro Asp Pro Ala Leu Ala Ala Leu
                645                 650

<210> SEQ ID NO 30
<211> LENGTH: 648
<212> TYPE: PRT
<213> ORGANISM: Artificial Sequence
<220> FEATURE:
<223> OTHER INFORMATION: right TAL effector

<400> SEQUENCE: 30

Leu Asn Leu Thr Pro Asp Gln Val Val Ala Ile Ala Ser Asn Ile Gly
1               5                   10                  15

Gly Lys Gln Ala Leu Glu Thr Val Gln Arg Leu Leu Pro Val Leu Cys
            20                  25                  30

Gln Ala His Gly Leu Thr Pro Ala Gln Val Val Ala Ile Ala Ser Asn
        35                  40                  45

Ile Gly Gly Lys Gln Ala Leu Glu Thr Val Gln Arg Leu Leu Pro Val
    50                  55                  60

Leu Cys Gln Asp His Gly Leu Thr Pro Ala Gln Val Val Ala Ile Ala
65                  70                  75                  80

Ser Asn Ile Gly Gly Lys Gln Ala Leu Glu Thr Val Gln Arg Leu Leu
                85                  90                  95

Pro Val Leu Cys Gln Ala His Gly Leu Thr Pro Asp Gln Val Val Ala
            100                 105                 110

Ile Ala Ser Asn Asn Gly Gly Lys Gln Ala Leu Glu Thr Val Gln Arg
        115                 120                 125

Leu Leu Pro Val Leu Cys Gln Ala His Gly Leu Thr Pro Ala Gln Val
130                 135                 140

Val Ala Ile Ala Ser Asn Gly Gly Gly Lys Gln Ala Leu Glu Thr Val
145                 150                 155                 160

Gln Arg Leu Leu Pro Val Leu Cys Gln Asp His Gly Leu Thr Pro Ala
                165                 170                 175
```

```
Gln Val Val Ala Ile Ala Ser Asn Ile Gly Gly Lys Gln Ala Leu Glu
                180                 185                 190

Thr Val Gln Arg Leu Leu Pro Val Leu Cys Gln Ala His Gly Leu Thr
            195                 200                 205

Pro Glu Gln Val Val Ala Ile Ala Ser Asn Gly Gly Gly Lys Gln Ala
        210                 215                 220

Leu Glu Thr Val Gln Arg Leu Leu Pro Val Leu Cys Gln Ala His Gly
225                 230                 235                 240

Leu Thr Pro Ala Gln Val Val Ala Ile Ala Ser Asn Ile Gly Gly Lys
                245                 250                 255

Gln Ala Leu Glu Thr Val Gln Arg Leu Leu Pro Val Leu Cys Gln Asp
            260                 265                 270

His Gly Leu Thr Pro Ala Gln Val Val Ala Ile Ala Ser Asn Ile Gly
        275                 280                 285

Gly Lys Gln Ala Leu Glu Thr Val Gln Arg Leu Leu Pro Val Leu Cys
290                 295                 300

Gln Ala His Gly Leu Thr Pro Ala Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Ala His Gly Leu Thr Pro Ala Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Asp His Gly Leu Thr Pro Ala Gln Val Val Ala
370                 375                 380

Ile Ala Ser Asn Ile Gly Gly Lys Gln Ala Leu Glu Thr Val Gln Arg
385                 390                 395                 400

Leu Leu Pro Val Leu Cys Gln Asp His Gly Leu Thr Pro Asp Gln Val
                405                 410                 415

Val Ala Ile Ala Ser Asn Ile Gly Gly Lys Gln Ala Leu Glu Thr Val
            420                 425                 430

Gln Arg Leu Leu Pro Val Leu Cys Gln Ala His Gly Leu Thr Pro Ala
        435                 440                 445

Gln Val Val Ala Ile Ala Ser Asn Ile Gly Gly Lys Gln Ala Leu Glu
450                 455                 460

Thr Val Gln Arg Leu Leu Pro Val Leu Cys Gln Asp His Gly Leu Thr
465                 470                 475                 480

Pro Ala Gln Val Val Ala Ile Ala Ser Asn Ile Gly Gly Lys Gln Ala
                485                 490                 495

Leu Glu Thr Val Gln Arg Leu Leu Pro Val Leu Cys Gln Ala His Gly
            500                 505                 510

Leu Thr Pro Ala Gln Val Val Ala Ile Ala Ser His Asp Gly Gly Lys
        515                 520                 525

Gln Ala Leu Glu Thr Val Gln Arg Leu Leu Pro Val Leu Cys Gln Ala
530                 535                 540

His Gly Leu Thr Pro Ala Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Asp His Gly Leu Thr Pro Asp Gln Val Val Ala Ile Ala Ser Asn
            580                 585                 590

Asn Gly Gly Lys Gln Ala Leu Glu Thr Val Gln Arg Leu Leu Pro Val
```

```
        595                 600                 605
Leu Cys Gln Asp His Gly Leu Thr Pro Glu Gln Val Val Ala Ile Ala
        610                 615                 620

Ser Gly Gly Lys Gln Ala Leu Glu Ser Ile Val Ala Gln Leu Ser Arg
625                 630                 635                 640

Pro Asp Pro Ala Leu Ala Ala Leu
            645

<210> SEQ ID NO 31
<211> LENGTH: 1041
<212> TYPE: DNA
<213> ORGANISM: homo sapiens

<400> SEQUENCE: 31
cagttgtcag tatgtgaaca atgttggaaa catgttattt tgtctgattt cctttgggag      60
aattcattgc cagctataaa tctgtggaaa cgctgccaca caatcttagc acacaagatt     120
ggcagaaaat cgcttagaaa cactgaaaac atgtgacaaa gtgctttccg tgaaaagggt     180
ggatgcgaag cagtaaggac ccccttcatg aagcacgcgg tcaccctcca gccaccagaa     240
ccagaggaac gctgtggtaa ctgagggaaa acgcatctag cacacgtca cggtggcacc      300 ttccagcagg tccccggggt tgtgcccctg gagctctgac aaagagtgtg gcccggaaat     360
gtgatgtttg gactgcaagt tttggtgaga ataacaatg catcaggttg cagacaaagc      420
agaccctgct ctgtgcgttt atgggagccg cgcccaacag gaaccacagg gaatgatcga     480
aaggagaggg acggacacaa acagacacac cagagagagg ttctcaggag gaggctctgt     540
ggcctccaga ccacgtcaaa gccaaggcag aaaggatgaa ctgaggaaag gaggaaaatt     600
tccccttaag gaaggtaaaa tccagaaggg atccctaaaa tggtgagcag tttaaaccta     660
gcagttttgc attaattcac ataaagtata atgaaaactg ttggacacac aaggagagac     720
tggccaatct atagtcacag aggaagacct tcacacccct tcacaggatc tcgcagcaga     780
ttggctgaaa agtctccttg aaactgcaga cctctctcaa ggagacccac tgagttgggc     840
aaaggtgggg ccgacttaat tcttgcctcc ctgctctccc acgtagccct gcatttcact     900
ccattccagg gtttctggga cacccgagaa agcacgtagt ccaggagca cgtctgccaa      960 ctgaaggcct tgacaaatga cttctctgtac tggctgaggg ccagggccca gcgtactgat    1020
aaggaagctc ttccagaaaa a                                               1041

<210> SEQ ID NO 32
<211> LENGTH: 19
<212> TYPE: DNA
<213> ORGANISM: Artificial Sequence
<220> FEATURE:
<223> OTHER INFORMATION: Sox2-F qPCR primer

<400> SEQUENCE: 32
cccagcagac ttcacatgt                                                   19

<210> SEQ ID NO 33
<211> LENGTH: 20
<212> TYPE: DNA
<213> ORGANISM: Artificial Sequence
<220> FEATURE:
<223> OTHER INFORMATION: Sox2-R qPCR primer

<400> SEQUENCE: 33
cctcccattt ccctcgtttt                                                  20
```

```
<210> SEQ ID NO 34
<211> LENGTH: 18
<212> TYPE: DNA
<213> ORGANISM: Artificial Sequence
<220> FEATURE:
<223> OTHER INFORMATION: Lin28-F qPCR primer

<400> SEQUENCE: 34
agccaagcca ctacattc                                                 18

<210> SEQ ID NO 35
<211> LENGTH: 18
<212> TYPE: DNA
<213> ORGANISM: Artificial Sequence
<220> FEATURE:
<223> OTHER INFORMATION: Lin28-R qPCR primer

<400> SEQUENCE: 35
agatacgtca ttcgcaca                                                 18

<210> SEQ ID NO 36
<211> LENGTH: 20
<212> TYPE: DNA
<213> ORGANISM: Artificial Sequence
<220> FEATURE:
<223> OTHER INFORMATION: FOXA2-F RT-PCR primer

<400> SEQUENCE: 36
ctacgccaac atgaactcca                                               20

<210> SEQ ID NO 37
<211> LENGTH: 20
<212> TYPE: DNA
<213> ORGANISM: Artificial Sequence
<220> FEATURE:
<223> OTHER INFORMATION: FOXA2-R RT-PCR primer

<400> SEQUENCE: 37
aaggggaaga ggtccatgat                                               20

<210> SEQ ID NO 38
<211> LENGTH: 20
<212> TYPE: DNA
<213> ORGANISM: Artificial Sequence
<220> FEATURE:
<223> OTHER INFORMATION: Sox17-F RT-PCR primer

<400> SEQUENCE: 38
agcgcccttc acgtgtacta                                               20

<210> SEQ ID NO 39
<211> LENGTH: 20
<212> TYPE: DNA
<213> ORGANISM: Artificial Sequence
<220> FEATURE:
<223> OTHER INFORMATION: Sox17-R RT-PCR primer

<400> SEQUENCE: 39
cttgcacacg aagtgcagat                                               20

<210> SEQ ID NO 40
<211> LENGTH: 23
<212> TYPE: DNA
<213> ORGANISM: Artificial Sequence
<220> FEATURE:
<223> OTHER INFORMATION: GAPDH-F primer for iPSC generation
```

<400> SEQUENCE: 40
gaacatcatc cctgcctcta ctg                                              23

<210> SEQ ID NO 41
<211> LENGTH: 24
<212> TYPE: DNA
<213> ORGANISM: Artificial Sequence
<220> FEATURE:
<223> OTHER INFORMATION: GAPDH-R primer for iPSC generation

<400> SEQUENCE: 41
caggaaatga gcttgacaaa gtgg                                             24

<210> SEQ ID NO 42
<211> LENGTH: 20
<212> TYPE: DNA
<213> ORGANISM: Artificial Sequence
<220> FEATURE:
<223> OTHER INFORMATION: EBNA-1-F primer for iPSC generation

<400> SEQUENCE: 42
atggacgagg acggggaaga                                                  20

<210> SEQ ID NO 43
<211> LENGTH: 20
<212> TYPE: DNA
<213> ORGANISM: Artificial Sequence
<220> FEATURE:
<223> OTHER INFORMATION: EBNA-1-R primer for iPSC generation

<400> SEQUENCE: 43
gccaatgcaa cttggacgtt                                                  20

<210> SEQ ID NO 44
<211> LENGTH: 20
<212> TYPE: DNA
<213> ORGANISM: Artificial Sequence
<220> FEATURE:
<223> OTHER INFORMATION: 293-F primer for TALENs activity

<400> SEQUENCE: 44
gagcagggag gcaagaatta                                                  20

<210> SEQ ID NO 45
<211> LENGTH: 20
<212> TYPE: DNA
<213> ORGANISM: Artificial Sequence
<220> FEATURE:
<223> OTHER INFORMATION: 293-R primer for TALENs activity

<400> SEQUENCE: 45
tgagggaaaa cgcatctagg                                                  20

<210> SEQ ID NO 46
<211> LENGTH: 20
<212> TYPE: DNA
<213> ORGANISM: homo sapiens

<400> SEQUENCE: 46
taaagtataa tgaaaactgt                                                  20

<210> SEQ ID NO 47
<211> LENGTH: 20
<212> TYPE: DNA

<213> ORGANISM: homo sapiens

<400> SEQUENCE: 47
gagagactgg ccaatctata                                           20

<210> SEQ ID NO 48
<211> LENGTH: 29
<212> TYPE: DNA
<213> ORGANISM: Artificial Sequence
<220> FEATURE:
<223> OTHER INFORMATION: PA2 RGEN 03 site-1 (intron22)

<400> SEQUENCE: 48
attcctgggc atattgagaa tttgtgttt                                 29

<210> SEQ ID NO 49
<211> LENGTH: 29
<212> TYPE: DNA
<213> ORGANISM: Artificial Sequence
<220> FEATURE:
<223> OTHER INFORMATION: PA2 RGEN 02 site-1 (intron22)

<400> SEQUENCE: 49
ctgtggtaag agtaccggtg ggaaggagt                                 29

<210> SEQ ID NO 50
<211> LENGTH: 29
<212> TYPE: DNA
<213> ORGANISM: Artificial Sequence
<220> FEATURE:
<223> OTHER INFORMATION: PA2 RGEN 03 site-2 (intron22)

<400> SEQUENCE: 50
aaacacaaat tctcaatatg cccaggaat                                 29

<210> SEQ ID NO 51
<211> LENGTH: 29
<212> TYPE: DNA
<213> ORGANISM: Artificial Sequence
<220> FEATURE:
<223> OTHER INFORMATION: PA2 RGEN 02 site-2 (intron22)

<400> SEQUENCE: 51
actccttccc accggtactc ttaccacag                                 29

<210> SEQ ID NO 52
<211> LENGTH: 25
<212> TYPE: DNA
<213> ORGANISM: Artificial Sequence
<220> FEATURE:
<223> OTHER INFORMATION: Co-1 Breakpoint Junction 1-1 (intron22)

<400> SEQUENCE: 52
attccttccg gtactcttac cacag                                     25

<210> SEQ ID NO 53
<211> LENGTH: 46
<212> TYPE: DNA
<213> ORGANISM: Artificial Sequence
<220> FEATURE:
<223> OTHER INFORMATION: Co-1 Breakpoint Junction 3-1 (intron22)

<400> SEQUENCE: 53
aaacacaaat tctcaattgt gaatattgga atgaatatta aggagt              46

```
<210> SEQ ID NO 54
<211> LENGTH: 25
<212> TYPE: DNA
<213> ORGANISM: Artificial Sequence
<220> FEATURE:
<223> OTHER INFORMATION: Co-1 Breakpoint Junction 1-2 (intron22)

<400> SEQUENCE: 54
ctgtggtaag agtaccggaa ggaat                                         25

<210> SEQ ID NO 55
<211> LENGTH: 46
<212> TYPE: DNA
<213> ORGANISM: Artificial Sequence
<220> FEATURE:
<223> OTHER INFORMATION: Co-1 Breakpoint Junction 3-2 (intron22)

<400> SEQUENCE: 55
actccttaat attcattcca atattcacaa ttgagaattt gtgttt                  46

<210> SEQ ID NO 56
<211> LENGTH: 24
<212> TYPE: DNA
<213> ORGANISM: Artificial Sequence
<220> FEATURE:
<223> OTHER INFORMATION: Co-2 Breakpoint Junction 1-1 (intron22)

<400> SEQUENCE: 56
attcctgggc aactcttacc acag                                          24

<210> SEQ ID NO 57
<211> LENGTH: 29
<212> TYPE: DNA
<213> ORGANISM: Artificial Sequence
<220> FEATURE:
<223> OTHER INFORMATION: Co-2 Breakpoint Junction 3-1 (intron22)

<400> SEQUENCE: 57
aaacacaaat tctcaatatg ggaaggagt                                     29

<210> SEQ ID NO 58
<211> LENGTH: 24
<212> TYPE: DNA
<213> ORGANISM: Artificial Sequence
<220> FEATURE:
<223> OTHER INFORMATION: Co-2 Breakpoint Junction 1-2 (intron22)

<400> SEQUENCE: 58
ctgtggtaag agttgcccag gaat                                          24

<210> SEQ ID NO 59
<211> LENGTH: 29
<212> TYPE: DNA
<213> ORGANISM: Artificial Sequence
<220> FEATURE:
<223> OTHER INFORMATION: Co-2 Breakpoint Junction 3-2 (intron22)

<400> SEQUENCE: 59
actccttccc atattgagaa tttgtgttt                                     29

<210> SEQ ID NO 60
<211> LENGTH: 22
<212> TYPE: DNA
<213> ORGANISM: Artificial Sequence
<220> FEATURE:
<223> OTHER INFORMATION: Co-3 Breakpoint Junction 1-1 (intron22)
```

<400> SEQUENCE: 60
attcctggta ctcttaccac ag                                              22

<210> SEQ ID NO 61
<211> LENGTH: 20
<212> TYPE: DNA
<213> ORGANISM: Artificial Sequence
<220> FEATURE:
<223> OTHER INFORMATION: Co-3 Breakpoint Junction 3-1 (intron22)

<400> SEQUENCE: 61
aaacacaaat tctcaatatg                                                 20

<210> SEQ ID NO 62
<211> LENGTH: 22
<212> TYPE: DNA
<213> ORGANISM: Artificial Sequence
<220> FEATURE:
<223> OTHER INFORMATION: Co-3 Breakpoint Junction 1-2 (intron22)

<400> SEQUENCE: 62
ctgtggtaag agtaccagga at                                              22

<210> SEQ ID NO 63
<211> LENGTH: 20
<212> TYPE: DNA
<213> ORGANISM: Artificial Sequence
<220> FEATURE:
<223> OTHER INFORMATION: Co-3 Breakpoint Junction 3-2 (intron22)

<400> SEQUENCE: 63
catattgaga atttgtgttt                                                 20

<210> SEQ ID NO 64
<211> LENGTH: 40
<212> TYPE: DNA
<213> ORGANISM: Artificial Sequence
<220> FEATURE:
<223> OTHER INFORMATION: Exon1 and Exon2

<400> SEQUENCE: 64
gagctgcctg tggacgcaag atttcctcct agagtgccaa                           40

<210> SEQ ID NO 65
<211> LENGTH: 40
<212> TYPE: DNA
<213> ORGANISM: Artificial Sequence
<220> FEATURE:
<223> OTHER INFORMATION: Exon22 and Exon23

<400> SEQUENCE: 65
attccactgg aaccttaatg gtcttctttg gcaatgtgga                           40

<210> SEQ ID NO 66
<211> LENGTH: 26
<212> TYPE: DNA
<213> ORGANISM: Artificial Sequence
<220> FEATURE:
<223> OTHER INFORMATION: int1 homolog1

<400> SEQUENCE: 66
gcaggtcccc ggggttgtgc ccctgg                                          26

<210> SEQ ID NO 67
<211> LENGTH: 26

```
<212> TYPE: DNA
<213> ORGANISM: Artificial Sequence
<220> FEATURE:
<223> OTHER INFORMATION: int1 homolog2

<400> SEQUENCE: 67
ccaggggcac aaccccgggg acctgc                                           26

<210> SEQ ID NO 68
<211> LENGTH: 20
<212> TYPE: DNA
<213> ORGANISM: Artificial Sequence
<220> FEATURE:
<223> OTHER INFORMATION: inverted seq Breakpoint junction 1-1 (intron1)

<400> SEQUENCE: 68
gcaggtcccc ggggttgtgg                                                  20

<210> SEQ ID NO 69
<211> LENGTH: 13
<212> TYPE: DNA
<213> ORGANISM: Artificial Sequence
<220> FEATURE:
<223> OTHER INFORMATION: inverted seq Breakpoint junction 1-2 (intron1)

<400> SEQUENCE: 69
gcaggtcccc tgg                                                         13

<210> SEQ ID NO 70
<211> LENGTH: 13
<212> TYPE: DNA
<213> ORGANISM: Artificial Sequence
<220> FEATURE:
<223> OTHER INFORMATION: inverted seq Breakpoint junction 2-1 (intron1)

<400> SEQUENCE: 70
cgtccagggg acc                                                         13

<210> SEQ ID NO 71
<211> LENGTH: 40
<212> TYPE: DNA
<213> ORGANISM: Artificial Sequence
<220> FEATURE:
<223> OTHER INFORMATION: intron 1 seq 1

<400> SEQUENCE: 71
ccaggggact ctggttgttg tcacaacccc ggggacctgc                            40

<210> SEQ ID NO 72
<211> LENGTH: 40
<212> TYPE: DNA
<213> ORGANISM: Artificial Sequence
<220> FEATURE:
<223> OTHER INFORMATION: intron 1 seq 2

<400> SEQUENCE: 72
gcaggtcccc ggggttgtga caacaaccag agtcccctgg                            40

<210> SEQ ID NO 73
<211> LENGTH: 13
<212> TYPE: DNA
<213> ORGANISM: Artificial Sequence
<220> FEATURE:
<223> OTHER INFORMATION: Co-3 Breakpoint junction 2-1 (intron1)

<400> SEQUENCE: 73
```
ccaggggacc tgc                                                    13

<210> SEQ ID NO 74
<211> LENGTH: 32
<212> TYPE: DNA
<213> ORGANISM: Artificial Sequence
<220> FEATURE:
<223> OTHER INFORMATION: WT RGEN 02 site-1 (intron22)

<400> SEQUENCE: 74
actccttccc accggtactc ttaccacagc at                               32

<210> SEQ ID NO 75
<211> LENGTH: 32
<212> TYPE: DNA
<213> ORGANISM: Artificial Sequence
<220> FEATURE:
<223> OTHER INFORMATION: WT RGEN 03 site-1 (intron22)

<400> SEQUENCE: 75
aggaaacaca aattctcaat atgcccagga at                               32

<210> SEQ ID NO 76
<211> LENGTH: 32
<212> TYPE: DNA
<213> ORGANISM: Artificial Sequence
<220> FEATURE:
<223> OTHER INFORMATION: WT RGEN 02 site-2 (intron22)

<400> SEQUENCE: 76
atgctgtggt aagagtaccg gtgggaagga gt                               32

<210> SEQ ID NO 77
<211> LENGTH: 32
<212> TYPE: DNA
<213> ORGANISM: Artificial Sequence
<220> FEATURE:
<223> OTHER INFORMATION: WT RGEN 03 site-2 (intron22)

<400> SEQUENCE: 77
attcctgggc atattgagaa tttgtgtttc ct                               32

<210> SEQ ID NO 78
<211> LENGTH: 32
<212> TYPE: DNA
<213> ORGANISM: Artificial Sequence
<220> FEATURE:
<223> OTHER INFORMATION: expected inverted seq(seamless) breakpoint
      junction 1-1

<400> SEQUENCE: 78
actccttccc atattgagaa tttgtgtttc ct                               32

<210> SEQ ID NO 79
<211> LENGTH: 32
<212> TYPE: DNA
<213> ORGANISM: Artificial Sequence
<220> FEATURE:
<223> OTHER INFORMATION: expected inverted seq(seamless) breakpoint
      junction 3-1

<400> SEQUENCE: 79
atgctgtggt aagagtaccg gtgcccagga at                               32

<210> SEQ ID NO 80
<211> LENGTH: 32

```
<212> TYPE: DNA
<213> ORGANISM: Artificial Sequence
<220> FEATURE:
<223> OTHER INFORMATION: expected inverted seq(seamless) breakpoint
      junction 1-2

<400> SEQUENCE: 80
aggaaacaca aattctcaat atgggaagga gt                                    32

<210> SEQ ID NO 81
<211> LENGTH: 32
<212> TYPE: DNA
<213> ORGANISM: Artificial Sequence
<220> FEATURE:
<223> OTHER INFORMATION: expected inverted seq(seamless) breakpoint
      junction 3-2

<400> SEQUENCE: 81
attcctgggc accggtactc ttaccacagc at                                    32

<210> SEQ ID NO 82
<211> LENGTH: 22
<212> TYPE: DNA
<213> ORGANISM: Artificial Sequence
<220> FEATURE:
<223> OTHER INFORMATION: Seq breakpoint junction 1-1 (intron22)

<400> SEQUENCE: 82
actctgagaa tttgtgtttc ct                                               22

<210> SEQ ID NO 83
<211> LENGTH: 25
<212> TYPE: DNA
<213> ORGANISM: Artificial Sequence
<220> FEATURE:
<223> OTHER INFORMATION: Seq breakpoint junction 3-1 (intron22)

<400> SEQUENCE: 83
atgctgtggt aagagtacca ggaat                                            25

<210> SEQ ID NO 84
<211> LENGTH: 22
<212> TYPE: DNA
<213> ORGANISM: Artificial Sequence
<220> FEATURE:
<223> OTHER INFORMATION: Seq breakpoint junction 1-2 (intron22)

<400> SEQUENCE: 84
aggaaacaca aattctcaga gt                                               22

<210> SEQ ID NO 85
<211> LENGTH: 25
<212> TYPE: DNA
<213> ORGANISM: Artificial Sequence
<220> FEATURE:
<223> OTHER INFORMATION: Seq breakpoint junction 3-2 (intron22)

<400> SEQUENCE: 85
attcctggta ctcttaccac agcat                                            25

<210> SEQ ID NO 86
<211> LENGTH: 18
<212> TYPE: DNA
<213> ORGANISM: Artificial Sequence
<220> FEATURE:
<223> OTHER INFORMATION: Seq breakpoint junction 1-3 (intron22)
```

```
<400> SEQUENCE: 86
gttgaatttg tgtttcct                                              18

<210> SEQ ID NO 87
<211> LENGTH: 18
<212> TYPE: DNA
<213> ORGANISM: Artificial Sequence
<220> FEATURE:
<223> OTHER INFORMATION: Seq breakpoint junction 1-4 (intron22)

<400> SEQUENCE: 87
aggaaacaca aattcaac                                              18

<210> SEQ ID NO 88
<211> LENGTH: 18
<212> TYPE: DNA
<213> ORGANISM: Artificial Sequence
<220> FEATURE:
<223> OTHER INFORMATION: Seq breakpoint junction 1-5 (intron22)

<400> SEQUENCE: 88
tgagaatttg tgtttcct                                              18

<210> SEQ ID NO 89
<211> LENGTH: 18
<212> TYPE: DNA
<213> ORGANISM: Artificial Sequence
<220> FEATURE:
<223> OTHER INFORMATION: Seq breakpoint junction 1-6 (intron22)

<400> SEQUENCE: 89
aggaaacaca aattctca                                              18

<210> SEQ ID NO 90
<211> LENGTH: 63
<212> TYPE: DNA
<213> ORGANISM: Artificial Sequence
<220> FEATURE:
<223> OTHER INFORMATION: intron 22 seq 1

<400> SEQUENCE: 90
actccttccc aatgtatttc atatcctctc attcattctc aatattgaga atttgtgttt     60
cct                                                                  63

<210> SEQ ID NO 91
<211> LENGTH: 63
<212> TYPE: DNA
<213> ORGANISM: Artificial Sequence
<220> FEATURE:
<223> OTHER INFORMATION: intron 22 seq 2

<400> SEQUENCE: 91
aggaaacaca aattctcaat attgagaatg aatgagagga tatgaaatac attgggaagg     60
agt                                                                  63

<210> SEQ ID NO 92
<211> LENGTH: 12
<212> TYPE: DNA
<213> ORGANISM: Artificial Sequence
<220> FEATURE:
<223> OTHER INFORMATION: Seq breakpoint junction 1-1 (intron1)

<400> SEQUENCE: 92
gcacataagt tg                                                    12
```

<210> SEQ ID NO 93
<211> LENGTH: 32
<212> TYPE: DNA
<213> ORGANISM: Artificial Sequence
<220> FEATURE:
<223> OTHER INFORMATION: Seq breakpoint junction 1-2 (intron1)

<400> SEQUENCE: 93
gcaggtcccc ggggttgtgc ccctggagct ct                                    32

<210> SEQ ID NO 94
<211> LENGTH: 12
<212> TYPE: DNA
<213> ORGANISM: Artificial Sequence
<220> FEATURE:
<223> OTHER INFORMATION: Seq breakpoint junction 1-3 (intron1)

<400> SEQUENCE: 94
gaaaaaagtt gg                                                          12

<210> SEQ ID NO 95
<211> LENGTH: 12
<212> TYPE: DNA
<213> ORGANISM: Artificial Sequence
<220> FEATURE:
<223> OTHER INFORMATION: Seq breakpoint junction 1-4 (intron1)

<400> SEQUENCE: 95
caacttatgt gc                                                          12

<210> SEQ ID NO 96
<211> LENGTH: 32
<212> TYPE: DNA
<213> ORGANISM: Artificial Sequence
<220> FEATURE:
<223> OTHER INFORMATION: Seq breakpoint junction 1-5 (intron1)

<400> SEQUENCE: 96
agagctccag gggcacaacc ccggggacct gc                                    32

<210> SEQ ID NO 97
<211> LENGTH: 12
<212> TYPE: DNA
<213> ORGANISM: Artificial Sequence
<220> FEATURE:
<223> OTHER INFORMATION: Seq breakpoint junction 1-6 (intron1)

<400> SEQUENCE: 97 ccaactttt tc                                                           12

<210> SEQ ID NO 98
<211> LENGTH: 12
<212> TYPE: DNA
<213> ORGANISM: Artificial Sequence
<220> FEATURE:
<223> OTHER INFORMATION: Seq breakpoint junction 2-1 (intron1)

<400> SEQUENCE: 98
caaccctttt tc                                                          12

<210> SEQ ID NO 99
<211> LENGTH: 12
<212> TYPE: DNA
<213> ORGANISM: Artificial Sequence
<220> FEATURE:

<223> OTHER INFORMATION: Seq breakpoint junction 2-2 (intron1)

<400> SEQUENCE: 99 caactttgt ta                                                            12

<210> SEQ ID NO 100
<211> LENGTH: 12
<212> TYPE: DNA
<213> ORGANISM: Artificial Sequence
<220> FEATURE:
<223> OTHER INFORMATION: Seq breakpoint junction 2-3 (intron1)

<400> SEQUENCE: 100
gaaaaagggt tg                                                           12

<210> SEQ ID NO 101
<211> LENGTH: 12
<212> TYPE: DNA
<213> ORGANISM: Artificial Sequence
<220> FEATURE:
<223> OTHER INFORMATION: Seq breakpoint junction 2-4 (intron1)

<400> SEQUENCE: 101
taacaaaagt tg                                                           12

<210> SEQ ID NO 102
<211> LENGTH: 29
<212> TYPE: DNA
<213> ORGANISM: Artificial Sequence
<220> FEATURE:
<223> OTHER INFORMATION: Corrected seq. (seamless/predicted) breakpoint
      junction 1-1

<400> SEQUENCE: 102
attcctgggc accggtactc ttaccacag                                         29

<210> SEQ ID NO 103
<211> LENGTH: 29
<212> TYPE: DNA
<213> ORGANISM: Artificial Sequence
<220> FEATURE:
<223> OTHER INFORMATION: Corrected seq. (seamless/predicted) breakpoint
      junction 1-2

<400> SEQUENCE: 103
ctgtggtaag agtaccggtg cccaggaat                                         29

<210> SEQ ID NO 104
<211> LENGTH: 23
<212> TYPE: DNA
<213> ORGANISM: Artificial Sequence
<220> FEATURE:
<223> OTHER INFORMATION: Corrected seq. (seamless/predicted) breakpoint
      junction 1-3

<400> SEQUENCE: 104
attcctgggt actcttacca cag                                               23

<210> SEQ ID NO 105
<211> LENGTH: 16
<212> TYPE: DNA
<213> ORGANISM: Artificial Sequence
<220> FEATURE:
<223> OTHER INFORMATION: Corrected seq. (seamless/predicted) breakpoint
      junction 3-1

<400> SEQUENCE: 105
aaacacaaat tctctt                                                         16

<210> SEQ ID NO 106
<211> LENGTH: 23
<212> TYPE: DNA
<213> ORGANISM: Artificial Sequence
<220> FEATURE:
<223> OTHER INFORMATION: Corrected seq. (seamless/predicted) breakpoint
      junction 1-6

<400> SEQUENCE: 106
ctgtggtaag agtacccagg aat                                                 23

<210> SEQ ID NO 107
<211> LENGTH: 16
<212> TYPE: DNA
<213> ORGANISM: Artificial Sequence
<220> FEATURE:
<223> OTHER INFORMATION: Corrected seq. (seamless/predicted) breakpoint
      junction 3-2

<400> SEQUENCE: 107
aagagaattt gtgttt                                                         16

<210> SEQ ID NO 108
<211> LENGTH: 34
<212> TYPE: DNA
<213> ORGANISM: Artificial Sequence
<220> FEATURE:
<223> OTHER INFORMATION: Corrected seq. (seamless/predicted) breakpoint
      junction 3-3

<400> SEQUENCE: 108
aaacacaaat tctcaatatg cggtgggaag gagt                                     34

<210> SEQ ID NO 109
<211> LENGTH: 34
<212> TYPE: DNA
<213> ORGANISM: Artificial Sequence
<220> FEATURE:
<223> OTHER INFORMATION: Corrected seq. (seamless/predicted) breakpoint
      junction 3-4

<400> SEQUENCE: 109
actccttccc accgcatatt gagaatttgt gttt                                     34

<210> SEQ ID NO 110
<211> LENGTH: 28
<212> TYPE: DNA
<213> ORGANISM: Artificial Sequence
<220> FEATURE:
<223> OTHER INFORMATION: Corrected seq. (seamless/predicted) breakpoint
      junction 3-5

<400> SEQUENCE: 110
aaacacaaat tctcaatatg gaaggagt                                            28

<210> SEQ ID NO 111
<211> LENGTH: 28
<212> TYPE: DNA
<213> ORGANISM: Artificial Sequence
<220> FEATURE:
<223> OTHER INFORMATION: Corrected seq. (seamless/predicted) breakpoint
      junction 3-6

<400> SEQUENCE: 111

```
actccttcca tattgagaat ttgtgttt                                            28

<210> SEQ ID NO 112
<211> LENGTH: 56
<212> TYPE: DNA
<213> ORGANISM: Artificial Sequence
<220> FEATURE:
<223> OTHER INFORMATION: Talen target site(homolog1)

<400> SEQUENCE: 112
cataaagtat aatgaaaact gttggacaca caaggagaga ctggccaatc tatagt          56

<210> SEQ ID NO 113
<211> LENGTH: 57
<212> TYPE: DNA
<213> ORGANISM: Artificial Sequence
<220> FEATURE:
<223> OTHER INFORMATION: Talen target site(homolog2)

<400> SEQUENCE: 113
actatagatt ggccagtctc tccttgtgtg tccaacagtt ttcattatac tttatgt        57

<210> SEQ ID NO 114
<211> LENGTH: 54
<212> TYPE: DNA
<213> ORGANISM: Artificial Sequence
<220> FEATURE:
<223> OTHER INFORMATION: Homolog 1(breakpoint)

<400> SEQUENCE: 114
cataaagtat aatgaaaact gttggacaca aggagagact ggccaatcta tagt            54

<210> SEQ ID NO 115
<211> LENGTH: 55
<212> TYPE: DNA
<213> ORGANISM: Artificial Sequence
<220> FEATURE:
<223> OTHER INFORMATION: Homolog 2(breakpoint)

<400> SEQUENCE: 115
actatagatt ggccagtctc tccttgtgtc caacagtttt cattatactt tatgt          55

<210> SEQ ID NO 116
<211> LENGTH: 20
<212> TYPE: DNA
<213> ORGANISM: Artificial Sequence
<220> FEATURE:
<223> OTHER INFORMATION: Potential off-target sites of TALEN 01(chr.9,
      Left-half site)

<400> SEQUENCE: 116
tatagatttg ccattttctc                                                  20

<210> SEQ ID NO 117
<211> LENGTH: 20
<212> TYPE: DNA
<213> ORGANISM: Artificial Sequence
<220> FEATURE:
<223> OTHER INFORMATION: Potential off-target sites of TALEN 01(chr.9,
      Right-half site)

<400> SEQUENCE: 117
taaaatataa agaaaagttt                                                  20

<210> SEQ ID NO 118
<211> LENGTH: 20
```

```
<212> TYPE: DNA
<213> ORGANISM: Artificial Sequence
<220> FEATURE:
<223> OTHER INFORMATION: Potential off-target sites of TALEN 01(chr.14,
      Left-half site)

<400> SEQUENCE: 118
tgtagattgg tcagtgtctc                                          20

<210> SEQ ID NO 119
<211> LENGTH: 20
<212> TYPE: DNA
<213> ORGANISM: Artificial Sequence
<220> FEATURE:
<223> OTHER INFORMATION: Potential off-target sites of TALEN 01(chr.14,
      Right-half site)

<400> SEQUENCE: 119
aaaagcaaac tcaaaactgt                                          20

<210> SEQ ID NO 120
<211> LENGTH: 20
<212> TYPE: DNA
<213> ORGANISM: Artificial Sequence
<220> FEATURE:
<223> OTHER INFORMATION: Potential off-target sites of TALEN 01(chr.4,
      Left-half site)

<400> SEQUENCE: 120
ttttgattgg ccagcctctc                                          20

<210> SEQ ID NO 121
<211> LENGTH: 20
<212> TYPE: DNA
<213> ORGANISM: Artificial Sequence
<220> FEATURE:
<223> OTHER INFORMATION: Potential off-target sites of TALEN 01(chr.4,
      Right-half site)

<400> SEQUENCE: 121
aaaagaaaac tgaaaacaga                                          20
```

TALEN TARGETING BLOOD COAGULATION FACTOR VIII INTRON 1 INVERSION GENE AND COMPOSITION FOR TREATING HEMOPHILIA COMPRISING SAME

CROSS-REFERENCE TO RELATED APPLICATIONS

This application is a continuation application of U.S. application Ser. No. 15/541,784, filed 6 Jul. 2017, which is the national phase application of PCT Application No. PCT/KR2016/000101, filed on 6 Jan. 2016, which claims the benefit and priority to Korean Patent Application Nos. 10-2015-0001392, filed 6 Jan. 2015 and 10-2015-0001391 filed 6 Jan. 2015. The entire disclosures of the applications identified in this paragraph are incorporated herein by references.

TECHNICAL FIELD

The present invention relates to a composition for treating hemophilia A using endonuclease targeting the blood coagulation factor VIII gene.

BACKGROUND ART

Hemophilia A is one of the most common genetic bleeding disorders, with an incidence of 1 in 5,000 males worldwide. This disorder is caused by various genetic mutations in the X-linked coagulation factor VIII (F8) gene. Clinical symptoms vary widely according to the genotypes. Hemophilia A can be characterized as severe (<1% activity), moderate (1-5% activity), or mild (5-30% activity), depending on the relative amount of F8 activity in the patient's plasma (Graw et al., 2005). Approximately 50% of severe hemophilia A cases are caused by chromosomal inversions that include F8 1 intron homologue (int1h, about 5% of severe A hemophilia) and 22 intron homologue (int22h, about 40% of severe A hemophilia) rather than a point mutation. These two inversions result from erroneous restoration of DNA double-strand breaks (DSB) induced by homologous recombination through nonallelic homologous recombination (NAHR).

Previously, the inventors used zinc finger nuclease (ZFN) from the immortalized wild-type human cell lines and TALEN(transcriptional activator-like effect nuclease) from iPSC (induced pluripotent stem cell) in order to chromosomal segments between two identical int1h sequences (int1h-1 and int1h-2) that are 140 kbp apart and have a frequency of 0.1% and 1.9%, respectively (Park et al., 2014). This method artificially induces inverted genotypes mimicking the erroneous DSB repair. Other 600-kbp inversions comprising three int22h sequences (int22h-1, -2 and -3) were 8 times more frequent than the 140-kbp inversion, but the size of the inverted region was large and there were three homologues on the X chromosome, which made recovery more difficult. Furthermore, int22h (10 kbp) is much larger than int1h (1 kbp), so it is very difficult to analyze the genotype of the int22h inversion or repair using conventional PCR because the entire 10-kbp int22h should be amplified. In fact, it has not known that the 600-kbp chromosome segment comprising int22h in human cells, as well as patient-derived iPSCs, can be restored using programmable nuclease.

The present inventors, as a short repeated Cas (CRISPR/CRISPR-associated) having type II bundle with a regular intervals, tried to repair two inversions in iPSC derived from type A hemophilia patients using RGEN (RNA-guided engineered nuclease) (Cho et al, 2013; Cho et al, 2014).

Moreover, the inventors have shown that TALENs can be used to invert the 140-kbp chromosomal segment in human iPSCs to create hemophilia A model cell lines that recapitulate one of the most frequent genotypes of hemophilia A and to flip-flop the inverted region back to the wild-type state. Importantly, the F8 mRNA is expressed in cells differentiated from reverted—i.e., genome-corrected—iPSCs but not in cells differentiated from the hemophilia model iPSCs. To the best of our knowledge, this report is the first demonstration that engineered nucleases can be used to rearrange large genomic segments in iPSCs and to isolate clones harboring such genomic rearrangements, providing a proof-of-principle for correcting genetic defects caused by genome rearrangements in iPSCs.

Throughout the entire specification, many cited documents and patent documents are referenced and their citations are represented. The disclosures of cited documents and patent documents are entirely incorporated by reference into the present specification, and the level of the technical field within which the present invention falls, and details of the present invention are explained more clearly.

DETAILED DESCRIPTION OF THE INVENTION

Technical Problem

The present inventors researched and endeavored to develop an efficient and fundamental therapy for hemophilia A which is caused by various genetic mutations in the blood coagulation factor VIII (F8) gene. As a result, the present inventors found that an inversion of the F8 gene could be successfully corrected using the guiding RNA that targets an inverted region and the RNA-guided endonuclease that cleaves a site targeted by the guiding RNA, and thus completed the present invention. In addition, the present inventors found that an inversion of the F8 gene could be successfully corrected using TAL effector domains that target an inverted region and a pair of endonuclease that bind to the domains, respectively, to cleave a gene site targeted by the domains, and thus completed the present invention.

Therefore, an aspect of the present invention is to provide a composition for correcting an inversion of the blood coagulation factor VIII gene and a method for correcting an inversion using the blood coagulation factor VIII (F8) gene.

Another aspect of the present invention is to provide a method for preparing induced pluripotent stem cells having an inversion-corrected blood coagulation factor VIII (F8) gene, induced pluripotent stem cells prepared by the method, and a composition containing the induced pluripotent stem cells as an active ingredient for treating hemophilia A.

Other purposes and advantages of the present invention will become more obvious with the following detailed description of the invention, claims, and drawings.

Technical Solution

In accordance with an aspect of the present invention, there is provided a composition for correcting an inversion of the blood coagulation factor VIII (F8) gene, the composition comprising:

(a) RNA-guided endonuclease or a nucleotide sequence encoding the RNA-guided endonuclease; and (b) guiding RNA specifically recognizing the following nucleotide sequences or complementary sequences thereof, or a nucleotide encoding the guiding RNA, the specifically recognized nucleotide sequences being a pair of nucleotide sequences selected from the group consisting of:

(i) the nucleotide sequence of SEQ ID NO: 1;

(ii) the nucleotide sequence of SEQ ID NO: 2; and (iii) a 15- to 25-bp nucleotide sequence present in the 562,975-bp nucleotide sequence between (i) and (ii) on intron 22 of the F8 gene, wherein (iii) does not have a nucleotide sequence, which has sequence homology of at least 80% with (i) or (ii) in the 562,975-bp nucleotide between (i) and (ii), and simultaneously, of which the 5'-N(G/A)G-3' nucleotide is linked downstream.

In accordance with another aspect of the present invention, there is provided a method for correcting an inversion of the blood coagulation factor VIII (F8) gene, the method including bringing somatic cells of a hemophilia A patient into contact with the composition of the present invention or transfecting the somatic cells with a gene delivery system having the composition inserted thereinto.

According to the present invention, the nucleotide sequence of SEQ ID NO: 1 is the first nucleotide sequence appearing among 20-bp consecutive nucleotide sequences present downstream of the int22h-1 of the F8 gene, wherein each of the nucleotide sequences does not have another nucleotide sequence, which has sequence homology of at least 80% in the 20-bp consecutive nucleotide sequences and of which the 5'-N(G/A)G-3' nucleotide sequence is directly linked downstream, and the nucleotide sequence of SEQ ID NO: 2 is the second nucleotide sequence appearing among 20-bp consecutive nucleotide sequences present upstream of the int22h-3 of the F8 gene, wherein each of the nucleotide sequences does not have another nucleotide sequence, which has sequence homology of at least 80% in the 20-bp consecutive nucleotide sequences and of which the 5'-N(G/A)G-3' nucleotide is directly linked upstream. Therefore, when the two sequences or a nucleotide sequence, which satisfies the above-described conditions in (iii) and is present between these two sequences, is used as a target, an inversion occurring in intron 22 of the F8 gene, more specifically, an inversion occurring between int22h-1 and int22h-3 can be corrected.

According to the present invention, the nucleotide sequence of SEQ ID NO: 1 is the first nucleotide sequence appearing among 20-bp consecutive nucleotide sequences present upstream of the int22h-1 of the F8 gene, wherein each of the nucleotide sequences does not have another nucleotide sequence, which has sequence homology of at least 80% in the 20-bp consecutive nucleotide sequences and of which the 5'-N(G/A)G-3' nucleotide sequence is directly linked upstream, and the nucleotide sequence of SEQ ID NO: 2 is the first nucleotide sequence appearing among 20-bp consecutive nucleotide sequences present downstream of the int22h-3 of the F8 gene, wherein each of the nucleotide sequences does not have another nucleotide sequence, which has sequence homology of at least 80% in the 20-bp consecutive nucleotide sequences and of which the 5'-N(G/A)G-3' nucleotide is directly linked downstream. Therefore, when the two sequences or a nucleotide sequence, which satisfies the above-described conditions in (iii) and is present between these two sequences, is used as a target, an inversion occurring in intron 22 of the F8 gene, more specifically, an inversion occurring between int22h-1 and int22h-3 can be corrected.

According to a specific embodiment of the present invention, the RNA-guided endonuclease used in the present invention is CRISPR associated protein 9 (Cas9).

According to a specific embodiment of the present invention, the guiding RNA used in the present invention specifically recognizes the nucleotide sequences of SEQ ID NO: 1 and SEQ ID NO: 2 or complementary sequences thereof.

According to the present invention, the RNA-guided endonuclease and guiding RNA may be used in forms of a protein and transcribed RNA, and may be delivered to target cells by transfection with vectors in which DNAs encoding the RNA-guided endonuclease and guiding RNA are loaded, respectively.

In accordance with still another aspect of the present invention, there is provided a composition for correcting an inversion of the blood coagulation factor VIII (F8) gene, the composition comprising:

(a) RNA-guided endonuclease or a nucleotide sequence encoding the RNA-guided endonuclease; and (b) guiding RNA specifically recognizing the following nucleotide sequence or a complementary sequence thereof, or a nucleotide encoding the guiding RNA, the specifically recognized nucleotide sequence being a 15- to 25-bp nucleotide sequence included in the nucleotide sequence of SEQ ID NO: 4, wherein the 5- to 25-bp nucleotide sequence does not have a nucleotide sequence, which has sequence homology of at least 80% in the nucleotide sequence of SEQ ID NO: 4, and at the same time, of which the 5'-N(G/A)G-3' nucleotide is linked downstream.

According to the present invention, while an inversion occurring in intron 22 of the F8 gene can be corrected according to the above-described aspect of the invention, an inversion occurring in intron 1 of the F8 gene can also be corrected by using guiding RNA targeting a sequence of SEQ ID NO: 4 in intron 1 of the F8 gene.

According to a specific embodiment of the present invention, the guiding RNA used in the present invention specifically recognizes the nucleotide sequence of SEQ ID NO: 3 or a complementary sequence thereof. The nucleotide sequence of SEQ ID NO: 3 is a consecutive nucleotide sequence present both in intron 1 homology (int1h-1) and int1h-2, and an inversion occurring between int1h-1 and int1h-2 can be corrected using guiding RNA targeting the nucleotide sequence of SEQ ID NO: 3.

According to a specific embodiment of the present invention, the RNA-guided endonuclease used in the present invention is CRISPR associated protein 9 (Cas9).

In accordance with still another aspect of the present invention, there is provided having an inversion-corrected blood coagulation factor VIII (F8) gene, the method including:

(a) reprogramming somatic cells isolated from a hemophilia A patient to obtain induced pluripotent stem cells; and (b) bringing the induced pluripotent stem cells into contact with the composition of the present invention or transfecting the induced pluripotent stem cells with a gene delivery system having the composition inserted thereinto.

The induced pluripotent stem cells obtained by reprogramming somatic cells isolated from a hemophilia A patient retain a distinctive inverted gene of the patient, which can be corrected in vitro through the method of the present invention. That is, when guiding RNA specifically recognizing an inverted region after the inverted region is checked, the inversion is corrected at a predetermined frequency, thereby obtaining patient-customized induced pluripotent stem cells having the same genotype as a wild type.

In accordance with still another aspect of the present invention, there are provided induced pluripotent stem cells prepared by the method of the present invention.

In accordance with still another aspect of the present invention, there is provided a composition comprising the induced pluripotent stem cells of the present invention as an active ingredient for treating hemophilia A.

The induced pluripotent stem cells of the present invention are cells obtained by correcting a genetic inversion of a hemophilia A patient. The induced pluripotent stem cells are differentiated into appropriate somatic cells, which are then transplanted in the patient to express the corrected gene, so that the induced pluripotent stem cells can be used for a composition for cell therapy, which is useful for hemophilia A corresponding to an incurable disease. Therefore, the composition of the present invention can induce the differentiation into target cells in vivo while being directly transplanted in the body, or can be completely differentiated into target cells in vitro and then inserted into the body.

In accordance with still another aspect of the present invention, there is provided a composition for inducing an inversion of the blood coagulation factor VIII (F8) gene, the composition comprising:

(a) RNA-guided endonuclease or a nucleotide sequence encoding the RNA-guided endonuclease; and (b) guiding RNA specifically recognizing the following nucleotide sequences or complementary sequences thereof, or a nucleotide encoding the guiding RNA, the specifically recognized nucleotide sequences being a pair of nucleotide sequences selected from the group consisting of:

(i) the nucleotide sequence of SEQ ID NO: 1;

(ii) the nucleotide sequence of SEQ ID NO: 2; and (iii) a 15- to 25-bp nucleotide sequence present in the 562,975-bp nucleotide sequence between (i) and (ii) on intron 22 of the F8 gene, wherein (iii) does not have a nucleotide sequence, which has sequence homology of at least 80% with (i) or (ii) in the 562,975-bp nucleotide between (i) and (ii), and simultaneously, of which the 5'-N(G/A)G-3' nucleotide is linked downstream.

In accordance with still another aspect of the present invention, there is provided a composition for inducing an inversion of the blood coagulation factor VIII (F8) gene, the composition comprising:

(a) RNA-guided endonuclease or a nucleotide sequence encoding the RNA-guided endonuclease; and (b) guiding RNA specifically recognizing the following nucleotide sequence or a complementary sequence thereof, or a nucleotide sequence encoding the guiding RNA, the specifically recognized nucleotide sequence being a 15- to 25-bp nucleotide sequence included in the nucleotide sequence of SEQ ID NO: 4, wherein the 15- to 25-bp nucleotide sequence does not have a nucleotide sequence, which has sequence homology of at least 80% in the nucleotide sequence of SEQ ID NO: 4, and simultaneously, of which the 5'-N(G/A)G-3' nucleotide is linked downstream.

Since respective elements used in the present invention have been already described, the descriptions thereof will be omitted to avoid excessive overlapping.

According to the present invention, when the method of the present invention is carried out by using inverted patient cells as a start material, recurrence of the inversion, that is, correction can be induced, but on the contrary, an inverse can be induced when cells of a normal person are used as a start material. Therefore, the present invention can be a useful research tool for efficiently obtaining artificial hemophilia cells by using the cells with normal genotypes as start cells.

In accordance with still another aspect of the present invention, there is provided a method for inducing an inversion of the blood coagulation factor VIII (F8) gene, the method including introducing the composition of the present invention into somatic cells of a normal person.

Since respective compositions and steps used in the present invention have been already described, the descriptions thereof will be omitted to avoid excessive overlapping.

In accordance with still another aspect of the present invention, there is provided a composition for correcting an inversion of the blood coagulation factor VIII (F8) gene, the composition comprising a polypeptide including the following or a nucleotide sequence encoding the polypeptide (a) a pair of endonucleases; and (b) a pair of transcription activator-like (TAL) effector domains, each of which is linked to each of the endonucleases and includes an amino acid sequence specifically recognizing an inverted region of the F8 gene.

In accordance with another aspect of the present invention, there is provided a method for correcting an inversion of the blood coagulation factor VIII (F8) gene, the method including bringing somatic cells of a hemophilia A patient into contact with the composition of the present invention or transfecting the somatic cells with a gene delivery system having the composition inserted thereinto.

According to the present invention, a target site is guided by using TAL effector domains specifically binding to an inverted region of the F8 gene, and the target site is accurately cleaved by the endonucleases binding to the domains to cleave both end regions of the gene, which is inverted due to an inversion. The cleaved gene site is subjected to a re-inversion at a predetermined frequency, thereby ultimately achieving the correction of inversion.

As used herein, the term "specifically recognizing" refers to selectively recognizing a target sequence by an interaction with the target sequence, and the term is used in the same meaning as the term "specifically annealing". The TAL effector used in the present invention has a central repeat domain composed of 34 amino acids, and the 12th and 13th amino acid residues may be various amino acids and thus called the repeat variable diresidue (RVD). Each RVD serves to identify the base of a particular DNA, and to specifically recognize and bind (NI=A, NN=G, NG=T, and HD=C) (Boch J, et al. Science 326 (5959):1509-1512 (2009)). Therefore, in the presence of the information for the target DNA sequence, the TAL effector amino acid sequence that specifically binds to the target DNA sequence can be determined based on these codes.

According to a specific embodiment of the present invention, the inversion of the F8 gene, which is corrected by the present invention, is an inversion on intron 1 of the F8 gene; the pair of transcription activator-like (TAL) effector domains specifically bind to nucleotide sequences at first and second locations, which are included in the nucleotide sequence of SEQ ID NO: 31, respectively; and the nucleotide sequences at the first and second locations are separated from each other by a length of 10-20 bp while being 15- to 25-bp in length. According to the present invention, the nucleotide sequence of SEQ ID NO: 31 is a nucleotide sequence (about 1 kb) of homolog 1 in intron 1 of the F8 gene. Therefore, a left TAL effector and a right TAL effector bind to the first and second locations, respectively, and a pair of endonucleases linked to the left and right TAL effectors accurately cleave a 10- to 20-bp (spacer) region between the first location and the second location.

According to a specific embodiment of the present invention, the nucleotide sequences at the first and second locations are the nucleotide sequences of SEQ ID NO: 46 and SEQ ID NO: 47, respectively.

More specifically, the amino acid sequence specifically binding to the nucleotide sequence of SEQ ID NO: 46 of the present invention includes the amino acid sequence of SEQ ID NO: 29.

More specifically, the amino acid sequence specifically binding to the nucleotide sequence of SEQ ID NO: 47 of the present invention includes the amino acid sequence of SEQ ID NO: 30.

According to a specific embodiment of the present invention, the endonuclease used in the present invention is FokI endonuclease.

According to the present invention, the endonuclease and TAL effector of the present invention may be used in a form of protein, and these may be delivered to a target cell by transfecting the target cell with vectors loading DNA encoding the proteins.

In accordance with another aspect of the present invention, there is provided a method for preparing induced pluripotent stem cells having an inversion-corrected blood coagulation factor VIII (F8) gene, the method including:

(a) reprogramming somatic cells isolated from a hemophilia A patient to obtain induced pluripotent stem cells; and (b) bringing the induced pluripotent stem cells into contact with the composition of the present invention or transfecting the induced pluripotent stem cells with a gene delivery system having the composition inserted thereinto.

The induced pluripotent stem cells obtained by reprogramming somatic cells isolated from a hemophilia A patient retain a distinctive inverted gene of the patient, which can be corrected in vitro through the method of the present invention. That is, when TAL effector domains specifically recognizing an inverted region after the inverted region is checked, the inversion is corrected at a predetermined frequency, thereby obtaining patient-customized induced pluripotent stem cells having the same genotype as a wild type.

According to a specific embodiment of the present invention, a pair of TAL effector domains of the present invention are separated from each other, with a region to be cleaved on the F8 gene therebetween, by a length of 10-20 bp, more specifically, 12-16 bp, and most specifically 12-14 bp.

According to a specific embodiment of the present invention, the hemophilia A is caused by an inversion occurring in intron 1 of the F8 gene, and the pair of transcription activator-like (TAL) effector domains include amino acid sequences specifically binding to the nucleotide sequences of SEQ ID NO: 46 and SEQ ID NO: 47

The present embodiment is for preparing induced pluripotent stem cells wherein an inversion of hemophilia A, which is caused by an inverted region in intron 1 of the F8 gene out of hemophilia A cases, is corrected, and respective elements and steps therefor have been already described, and thus the descriptions thereof will be omitted to avoid excessive overlapping.

In accordance with another aspect of the present invention, there are induced pluripotent stem cells prepared by the method of the present invention.

In accordance with still another aspect of the present invention, there is provided a composition comprising the induced pluripotent stem cells of the present invention as an active ingredient for treating hemophilia A.

The induced pluripotent stem cells of the present invention are cells obtained by correcting a genetic inversion of a hemophilia A patient. The induced pluripotent stem cells are differentiated into appropriate somatic cells, which are then transplanted in the patient to express the corrected gene, and thus can be used for a composition for cell therapy, which is useful for hemophilia A corresponding to an incurable disease. Therefore, the composition of the present invention can induce the differentiation into target cells in vivo while being directly transplanted in the body, or can be completely differentiated into target cells in vitro and then inserted into the body.

In accordance with still another aspect of the present invention, there is provided a composition for inducing an inversion of the blood coagulation factor VIII (F8) gene, the composition comprising a polypeptide including the following or a nucleotide sequence encoding the polypeptide:

(a) a pair of endonucleases; and (b) a transcription activator-like (TAL) effector domain, which is linked to one of (a) and includes an amino acid sequence specifically binding to a nucleotide sequence at a first location on the F8 gene; and (c) a transcription activator-like (TAL) effector domain, which is linked to one of (a) and includes an amino acid sequence specifically binding to a nucleotide sequence at a second location on the F8 gene, or a nucleotide sequence encoding the effector domain, wherein the first and second locations are separated from each other by a length of 10-20 bp while being 15- to 25-bp in length.

Since respective elements used in the present invention have been already described, the descriptions thereof will be omitted to avoid excessive overlapping.

According to the present invention, when the method of the present invention is carried out by using inverted patient cells as a start material, recurrence of the inversion, that is, correction can be induced, but on the contrary, an inverse can be induced when cells of a normal person are used as a start material. Therefore, the present invention can be a useful research tool for efficiently obtaining artificial hemophilia cells by using the cells with normal genotypes as start cells.

In accordance with still another aspect of the present invention, there is provided a method for inducing an inversion of the blood coagulation factor VIII (F8) gene, the method including introducing the composition of the present invention into somatic cells of a normal person.

Since respective compositions and steps used in the present invention have been already described, the descriptions thereof will be omitted to avoid excessive overlapping.

Hereinafter, the matters that are commonly applied to the above-described present invention will be described.

As used herein, the term "nucleotide" refers to a deoxyribonucleotide or ribonucleotide existing in a single-strand type or a double-strand type, and includes analogs of naturally occurring nucleotides unless otherwise particularly specified (Scheit, Nucleotide Analogs, John Wiley, New York (1980); Uhlman and Peyman, Chemical Reviews, 90:543-584(1990)).

As used herein, the term "specifically recognizing" refers to selectively recognizing a target sequence on the basis of the complementarity with the target sequence of the present invention, and the term is used in the same meaning as the term "specifically annealing". The term "complementary" refers to being sufficiently complementary such that guiding RNA of the present invention is selectively hybridized with a target nucleic acid sequence under predetermined annealing or hybridizing conditions, and the term is meant to encompass "substantially complementary" and "perfectly complementary", and means preferably "perfectly complementary". As used herein, the term "substantially complementary sequence" is meant to encompass a sequence that is partially not identical to the sequence of the comparative subject within the range in which the sequence is annealed to a particular sequence as well as a perfectly identical sequence.

As used herein, the term "induced pluripotent stem cells" refers to cells derived from differentiated cells to have the pluripotency through an artificial reprogramming process, and also is called reprogramming induced pluripotent stem cells. Induced pluripotent stem cells have almost the same characteristics as embryonic stem cells. Specifically, the induced pluripotent stem cells have a similar cell appearance, gene, and protein expression pattern, retain pluripotency in vitro and in vivo, and enables germline transmission of genes. The induced pluripotent stem cells of the present invention encompass reprogramming induced pluripotent stem cells originated from all mammals including human, monkey, pig, horse, cattle, sheep, dog, cat, mouse, and rabbit, but specifically, the induced pluripotent stem cells are human-derived induced pluripotent stem cells, and the most preferably, induced pluripotent stem cells derived from a hemophilia A patient.

As used herein, the term "reprogramming" refers to an epigenetic reverse process in which existing differentiated cells are returned to an undifferentiated state to enable the formation of new differentiated tissues, and is also referred to as a reprogramming process, and is based on the reversibility of epigenetic changes of the cell genome. According to a purpose of the present invention, the term "reprogramming" encompasses all processes as long as differentiated cells having differentiation potency of 0% or more but less than 100% are reverted to an undifferentiated state, and may encompass, for example, a process in which differentiated cells having differentiation potency of 0% are undifferentiated into differentiated cells having differentiation potency of 1%.

The reprogramming of the present invention may be carried out through various methods known in the art and capable of reverting differentiation potency of the already differentiated cells, and for example, the reprogramming was achieved by transfecting somatic cells isolated from the hemophilia A patient with at least one gene selected from the group consisting of OCT4, NANOG, SOX2, LIN28, KLF4, and c-MYC.

The medium used to culture human somatic cells to obtain induced pluripotent stem cells encompasses any ordinary medium. Examples thereof may include Eagles's MEM (Eagle's minimum essential medium, Eagle, H. Science 130:432(1959)), α-MEM (Stanner, C. P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med., 73:1(1950)), CMRL 1066, RPMI 1640(Moore et al., J. Amer. Med. Assoc. 199:519(1967)), F12 (Ham, Proc. Natl. Acad. Sci. USA 53:288(1965)), F10 (Ham, R.G. Exp. Cell Res. 29:515(1963)), DMEM (Dulbecco's modification of Eagle's medium, Dulbecco, R. et al., Virology 8:396(1959)), a mixture of DMEM and F12 (Barnes, D. et al., Anal. Biochem. 102:255(1980)), Waymouth's MB752/1 (Waymouth, C. J. Natl. Cancer Inst. 22:1003(1959)), McCoy's 5A (McCoy, T. A., et al., Proc. Soc. Exp. Biol. Med. 100:115(1959)) and MCDB series (Ham, R. G. et al., In Vitro 14:11(1978)), but are not limited thereto.

As used herein, the term "gene delivery system" refers to a medium for introducing a desired target gene into a target cell to express the target gene. An ideal gene delivery system is harmless to a human body or cells and easy to mass-produce, and must deliver a gene efficiently.

As used herein, the term "gene delivery" refers to the delivery of a gene into a cell, and has the same meaning as the intracellular transduction of a gene. At the tissue level, the term "gene delivery" has the same meaning as the spread of a gene. Therefore, the gene delivery system of the present invention may be described as a gene transduction system and a gene spreading system.

In order to produce the gene delivery system of the present invention, the nucleotide sequence of the present invention is preferably present in a suitable expression construct. In the expression construct, the nucleotide sequence of the present invention is preferably operatively linked to a promoter. As used herein, the term "operatively linked" refers to a functional linkage between a nucleic acid expression regulatory sequence (e.g., a promoter, a signal sequence, or an array of transcription regulation factor binding sites) and another nucleic acid sequence, and through the linkage, the regulatory sequence regulates the transcription and/or translation of the another nucleic acid sequence. In the present invention, the promoter binding to the polynucleotide sequence is one that can regulate the transcription of the relaxin gene by operating in animal cells, preferably mammals, and more preferably human cells, and includes, for example, promoters derived from mammalian viruses and promoters derived from mammalian cell genomes. Examples thereof may include cytomegalovirus (CMV) promoter, adenovirus late promoter, vaccinia virus 7.5K promoter, SV40 promoter, U6 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, and human GM-CSF gene promoter, but are not limited thereto. Most preferably, the promoter used in the present invention is CMV promoter and/or U6 promoter.

The gene delivery system of the present invention may be constructed in various forms, and the gene delivery system may be constructed in a form of: (i) naked recombinant DNA molecule, (ii) plasmid, (iii) viral vector, and (iv) liposome or niosome including the naked recombinant DNA molecule or plasmid.

The nucleotide sequence of the present invention may be applied to all gene delivery systems used in ordinary animal transfection, and may be preferably applied to plasmid, adenovirus (Lockett L J, et al., Clin. Cancer Res. 3:2075-2080(1997)), adeno-associated viruse (AAV, Lashford L S., et al., Gene Therapy Technologies, Applications and Regulations Ed. A. Meager, 1999), retrovirus (Gunzburg W H, et al., Retroviral vectors. Gene Therapy Technologies, Applications and Regulations Ed. A. Meager, 1999), lentivirus (Wang G. et al., J. Clin. Invest. 104(11):R55-62(1999)), herpes simplex virus (Chamber R., et al., Proc. Natl. Act. Sci USA92:1411-1415(1995)), vaccinia virus (Puhlmann M. et al., Human Gene Therapy 10:649-657(1999)), liposome (Methods in Molecular Biology, Vol 199, S.C. Basu and M. Basu (Eds.), Human Press 2002) or niosome. Most specifically, the gene delivery system of the present invention is plasmid.

In the present invention, when the gene delivery system is constructed on the basis of a viral vector, the contacting step is carried out by a viral infection method known in the art.

The infection of host cells using viral vectors are described in the above-mentioned cited documents.

When the gene delivery system in the present invention is a naked recombinant DNA molecule or a plasmid, a gene may be introduced into a cell by micro-injection (Capecchi, M. R., Cell, 22:479(1980); and Harland & Weintraub, J. Cell Biol. 101:1094-1099(1985)), calcium phosphate precipitation (Graham, F. L. et al., Virology, 52:456(1973); and Chen & Okayama, Mol. Cell. Biol. 7:2745-2752(1987)), electroporation (Neumann, E. et al., EMBO J., 1:841(1982); and Tur-Kaspa et al., Mol. Cell Biol., 6:716-718(1986)), liposome-mediated transfection (Wong, T. K. et al., Gene, 10:87(1980); Nicolau and Sene, Biochim. Biophys. Acta, 721:185-190(1982); and Nicolau et al., Methods Enzymol., 149:157-176(1987)), DEAE-dextran treatment (Gopal, Mol. Cell Biol., 5:1188-1190(1985)), and gene bombardment (Yang et al., Proc. Natl. Acad. Sci., 87:9568-9572(1990)), and most specifically, electroporation may be used.

Hemophilia A to be treated in the present invention is severe hemophilia A. As used herein, the term "severe hemophilia A" means a case in which the activity of blood coagulation factor VIII (F8) is less than 1% compared with a normal person.

As used herein, the term "treatment" refers to: (a) suppressing the development of disease, disorder, or symptom; (b) reducing disease, disorder, or symptom; or (c) removing disease, disorder, or symptom. The composition of the present invention serves to suppress, remove, or reduce the development of symptoms that have been caused due to gene inversions by expressing the gene which is corrected in a subject with hemophilia A and is the same as that of a wild type. Therefore, the composition per se of the present invention may be a composition for treating hemophilia A, and may be applied as a treatment adjuvant for the disease by being administered together with another pharmaceutical ingredient. Therefore, as used herein, the term "treatment" (or "therapy") or "treatment agent" (or "therapeutic agent") includes the meaning of "treatment aid" (or "therapy aid") or "treatment adjuvant" (or "therapeutic adjuvant").

As used herein, the term "administration" or "administer" refers to the direct application of a therapeutically effective amount of the composition of the present invention to a subject, to thereby form the same amount thereof in the body of the subject. Therefore, the term "administer" encompasses an injection or transplantation of induced pluripotent stem cells or adult cells obtained from redistribution of the induced pluripotent stem cells, and thus, the term "administer" is used in the same meaning as "inject" or "transplant".

The term "therapeutically effective amount" of the composition refers to the content of an extract, which is sufficient to provide a therapeutic or prophylactic effect to a subject to be administered, and thus the term has a meaning including "prophylactically effective amount". As used herein, the term "subject" includes, but is not limited to, human, mouse, rat, guinea pig, dog, cat, horse, cow, pig, monkey, chimpanzee, beaver, or rhesus monkey. Specifically, the subject of the present invention is human.

In cases where the composition of the present invention is prepared into a pharmaceutical composition, the pharmaceutical composition of the present invention contains a pharmaceutically acceptable carrier. The pharmaceutically acceptable carrier contained in the pharmaceutical composition of the present invention is one that is conventionally used in the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, saline, phosphate buffered saline (PBS), and media.

The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in Remington's Pharmaceutical Sciences (19th ed., 1995).

The pharmaceutical composition of the present invention may be administered parenterally, and specifically, through intravascular administration.

A suitable dose of the pharmaceutical composition of the present invention may vary depending on various factors, such as a method for formulation, manner of administration, age, body weight, gender, morbidity of a patient, diet, time of administration, route of administration, excretion rate, and response sensitivity. The general dose of the pharmaceutical composition of the present invention is $10^2$-$10^{10}$ cells per day on the basis of an adult.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, a syrup, or an emulsion, an extract, a pulvis, a powder, a granule, a tablet, or a capsule, and may further include a dispersant or a stabilizer.

Advantageous Effects

The features and advantages of the present invention are summarized as follows:

(a) The present invention provides a method for inducing an inversion of the normal blood coagulation factor VIII (F8) gene, a method for correcting an inversion of the inverted blood coagulation factor VIII (F8) gene, and inversion-corrected, hemophilia A patient-derived induced pluripotent stem cells prepared by using the same.

(b) The method of the present invention can be favorably used as a research tool for research on the pathogenesis of hemophilia A and screening of therapeutic agents by efficiently reproducing the inversions of intron 1 and intron 22 of the F8 gene.

(c) The inversion-corrected induced pluripotent stem cells prepared by the method of the present invention enable efficient and fundamental therapy for hemophilia A by the reversion of the mutated genotype to the same state as in a wild type, not by a restrictive method through the delivery of normal genes or proteins.

BRIEF DESCRIPTION OF THE DRAWINGS

FIG. 1a shows results in which genomic DNA was isolated from human dermal fibroblasts (WT) and hemophilia A patient-derived urine cells (Pa1, Pa2, and Pa3) and subjected to PCR analysis using appropriate primers (Bagnall et al., 2006) to detect intron 1 (left) or 22 (right) inversions. FIG. 1b is a schematic view showing intron 22 inversion and reversion. Three homolog regions are represented as int22h-1, int22h-2, and int22h-3, respectively. Blue arrowheads indicate PCR primers. Nuclease target sites near int22h-1 or int22h-3 are indicated by black (RGEN 02) or red (RGEN 03) lightning symbols. FIG. 1c shows results in which mutations at nuclease target sites in HeLa cells were confirmed by the T7E1 assay. FIG. 1d shows PCR products corresponding to the inversion of the 563-kbp chromosomal segment in HeLa cells. FIG. 1e shows PCR analysis results to confirm the inversion correction in iPSC clones. FIG. 1f shows DNA sequences of breakpoint junctions in the inversion-corrected iPSC clones. Each RGEN target sequence is underlined; the PAM sequence is shown in green; and dashes indicate deleted bases. Lowercase letters indicate inserted bases, and blue arrows indicate cleavage sites.

FIG. 2a shows quantitative real-time PCR (qPCR) results to detect endogenous OCT4, SOX2, LIN28, and NANOG mRNAs from parental and corrected cell lines. The expression level of each gene was normalized through GAPDH. FIG. 2b shows the in vitro differentiation of inversion-corrected lines. The expressions of the respective marker proteins represent the differentiation into the ectoderm (Nestin), mesoderm [α-smooth muscle actin [α-SMA]), and endoderm (α-fetoprotein [AFP]). Scale bar, 50 mm. FIG. 2c shows results in which the expression of OCT4 and SSEA4, human-ESC-specific markers, was detected by immunocytochemistry. Scale bar, 100 mm. Karyotypes of the iPSC lines are shown together. FIG. 2d is a view showing the F8 gene expression in cells differentiated from intron 1 and 22 inversion-corrected iPSC lines. RT-PCR (upper) and qPCR (lower) was used to detect the expression of F8 and a mesoderm marker gene (Brachyury) in cells derived from wild type iPSCs (WT), patient iPSCs (Pa1, Pa2, and Pa3), and inversion-corrected Pa1- (Co-1 and Co-2), or Pa2-iPSCs (Co-1, Co-2, and Co-3). GAPDH expression was used as a loading control. FIG. 2e shows chromatograms illustrating correct splicing between exons 1 and 2 or exons 22 and 23 in inversion-corrected iPSC lines.

FIGS. 3a to 3f are views showing correction of intron 1 inversion in hemophilia A patient-derived iPSCs. FIG. 3a is a schematic diagram showing a process in which the intron 1 inversion found in a severe hemophilia A patient is corrected. Blue arrowheads indicate PCR primers. FIG. 3b shows results in which the mutation frequency of RGEN 01 target sites in intro 1 of the F8 gene in HeLa cells. FIG. 3c is a view showing PCR products corresponding to the inversion genotype of HeLa cells. FIG. 3d is a diagram showing DNA sequences of two intron 1 homologs (named int1 homologs 1 and 2) and breakpoint junctions. Genome DNA was isolated from HeLa cells transfected with RGEN-encoding plasmids and inversion-specific PCR bands were separated, and then two breakpoint junctions were sequenced. RGEN target sequences are underlined; PAM sequences are shown in green; and dashes indicate deleted bases. Lowercase letters indicate inserted bases. FIG. 3e shows genome DNA PCR analysis results of four corrected clones (Co-1 to Co-4). Genomic DNA was isolated from urine-derived cells of an intron 1 inversion patient (Pa1-U) and wild-type iPSC (WT), which is a positive control for the inversion or normal genotype. FIG. 3f shows DNA sequences of two intron 1 homologs (named int1 homologs 1 and 2) and breakpoint junctions. Genomic DNA was isolated from iPSCs transfected with an RGEN-encoding plasmid. Reversion-specific PCR bands were separated, and two breakpoint junctions were sequenced. RGEN target sequences are underlined; PAM sequences are shown in green; and dashes indicate deleted bases.

FIG. 4a shows DNA sequences of two breakpoint junctions for inversion in HeLa cells. RGEN target sequences are underlined; PAM sequences are shown in green; and dashes indicate deleted bases. Lowercase letters indicate inserted bases, and blue arrows indicate cleavage sites. FIGS. 4b and 4c shows DNA sequences of breakpoint junctions in intron 1 (4b) and intron 22 (4c) regions, respectively. RGEN RNP was delivered directly to intron 1 (Pa1-iPSCs) or intron 22 (Pa3-iPSCs) inverted cells through electroporation. Total DNA was isolated from iPSCs, and then sequenced. RGEN target sequences are underlined; PAM sequences are shown in green; and dashes indicate deleted bases. Lowercase letters indicate inserted bases, and two blue arrows indicate cleavage sites. The number detected is indicated by the number in parentheses when the sequence is detected at least one.

FIGS. 7a to 7b show TALEN-mediated inversion of the F8 locus in iPSCs. (7a) PCR analysis of genomic DNA from four inversion clones. Genomic DNA samples isolated from hemophilia A patient cells (Pa) or wild-type iPSCs (WT) served as positive controls for the inversion or normal genotypes, respectively. (7b) DNA sequences of breakpoint junctions in inversion clones. TALEN binding sites are shown in red (homolog 1) or blue (homolog 2).

FIGS. 8a to 8c show reversions of the F8 gene inversion. (8a) PCR analysis is of genomic DNA from three reverted clones. Genomic DNAs isolated from hemophilia A patient cells (Pa) or wild-type iPSCs (WT) served as positive controls for inversion or normal genotypes, respectively. (8b) DNA sequences of breakpoint junctions in reverted clones. TALEN binding sites are shown in red (junction 1) or blue (junction 2). Dashes indicate deleted bases. (8c) The chromatograms show the sequences (of homolog 1 and 2, respectively) between two TALEN binding sites in reverted clones (clones 1 and 3).

FIGS. 11a to 11b show frequencies of targeted inversions. (A) The frequency of targeted inversions was estimated by digital PCR. Genomic DNA samples isolated from cells transfected with transcription activator-like effector nuclease (TALEN)-encoding plasmids were serially diluted and subjected to digital PCR analysis. (11b) Estimated frequencies of targeted chromosomal inversions created via zinc-finger nucleases (ZFNs) or TALENs. Z10 is a ZFN pair targeting the intron1 homolog of the F8 gene. The frequency of 140-kbp inversion events was measured by digital PCR analysis. Upper and lower limits indicate 95% confidence intervals.

MODE FOR CARRYING OUT THE INVENTION

Figure 1A:
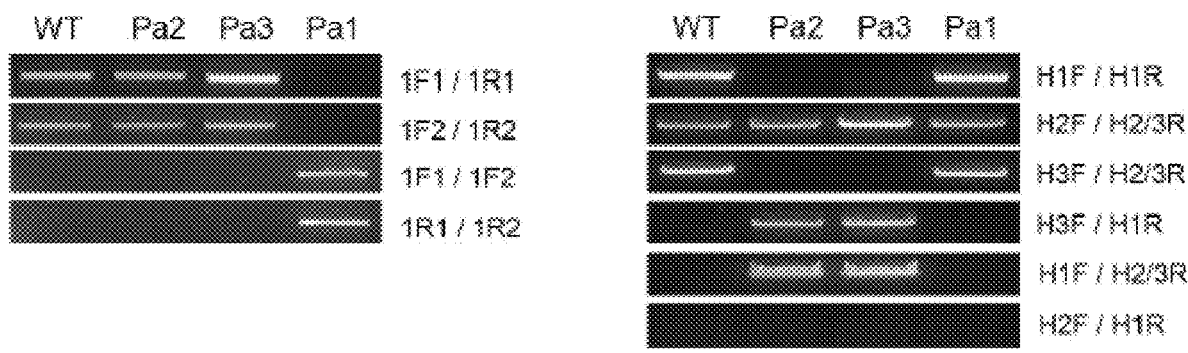
FIGS. 1a to 1f are views showing correction results of the partially-inverted F8 gene in hemophilia A patient-derived iPSCs.

Hereinafter, the present invention will be described in detail with reference to examples. These examples are only for illustrating the present invention more specifically, and it will be apparent to those skilled in the art that the scope of the present invention is not limited by these examples.

Example 1: RNA-Guided Engineered Nuclease (RGEN)

Methods

Analyses of urine-derived iPSCs from hemophilia A patients according to the present invention was made under the approval of the Yonsei University Institutional Review Board (IRB #4-2012-0028). All volunteers signed written informed consent forms before donating urine samples for human iPSC generation.

Cell Culture and Transfection

HeLa cells (ATCC, CCL-2) were cultured in Dulbecco's modified Eagle's medium (DEME) supplemented with 10% fetal bovine serum (FBS), 0.1 mM nonessential amino acids, and 1% antibiotics. To induce DSB, $1 \times 10^5$ HeLa cells were co-transfected with Cas9-encoding plasmid and sgRNA-encoding plasmid (0.5 mg each) using a Lipofectamine 2000 transfection reagent (Invitrogen) according to the manufacturer's protocol. Human ESC (hESC) lines (H9) obtained from WiCell Inc, human dermal fibroblast-derived wild-type iPSCs (WT-iPSC Epi3 line) (Park et al., 2014), and urine-derived iPSCs were maintained together with 4 ng/mL basic fibroblast growth factor (bFGF, PeproTech) in hESC medium [DMEM/F12 medium supplemented with 20% knockout serum replacement (Gibco), 1% nonessential amino acids, and 0.1 mM 2-mercaptoethanol (Sigma)]. To induce reversions in urine-derived iPSCs, $1 \times 10^6$ cells were electroporated with 5 μg Cas9-encoding plasmid and 5 μg of sgRNA-encoding plasmid (5 μg of each sgRNA plasmid for the intron 22 inversion) using a microporator system (Neon; Invitrogen).

For direct delivery of Cas9 protein into the urine-derived iPSCs, transfection was performed by the previously reported method (Kim et al., 2014) with slight modifications. Cas9 protein (15 μg) was mixed with 20 μg of transcribed sgRNA (20 μg of each sgRNA plasmid for the intron 22 inversion), and incubated for 10 min at room temperature to form RGEN ribonucleoproteins (RNPs). The RNPs were transfected into $2 \times 10^5$ iPSCs by using a microporator system.

Isolation and Expansion of Urine-Derived Cells from Severe Hemophilia a Patients Urine samples were collected from 11 patients diagnosed with severe hemophilia A, and this diagnose had been clinically confirmed by the Korea Hemophilia Foundation Clinic. Urine-derived cells were isolated by the previously reported method (Zhou et al., 2012). In brief, cells were collected from approximately 100 ml of midstream urine sample by centrifugation at 400 g for 10 min. After washing twice with PBS, the cells were cultured in DMEM/Ham's F12 (1:1) medium (Hyclone) supplemented with 10% (vol/vol) FBS, renal epithelial cell growth medium (REGM, obtained from the SingleQuot kit (Lonza)), and 1% antibiotics. After four days of culture under these conditions, the cells were cultured in REGM (Lonza) to expand the cells. The cells were split onto gelatin-coated culture dishes at 80-90% confluency. To confirm the F8 genotype, genomic DNA samples isolated from urine-derived patient cells were subjected to PCR analysis with primer sets recognizing appropriate regions near the intron 1 and 22 inversions of the F8 locus (Bagnall et al., 2006; Park et al., 2014.

RGEN Composition

Cas9-encoding plasmids were constructed by the previously reported method (Cho et al., 2013). Cas9 protein fused to the HA epitope and a nuclear localization signal (NLS) was expressed under the CMV promoter. The U6 promoter was used in sgRNA expression (Cho et al., 2014). Purified recombinant Cas9 protein was purchased from ToolGen, Inc. Guiding RNA was transcribed in vitro using the MEGAshortscript T7 kit (Ambion) by the previously reported method (Kim et al., 2014). Transcribed RNA was purified by phenol:chloroform extraction, and quantified using a spectrometer.

T7E1 Assay and Determination of Targeted Inversion Frequencies

The T7E1 assay was performed according to the previously reported method (Kim et al., 2009). In brief, PCR amplicons including the RGEN target sites were denatured by heating and annealed to form heteroduplex DNA fragments. The fragments were then treated with T7 endonuclease (New England Biolabs) for 20 min at 37° C. to allow cutting at mismatched sites, and the products were analyzed by agarose gel electrophoresis. The frequencies of targeted corrections at the F8 locus were estimated through digital PCR analysis by the previously reported method (Kim et al., 2010). Genomic DNA isolated from the cells were co-transfected with RGEN and sgRNA plasmids using the lipofectamine 2000 transfection reagent (Invitrogen) was serially diluted, and the diluted samples were subjected to PCR analysis. The fraction of positive bands at each dilution point was determined and the results were analyzed using the Extreme Limiting Dilution Analysis program (Hu and Smyth, 2009).

Validation of RGEN-Mediated Inversion of the F8 Locus in HeLa Cells

To validate the genome editing activities of the RGENs designed in the present invention, each RGEN was co-transfected with a sgRNA expression plasmid into HeLa cells. RGEN activity was measured using the T7E1 assay as described above.

Targeted RGEN-Mediated Correction of the F8 Locus in Patient-Derived iPSCs iPSCs were cultured on a STO cell support layer and harvested by treating with collagenase type IV. After washing with PBS, the cells were dissociated into single cells by the previously reported method (Desbordes et al., 2008). These single cells were mixed with RGEN and sgRNA plasmids, and pulsed with a voltage of 850 for 30 ms. Cells were then seeded onto support cells and allowed to grow for 10 days. To detect genomic inversion occurring at the F8 locus, cells from individual colonies were lysed and subjected to PCR, and PCR products were analyzed. The used primers are as follows::1-F1: 5'-AAATCACC-CAAGGAAGCACA-3' (SEQ ID NO: 5), 1-R1: 5'-TGG-CATTAACGTATTACTTGGAGA-3' (SEQ ID NO: 6); 1-F2: 5'-GGCAGGGATCTTGTTGGTAAA-3' (SEQ ID NO: 7), 1-R2: 5'-TGCTGAGCTAGCAGGTTTAATG-3' (SEQ ID NO: 8); 22-F1: 5'-TGGGGCTGTGTAAAT-TTGCT-3' (SEQ ID NO: 9), 22-R2: 5'-CAAACGTAGCAT-TACCTGATTGT-3' (SEQ ID NO: 10); 22-F2: 5'-ACAACCAGAG CAGAAATCAATGA-3' (SEQ ID NO:11), 22-R2: 5'-TTTCACCACATCCACGCCAA-3' (SEQ ID NO:12).

Establishment and Characterization of Clonal Cell Populations

To isolate clonal populations of corrected cells, each colony that had been identified by PCR as having desired genomic modifications (namely, correction of the inversion genotype) was dissociated into single cells, and re-seeded onto a new cell support layer. After 4 rounds of passage, several clones (4 clones for the intron 1 correction, 3 clones for the intron 22 correction) were chosen for sequencing and further experiments. For sequence analysis at the breakpoints, amplified PCR products were electrophoresed, and eluted from the agarose gel.

RNA Isolation, RT-PCR, and qPCR

Total RNAs were purified using TRIzol reagent (Invitrogen) according to the manufacturer's instructions. cDNAs were synthesized from total RNAs (1 μg) using the DiaStarTM cDNA synthesis kit (SolGent, Korea). To confirm the expression of Factor VIII, Brachyury, and GAPDH, PCR was performed with Ex-Taq (Takara) using the synthesized cDNAs as template. For qPCR, SYBRPremix Ex-Taq(Takara) was used according to the manufacturer's instructions. To amplify F8 mRNA from intron 1 or intron 22 corrected lines, respectively, a forward primer located in exon 1 (or exon 21 for intron 22 corrected lines) was used together with a reverse primer located in exon 3 (or exon 23 for intron 22 corrected lines). RT-PCR or qPCR was performed using the following primer sets: GAPDH-F: 5'-CCCCTCAAGGG-CATCCTGGGCTA-3' (SEQ ID NO: 13), GAPDH-R: 5'-GAGGTCCACCACCCTGTTGCTGTA-3' (SEQ ID NO: 14); OCT4-F: 5'-CCTCACTTCACTGCACTGTA-3' (SEQ ID NO: 15), OCT4-R: 5'-CAGGTTTTCTTTCCCTAGCT-3' (SEQ ID NO: 16); LIN28-F: 5'-AGCCATATGGTAGCCT-CATGTCCGC-3' (SEQ ID NO. 17), LIN28-R: 5'-TCAAT-TCTGTGCCTCCGGGAGCAGGGTAGG-3' (SEQ ID NO: 18); SOX2-F: 5'-TTCACATGTCCCAGCACTACCAGA-3' (SEQ ID NO: 19), SOX2-R: 5'-TCACATGTGT-GAGAGGGGCAGTGTGC-3' (SEQ ID NO: 20); NANOG-F: 5'-TGAACCTCAGCTACAAACAG-3' (SEQ ID NO: 21), NANOG-R: 5'-TGGTGGTAGGAAGAGTAAAG-3' (SEQ ID NO: 22); F8-exon1-F: 5'-CTGCTTTAGTGC-CACCAGAAGA-3' (SEQ ID NO: 23), F8-exon3-R: 5'-GACTGACAGGATGGGAAGCC-3' (SEQ ID NO: 24); F8-exon21-F: 5'-CCGGATCAATCAATGCCTGGAG-3' (SEQ ID NO: 25), F8-exon23-R: 5'-AT-GAGTTGGGTGCAAACGGATG-3' (SEQ ID NO: 26); Brachyury-F: 5'-ATCACAAAGAGATGATGGAGGAA-3' (SEQ ID NO: 27), Brachyury-R: 5'-GGT-GAGTTGTCAGAATAGGTTGG-3') (SEQ ID NO: 28).

Generation and In Vitro Differentiation of Urine-Derived iPSCs

After three or fewer passages, iPSCs were generated from urine-derived cells. Episomal reprogramming vectors or Sendai virus (Invitrogen) were used to prepare iPSCs using urine-derived cells according to the previously reported method (Okita et al., 2011). Seven iPSC colonies that looked similar to human ES cells were picked up by a mechanical device, and were further cultured for characterization. The iPSCs were differentiated into three germ layers In vitro by a known method (Sugii et al., 2010). iPSC colonies were partially dissociated through collagenase type IV (Invitrogen) to induce the formation of embryoid bodies (EBs). EBs were transferred to Petri dishes (SPL Lifesciences, Korea) and cultured for 10 days in hESC medium lacking bFGF but supplemented with 5% FBS. Spontaneous differentiation of EBs into cells representing the three germ layers was detected through immunostaining using appropriate antibodies. To induce differentiation of iPSCs into the mesoderm lineage, the previously reported method was used with slight modifications (Yoo et al., 2013). Briefly, EBs were transferred to Petri dishes and cultured in hESC medium lacking bFGF but supplemented with 20 ng/mL bone morphogenic protein-4 (BMP4, R&D Systems) and 10 ng/mL activin A (PeproTech). At day 3, EBs were plated onto Matrigel-coated dishes and cultured for an additional 3 days in the medium described above. At day 6, the cells that had differentiated into the mesoderm lineage were harvested to check the expression of F8 gene.

Characterization of iPSCs

Alkaline phosphatase activity was determined using a leukocyte alkaline phosphatase staining kit (Sigma) according to the manufacturer's instructions. To confirm that the iPSC lines were generated from the urine-derived cells, short tandem repeats (STRs) were analyzed. STR loci were amplified from genomic DNA samples isolated from iPSC lines and their parental cells using the AmpFISTR PCR reaction system (Applied Biosystems). PCR-based STR analysis was performed at Human Pass Inc. (Korea). For karyotype analysis, G-banding analysis of chromosomes from each iPSC line was performed at GenDix Inc. (Korea). Immunostaining of ES cell markers was carried out by the previously reported method (Park et al., 2014). DAPI (4',6-diamidino-2-phenylindole, Vector Laboratories) was used for nuclei visualization, and the images were captured and analyzed using an Olympus IX71 microscope or FSX system.

Targeted Deep Sequencing

Genomic DNA segments encompassing nuclease target sites were amplified using Phusion polymerase (New England Biolabs). An equal amount of PCR amplicons were subjected to paired-end read sequencing using Illumina MiSeq. I around the RGEN cleavage site (PAMen3 bp upstream) was considered to be mutations induced by RGEN.

Whole Genome Sequencing

Genomic DNA was purified by the DNeasy Tissue kit (Qiagen) according to manufacturer's instructions. Genomic DNA (1 µg) was fragmented using a Covaris system and blunt ends were generated using End Repair Mix. Fragmented DNA was ligated with adapters to make libraries. Libraries were subjected to sequencing using IlluminaHiSeq X Ten sequencer at Macrogen (Korea).

Whole Genome Sequencing and Variant Information Extraction

FASTQ files obtained from the IlluminaHiSeq X Ten Sequencer were analyzed through an Isaac workflow from Illumina, Inc (USA). In brief, FASTQ files read by paired ends were aligned using according to the genome reference (hg19) Isaac Genome Alignment software (Isaac Aligner). Thereafter, single nucleotide polymorphism (SNP) and indels were identified by Isaac Variant Caller. Among millions of variants, the present inventors focused on indels because RGENs rarely induce substitutions. The bioinformatics filters were applied to exclude the indels registered in the public database and the indels extracted from other genomes. Next, the RGEN target sites were compared with wild-type loci corresponding to the indel locations. 31-106 indel sites included 5'-N(G/A)G-3'PAM sequence, and showed at least 12 nucleotide matches with respective on-target sequences. Finally, targeted deep sequencing was performed on 10 indel sites after discarding sites with repeat sequence.

Examination of Potential Off-Target Sites

To examine whether there were nuclease-induced indels at a lot of potential off-target sites in each genome sequence, the Cas-OFFinder was used to identify all the potential off-target sites that differed from on-target sites by up to 8 nucleotides or that differed by up to 2 nucleotides with a DNA or RNA bulge of 5 bases in length (Bae et al., 2014). An inner computer program was used to make a consensus CIGAR string that constituted 20% of total CIGAR strings at each potential off-target site. Next, the consensus CIGAR strings of a lot of potential off-target sites were compared with the CIGAR strings of the reference sequence. As a result, 83 to 348 potential off-target sites were obtained. Finally, targeted deep sequencing was performed on 4 indel sites that were observed in the independent clones and had no repeat sequences around the target sites.

Results

Figure 3A:
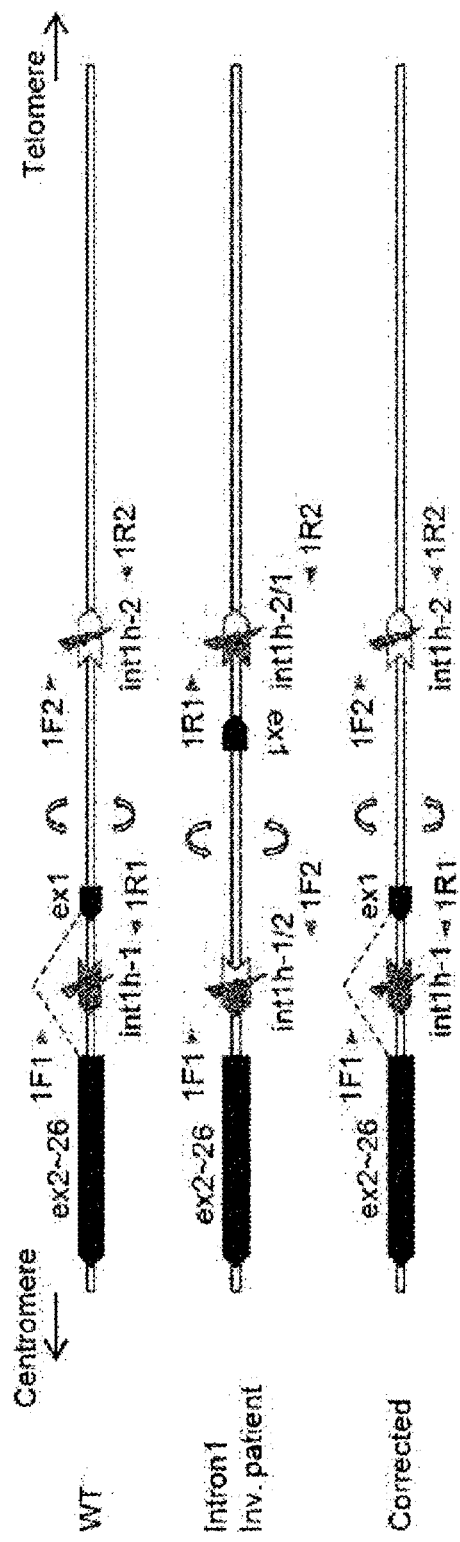
Figure 3B:
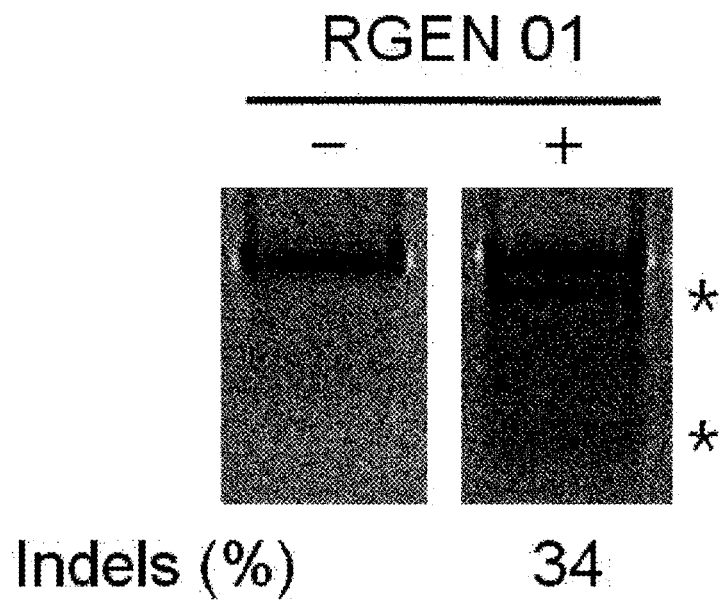
Figure 3C:
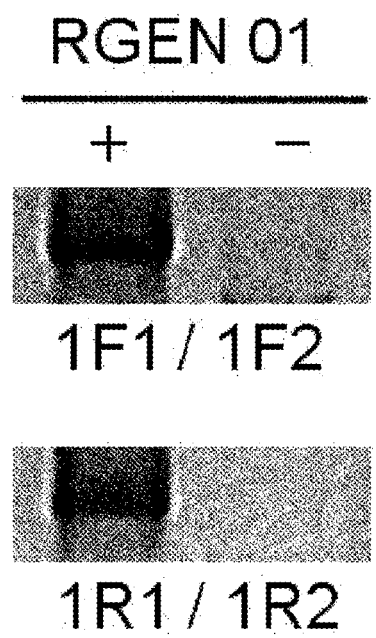

First, the present inventors analyzed the genotypes of 11 unrelated, severe hemophilia A patients and identified one patient with the int1 inversion and two patients with the int22 inversion. Therefore, the one patient with the int1 inversion (termed "Pa1") and two patients with the int22 inversion (termed "Pa2" and "Pa3") were chosen to carry out experiments (FIG. 1a). Respective iPSCs were established by introducing four Yamanaka factors into urinary epithelial cells via an episomal vector or Sendai virus, thereby obtaining fibroblasts from these patients with a bleeding disorder to avoid an invasive biopsy. Simultaneously, it was examined whether RGENs, which consisted of the Cas9 protein and small guide RNA (sgRNA), have activity to induce or revert their inversions in wild-type HeLa cells and patient iPSCs. RGEN 01 was designed to target a site in int1 h (FIG. 3a). RGEN 01 was highly active, inducing small insertions and deletions (indels) at a frequency of 34% at the target site in int1 h (FIG. 3b). In addition, RGEN 01 induced the inversion of the 140-kbp chromosomal segment in HeLa cells, as shown by inversion-specific PCR (FIG. 3c). The frequency of the inversion ranged from 2.2% to 3.1%, as measured by digital PCR (Kim et al., 2010; Lee et al., 2010).

Figure 3D:
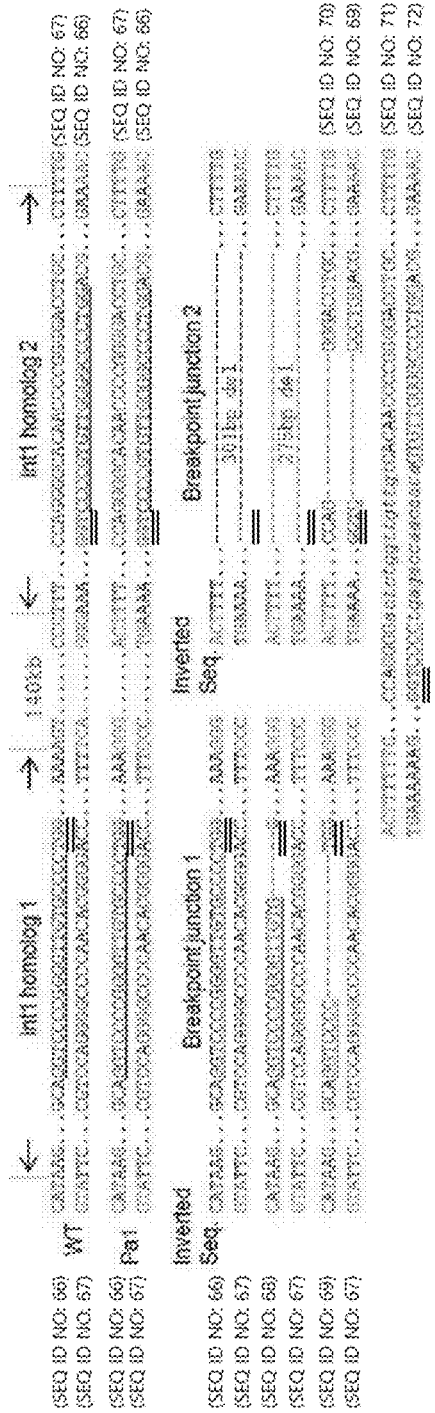

The present inventors, as a result of analyzing the DNA sequences of the inversion-specific PCR amplicons, found that indels were induced at the two inversion breakpoint junctions (FIG. 3d). Based on the high frequency, the present inventors co-transfected plasmids encoding the Cas9 protein and the sgRNA into Pa1-derived iPSCs (Pa1-iPSCs) and analyzed iPSC colonies using PCR. Eight colonies (not necessarily derived from single cells, 6.7%) out of 120 colonies produced positive PCR bands on an agarose gel.

Figure 3E:
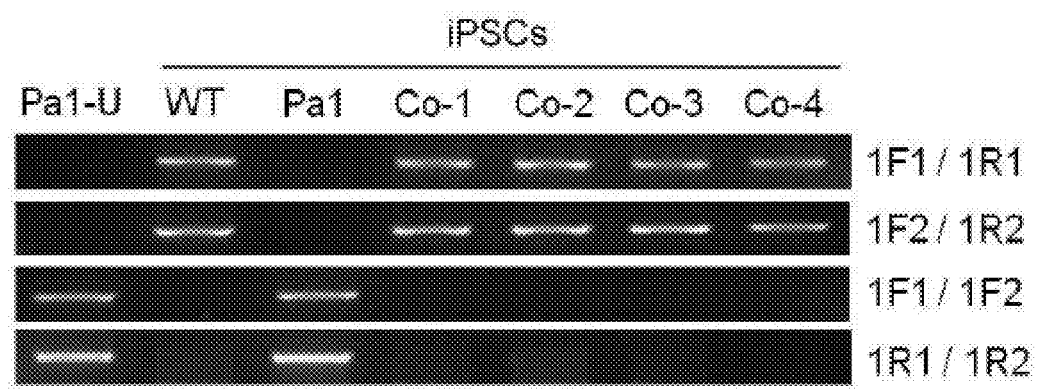
Figure 3F:
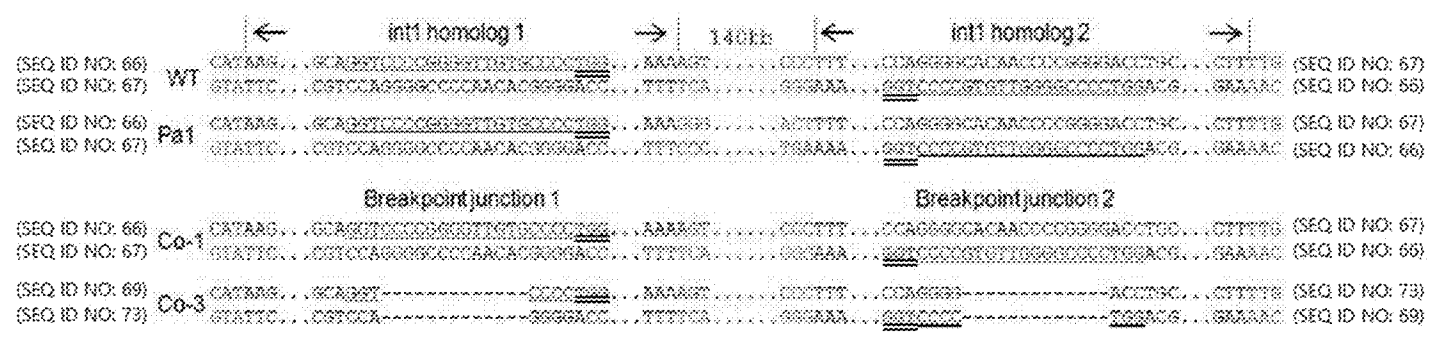

Four colonies were further cultured to obtain single-cell-derived clones. These clones produced PCR amplicons corresponding to the int1 h-1 and int1 h-2 regions, indicating that the inverted 140-kbp chromosomal segment in Pa1 cells was reverted (FIG. 3e).

In contrast, no PCR amplicons were produced from Pa1 iPSCs or urinary cells. The present inventors observed that no indels were induced at the target site in three clones by sequencing the PCR amplicons. In the other clone, there was a 13-bp deletion at the target site (FIG. 3d).

Figure 1B:
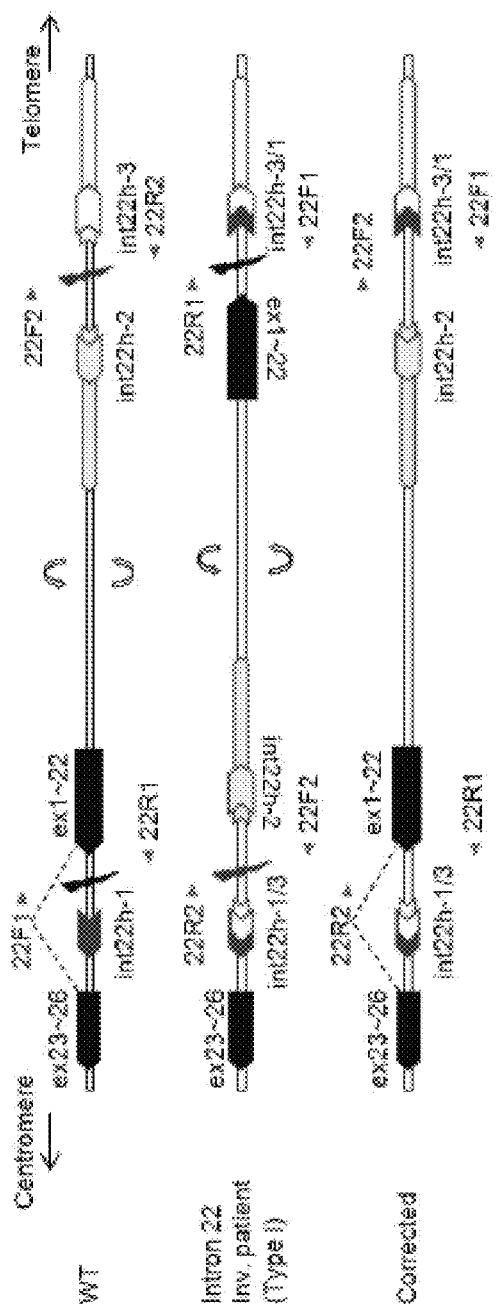
Figure 1C:
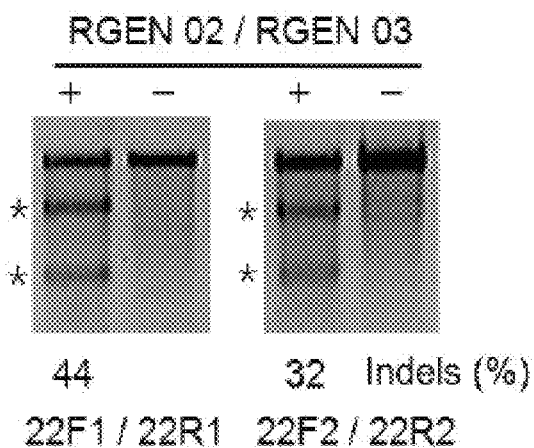
Figure 1D:
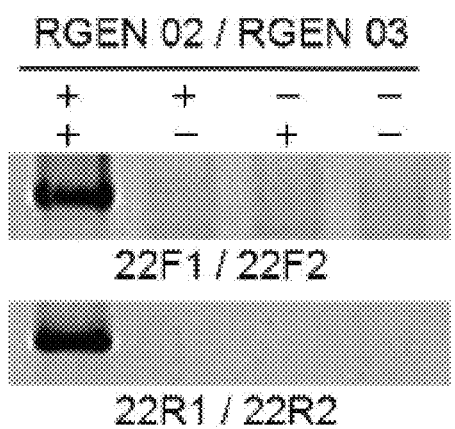
Figure 1E:
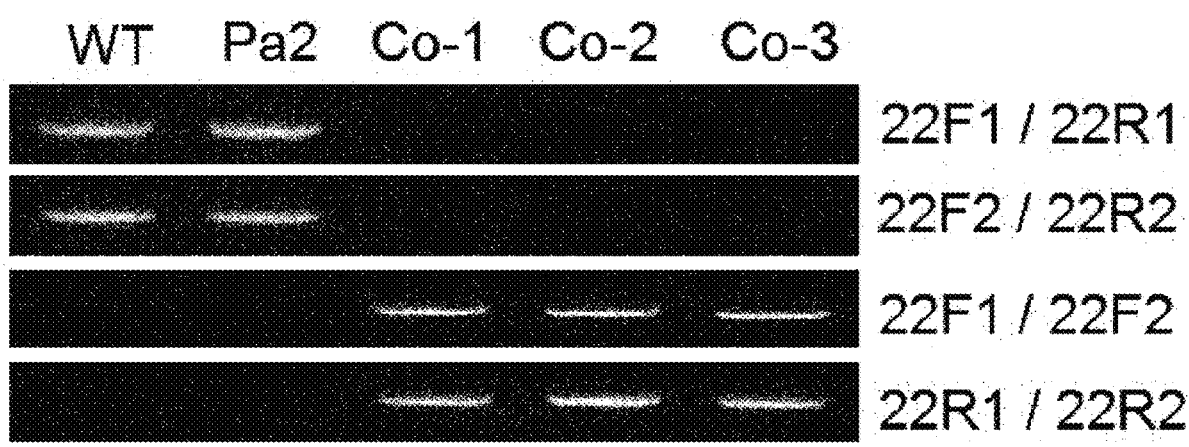

Then, the present inventors also focused on the other int22h inversion. To exclude the possibility that unwanted deletions or inversions involving two or three int22 homologs, rather than the desired reversion of the inverted 600-kbp segment, two RGENs that target sites outside of the homologs were used (FIG. 1b). This strategy also facilitates the detection of the reversion using appropriate PCR primers. The present inventors designed two RGENs (RGEN 02 and RGEN 03) to target sites near int22h-1 and int22h-3, and tested their nuclease activity in HeLa cells through the T7 endonuclease I (T7E1) assay. These RGENs were highly active, inducing indels at each target site with a frequency of 44% or 32% (FIG. 1c). Next, the inversion of the 563-kbp chromosomal segment between the two target sites was detected by PCR. Transfection of either RGEN 02 or RGEN 03 alone into HeLa cells did not produce inversion-specific PCR amplicons. In contrast, co-transfection of these RGEN plasmids gave rise to two inversion-specific PCR amplicons (FIG. 1d). The inversion frequency was in the range of 1.5% to 2.2% (Table 1).

TABLE 1

Frequencies of targeted inversions in HeLa cells

| | Amount of genomic DNA (Copy number per half genome) | | | | | Frequency (%) | | |
|---|---|---|---|---|---|---|---|---|
| | 1 ng | 333 pg (100) | 100 pg (30) | 33 pg (10) | 10 pg (3) | Estimated value | Upper and Lower limits | p value (Fit) |
| Int1h1 | 16/16 | 16/16 | 10/16 | 3/16 | 0/16 | 3.1 | (2.0-4.7) | 0.04 |
| Int1h2 | 16/16 | 15/16 | 7/16 | 3/16 | 0/16 | 2.2 | (1.4-3.3) | 0.24 |
| Int22 (junction1) | 16/16 | 13/16 | 8/16 | 6/16 | 0/16 | 2.2 | (1.4-3.3) | 0.43 |
| Int22 (junction3) | 16/16 | 13/16 | 6/16 | 0/16 | — | 1.5 | (1.0-2.3) | 0.13 |

* Upper and lower limits indicate 95% confidence intervals.

Figure 4A:
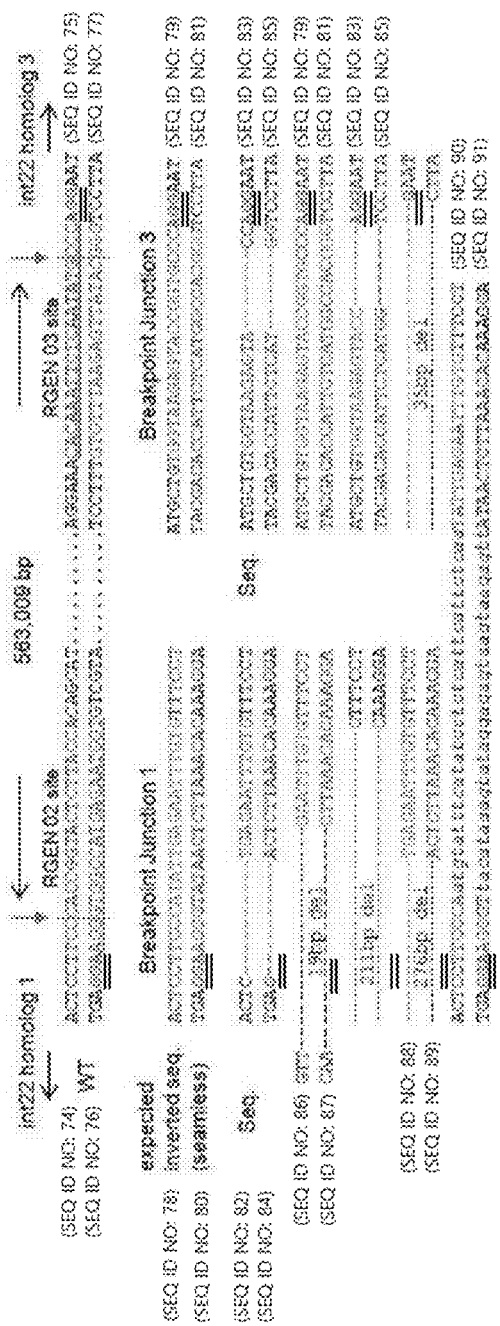
FIGS. 4a to 4c show targeted inversion and reversion in HeLa cells or patient iPCS.

As a result of determining the DNA sequences of the PCR amplicons, it was observed that most of indels accompanied the two inversion breakpoint junctions, indicating that two DSBs induced by the two RGENs were repaired by error-prone non-homologous end joining (NHEJ) (FIG. 4a). HeLa cells are wild type with respect to the F8 exon orientation. In Pa2 and Pa3 cells, F8 exons 1 to 22 are inverted. But still, the two RGEN target sites are conserved, enabling the reversion of the large chromosomal segment.

Figure 1F:
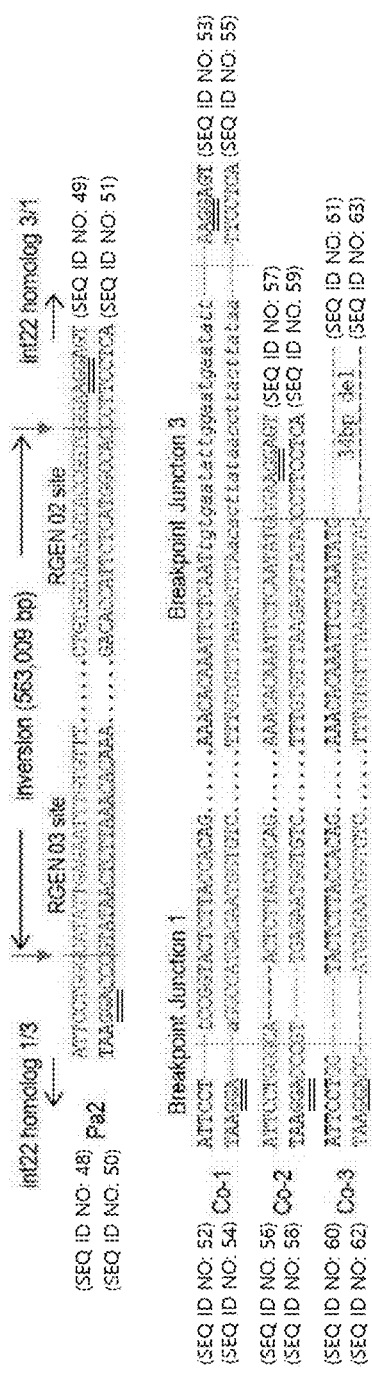

Next, RGEN 02 and 03 were transfected into Pa2 iPSCs through electroporation, and 135 colonies were isolated and subjected to PCR analysis for genomic DNA thereof. Five colonies (3.7%) yielded PCR amplicons corresponding to inversion-correction (namely, reversion). Such PCR products were not obtained in Pa2 iPSCs or wild type iPSCs. These colonies were further expanded to enable the isolation of three independent single-cell-derived clones. To confirm whether the 563-kbp chromosomal segment between the two RGEN sites was reverted, the DNA sequences at the two inversion breakpoint junctions were examined (FIG. 1f). As a result, like in HeLa cells, indels, which correspond to the characteristic of error-prone NHEJ, were observed at the two breakpoint junctions in these inversion-corrected iPSCs.

Figure 2A:
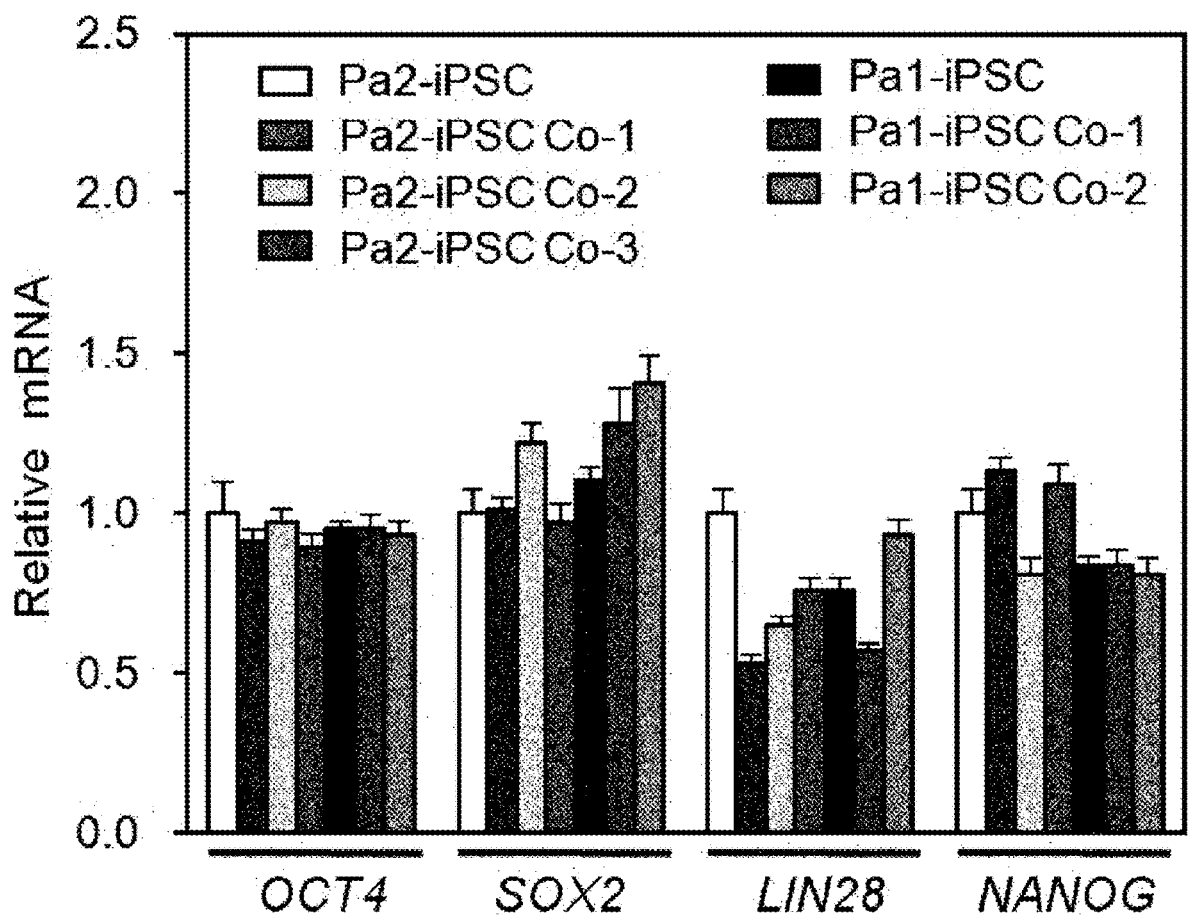
FIGS. 2a to 2e are views showing results of characterization of inversion-corrected iPSC Clones.
Figure 2B:
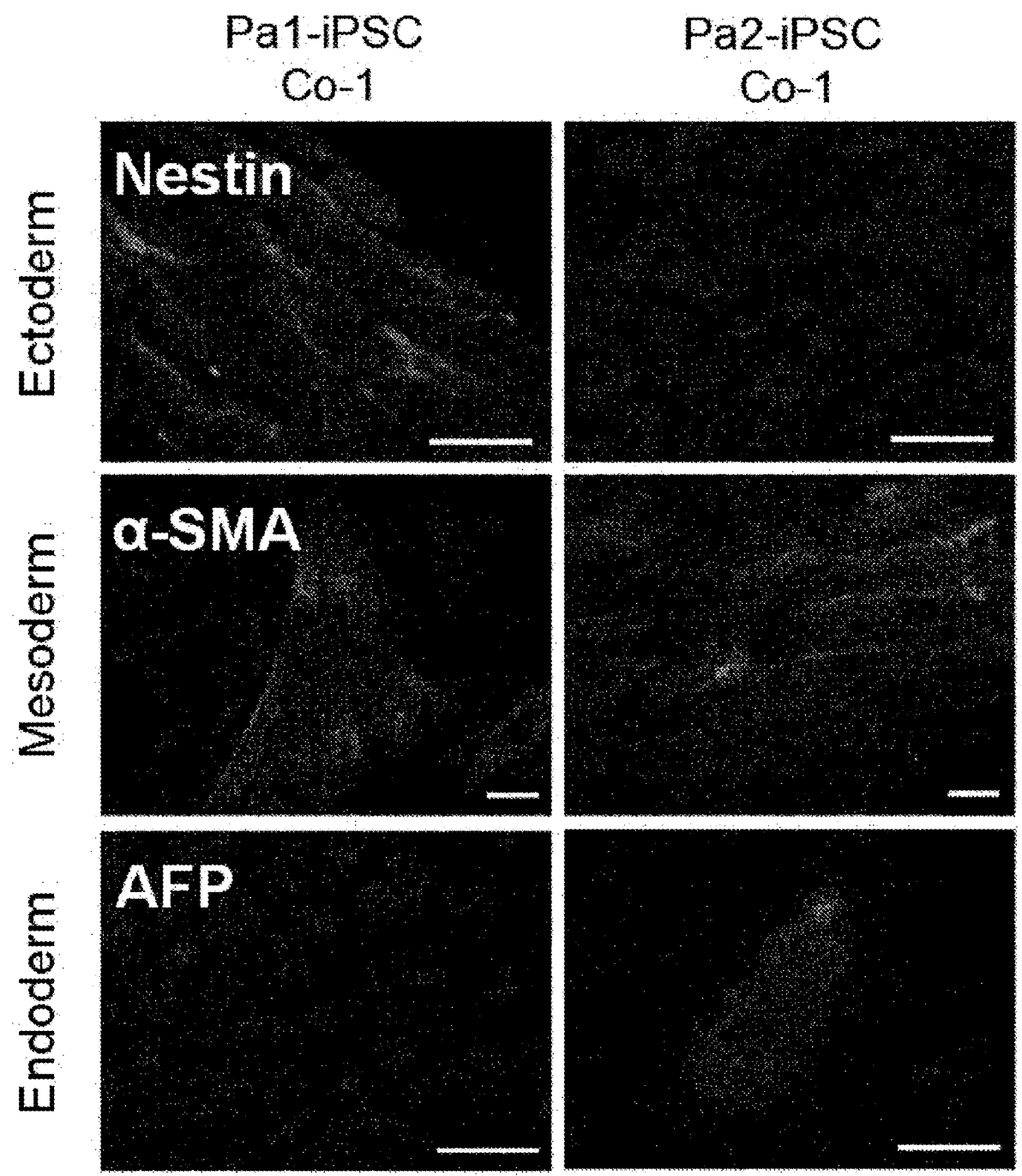
Figure 2C:
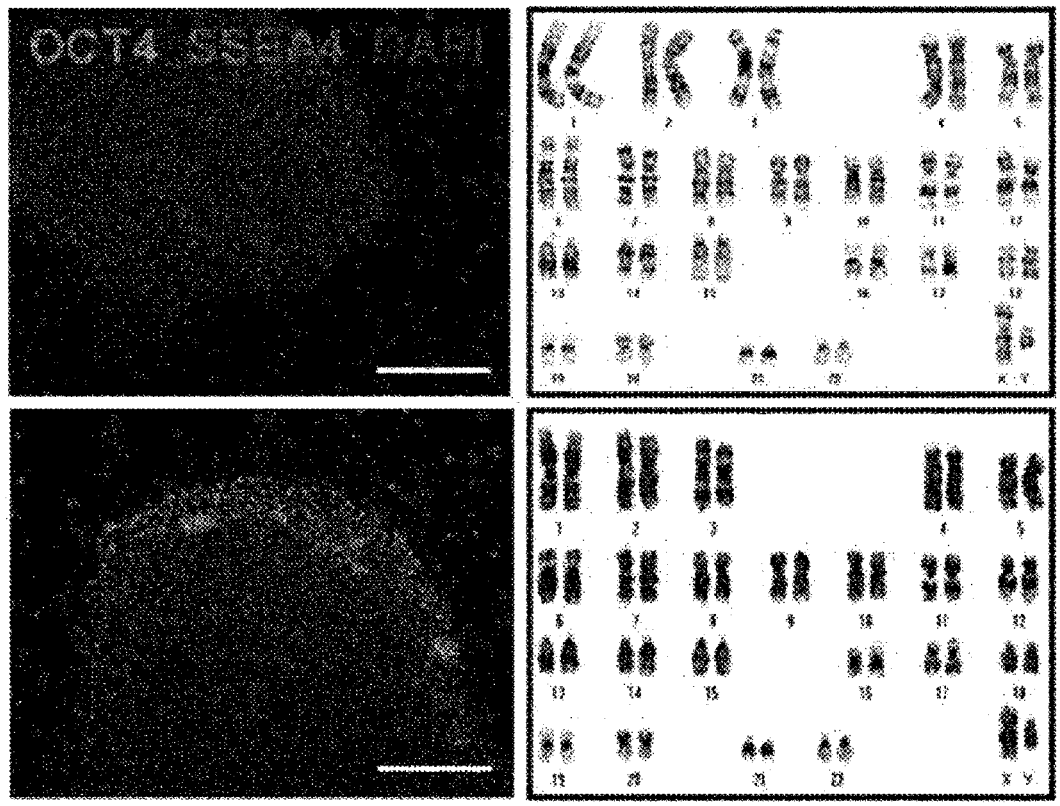

The present inventors investigated whether the inversion-corrected iPSCs retained pluripotency. First, as a result of investigating the expression of stem cell markers in inversion-corrected Pa1 (int1h inversion) and Pa2 (int22h inversion) iPSCs, it was found that OCT4, SOX2, LIN28, and NANOG, were actively transcribed (FIG. 2a). In addition, these inversion-corrected iPSCs were successfully differentiated into three primary germ layers (FIG. 2b), and furthermore, showed a normal karyotype (FIG. 2c). Taken together, it can be seen that th gross chromosomal reversions induced by RGENs do not negatively affect the pluripotency of patient-derived iPSCs.

Figure 2D:
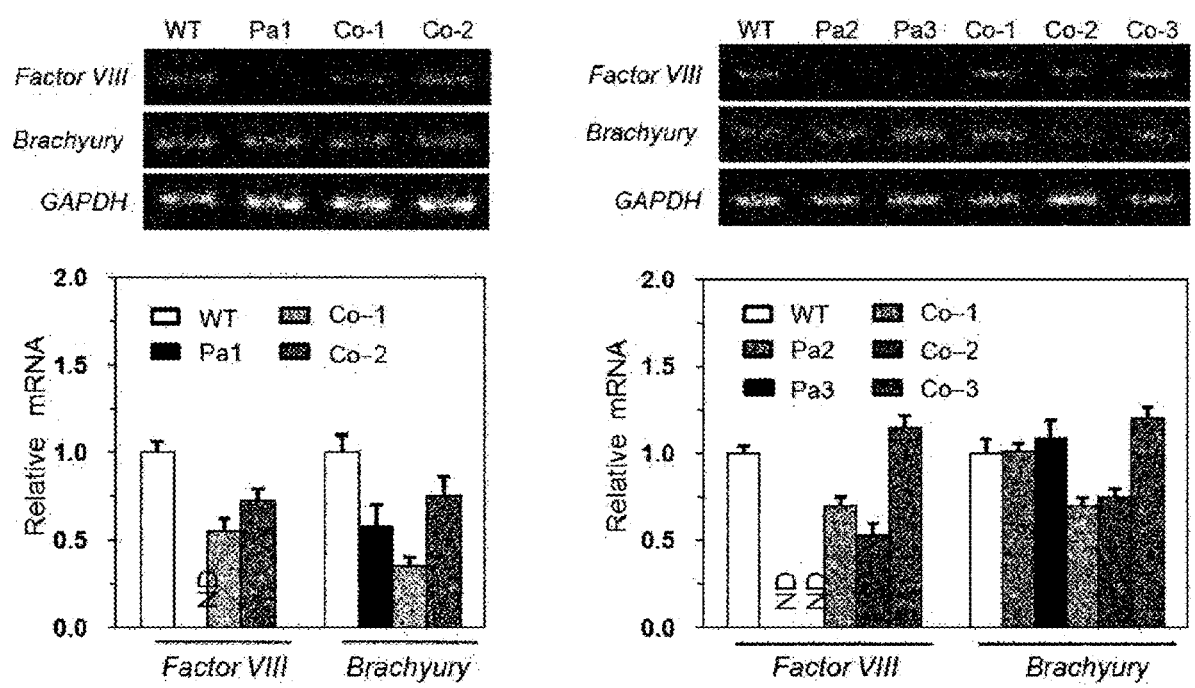

Endothelial cells derived from mesoderm are a major source of F8 gene expression (Shahani et al., 2010). The present inventors differentiated patient iPSCs and inversion-corrected patient iPSCs into mesoderm, and then measured the levels of F8 mRNA using RT-PCR. As expected, no PCR bands corresponding to F8 exons 1 and 2 were detected in cells differentiated from Pa1-iPSCs, indicating that F8 was not expressed in patient-derived cells (FIG. 2d). In contrast, PCR bands corresponding to these exons were detected in cells differentiated from the wild type iPSCs or the two inversion-corrected Pa1-iPSCs (Co-1 and Co-2). Likewise, PCR amplicons corresponding to F8 exons 22 and 23 were not detected in cells differentiated from Pa2- and Pa3-iPSCs, but were detected in cells differentiated from the three inversion-corrected iPSCs (FIG. 2d).

Figure 2E:
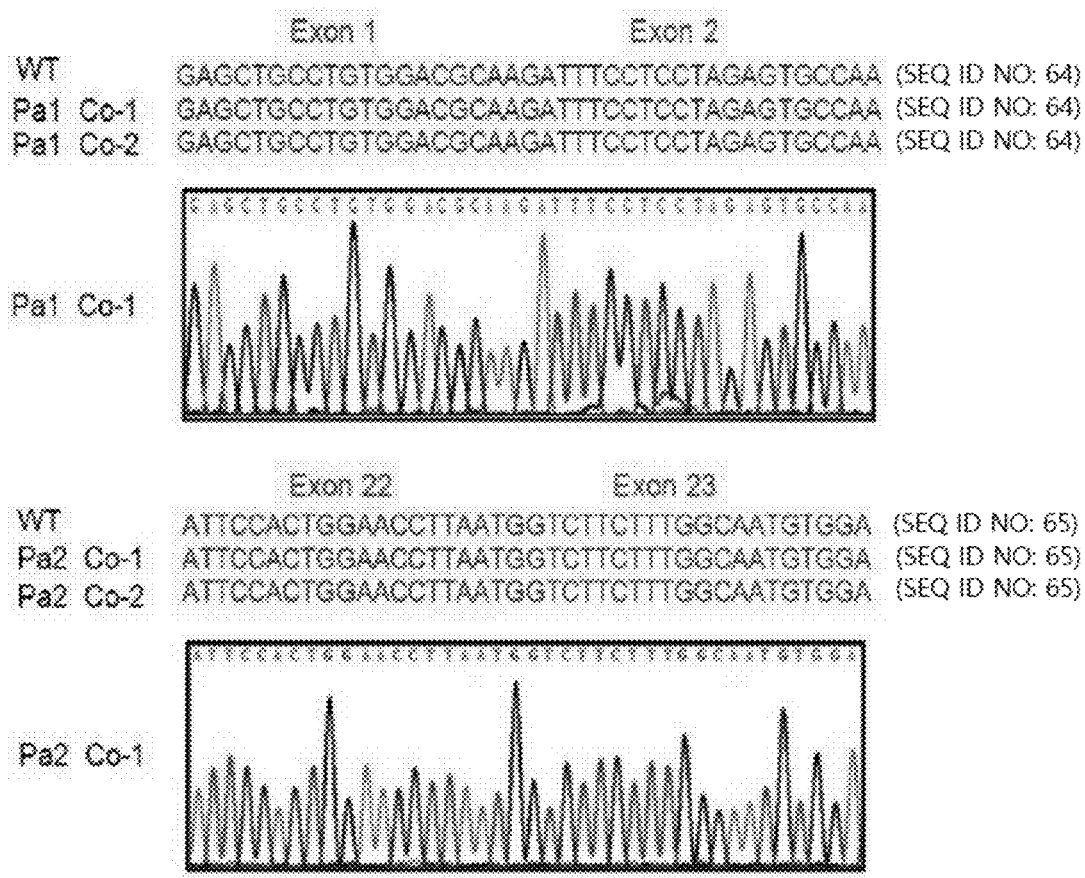

It was confirmed through Sanger sequencing that exons 1 and 2 or exons 22 and 23 were correctly spliced in cells differentiated from the inversion-corrected iPSCs (FIG. 2e). These results prove that the F8 gene was corrected in patient iPSCs having intron 1 and 22 inversions.

To prevent unwanted insertions of plasmid fragments at RGEN on-target and off-target sites, the recombinant Cas9 protein purified after expression in E. coli and the in vitro transcribed sgRNAs (RGEN ribonucleoproteins, or RNPs) were transduced into two patients (Pa1 and Pa3) iPSCs each having an intron 1 or 22 inversion.

Figure 4B:
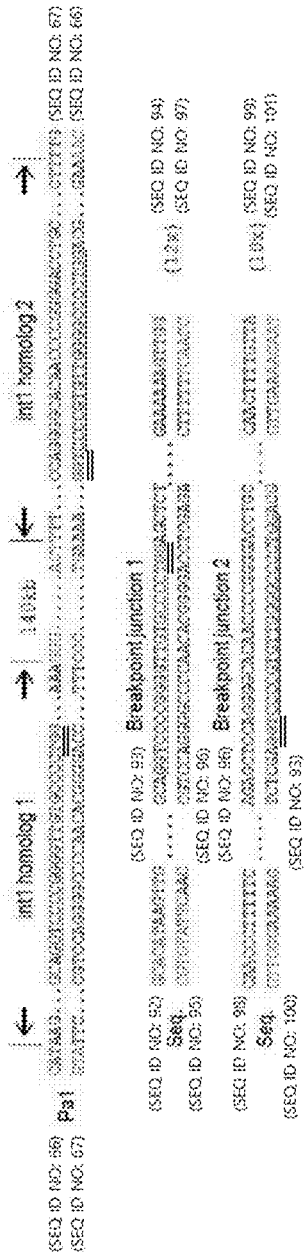
Figure 4C:
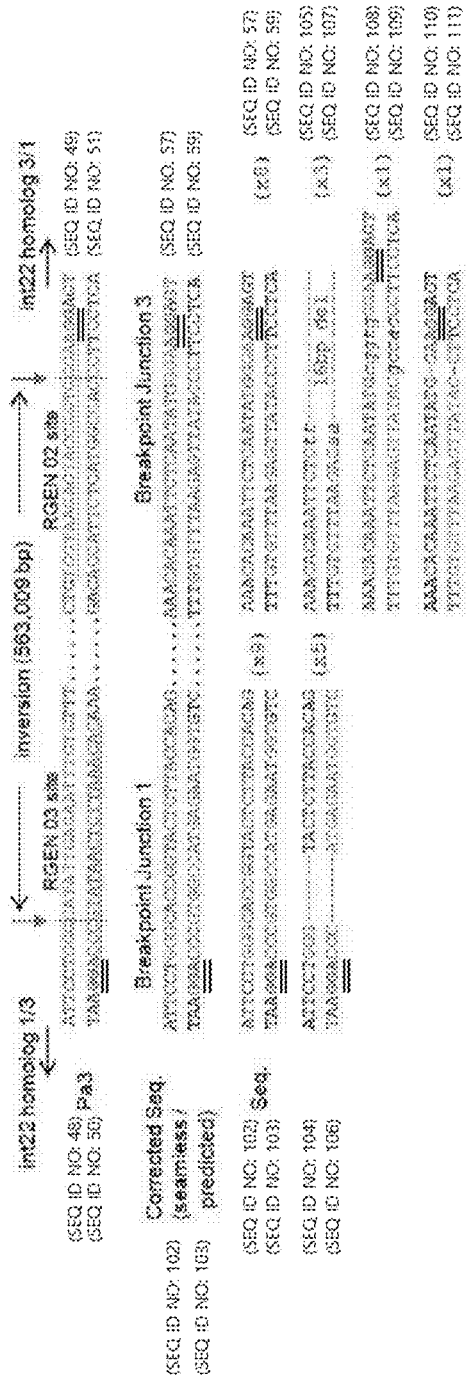

PCR and Sanger sequencing were used to confirm the reversion of the 140-kbp or 563-kbp chromosomal segments restoring the genetic functions of the F8 gene (FIGS. 4b and 4c). Since RNPs, unlike plasmids, cleave chromosomal target DNA immediately after transduction and are rapidly degraded in cells (Kim et al., 2014), off-target effects can be reduced without sacrificing genome correction activity at on-target sites through transduction of RGEN RNP.

RGENs can induce off-target mutations, which are homologous in sequence with on-target sites (Cho et al., 2014; Cradick et al., 2013; Fu et al., 2013; Hsu et al., 2013; and Pattanayak et al., 2013). The present inventors investigated whether the RGENs used in the present invention left any secondary damage in addition to inversion corrections in patient iPSCs using targeted deep sequencing and whole-genome sequencing (WGS). First, the present inventors searched for potential off-target sites that differed from the three RGEN on-target sites by up to three nucleotides in the human genome using Cas-OFFinder, a webbased program accessible at (www.rgenome.net, Bae et al. 2014). A total of 12, 6, and 14 sites were found in RGEN 01, RGEN 02, and RGEN 03, respectively. To confirm that indels were not induced at these sites in the inversion-corrected iPSCs using targeted deep sequencing (FIG. 2).

TABLE 2

Analysis of potential off-target sites

Targeted deep sequencing of off-target sites allowing three mismatches

| RGEM | RGEM01 | RGEM02 | RGEM03 |
|---|---|---|---|
| Off-target sites | 12 | 6 | 14 |
| Confirmed by deep sequencing | 0 | 0 | 0 |

TABLE 2-continued

Analysis of potential off-target sites

WGS analysis and variant information extraction of off-target sites

| Clone | Pa1 | Pa1_Co-1 | Pa2 | Pa2-Co-1 |
|---|---|---|---|---|
| All variants | 4,006,558 | 3,964,083 | 3,945,677 | 3,933,902 |
| Raw indel calls | 505,673 | 496,678 | 488,735 | 477,957 |
| Indels not present in the idel database | 56,586 | 52,832 | 51,105 | 48,614 |
| KO clone-specific indels | 13,707 | 10,914 | 11,578 | 9,848 |

Candidate indels at homologous sites

|  | N/A | (RGEN 01) 52 | N/A | (RGEN 02) 106 | (RGEN 03) 31 |
|---|---|---|---|---|---|
| Excluding repeat sequence | N/A | 7 | N/A | 0 | 3 |
| Confirmed by deep sequencing | N/A | 0 | N/A | 0 | 0 |

Targeted deep sequencing of off-target sites allowing eight mismatches

| RGEN | RGEN 01 | RGEN 02 | RGEN 03 |
|---|---|---|---|
| Off-target sites | 511,710 | 652,127 | 937,778 |
| Potential candidates | 88 | 348 | 163 |
| Excluding repeat sequence | 1 | 2 | 1 |
| Confirmed by deep sequencing | 0 | 0 | 0 |

Next, genomic DNA isolated from patient (Pa1 and Pa2) iPSCs and respective inversion-corrected iPSCs were subjected to WGS. First, Isaac, which is a variant information extraction program, was used to identify indels relative to the hg19 reference genome. The bioinformatics filters were used to exclude the indels registered in the public database, the indels extracted from patient genomes having the int1h or int22h inversion and the other inversion-corrected genomes, and the indels occurring in the homo-polymer or repeat sequences due to sequencing errors. As a result, 9,848 to 13,707 indels that were unique in each inversion-corrected genome sequence were obtained. Next, the RGEN target sites were compared with wild-type loci corresponding to the indel locations. Only 31 to 106 indel sites had 5'-N(G/A)G-3'PAM sequence, and showed at least 12 nucleotide matches with respective on-target sequences (Table 2). Thereafter, the DNA sequences corresponding to these indels in the two inversion-corrected genomes were investigated. None of the indels were validated by targeted deep sequencing. Then, all the potential off-target sites that differed from on-target sites by up to eight nucleotides or that differed by up to two nucleotides with a DNA or RNA bulge of five nucleotides were identified through the Cas-OFFinder. Thereafter, as a result of comparing the sequence reads aligned around 10 of the thousands derived from potential off-target sites with the reference sequence (Table 2), no off-target indels were identified. These results show that the three RGENs used in the present invention did not induce off-target mutations in the inversion-corrected patient iPSCs. In brief, the present inventors used RGENs to repair two recurrent, large chromosomal inversions providing almost half of all severe hemophilia A cases in patient-derived iPSCs, and thus observed that the cells differentiated from the inversion-corrected iPSCs expressed the F8 genes. It was confirmed through targeted deep sequencing and WGS analysis that the off-target mutations were not induced in the inversion-corrected iPSCs. This is the first demonstration that large genomic rearrangements, such as chromosome inversion, can be corrected using RGEN or other gene scissors in patient iPSC. Chromosomal inversions are associated with other genetic diseases, such as Hunter syndrome (Bondeson et al., 1995) and cancer (Nikiforova et al., 2000). Targeted genomic rearrangements using RGENs in iPSCs enable genomic structural variations can be favorably used for units to study their functions and for gene and cell therapy for hemophilia A and other genetic diseases caused by large chromosomal rearrangements.

Example 2. TALEN(Transcription Activator-Like Effector Nucleases)

Methods

Plasmids Encoding TALENs

TALEN plasmids in this study were synthesized by using TAL effector array plasm ids constructed for one-step Golden-Gate assembly as described (Kim Y, et al. (2013) A library of TAL effector nucleases spanning the human genome. Nat Biotechnol 31(3):251-258). Each TALEN plasmid encodes the N-terminal 135 amino acids of AvrBs3, an array of RVD modules, one of the four RVD halfrepeats, and the Sharkey FokI domain (Guo J, Gaj T, Barbas C F, 3rd (2010) Directed evolution of an enhanced and highly efficient FokI cleavage domain for zinc finger nucleases. J Mol Biol 400(1):96-107). TALEN sites were designed to target the intron 1 homolog of the F8 gene; potential off-target sites were identified as described (Kim Y, et al. (2013) A library of TAL effector nucleases spanning the human genome. Nat Biotechnol 31(3):251-258).

Isolation of Genomic DNA from Hemophilia A Patient

Seoul National University Institutional Review Board approval was obtained for the analysis of blood cells of a hemophilia A patient. The blood sample was provided by Korea Hemophilia Foundation Clinic, and genomic DNA was isolated as described (Lee H J, Kweon J, Kim E, Kim S, Kim J S (2012) Targeted chromosomal duplications and inversions in the human genome using zinc finger nucleases. Genome Res 22(3): 539-548).

Measuring the Frequencies of Targeted Inversions. The frequencies of targeted inversions were estimated by digital PCR analysis as described (Kim S, Lee H J, Kim E, Kim J S (2010) Analysis of targeted chromosomal deletions induced by zinc finger nucleases. Cold Spring Harb Protoc 10.1101/pdb.prot5477). The genomic DNA samples isolated from cell transfected with TALEN plasm ids were serially diluted, and the diluted samples were subjected to nested PCR by using appropriate primers (Table 3). The fraction of positive bands at each dilution point was counted, and the results were analyzed by using the Extreme Limiting Dilution Analysis program (Hu Y, Smyth G K (2009) ELDA: Extreme limiting dilution analysis for comparing depleted and enriched populations in stem cell and other assays. J Immunol Methods 347(1-2): 70-78).

TABLE 3

| Primer name | Sequence (5' to 3') | Used for the experiment of |
|---|---|---|
| homolog 1-1F (SEQ ID NO: 5) | AAATCACCCAAGGAAGCACA | Inversion and Reversion |
| homolog 1-1R (SEQ ID NO: 6) | TGGCATTAACGTATTACTTGGAGA | Inversion and Reversion |
| homolog 2-2F (SEQ ID NO: 7) | GGCAGGGATCTTGTTGGTAAA | Inversion and Reversion |
| homolog 2-2R (SEQ ID NO: 8) | TGCTGAGCTAGCAGGTTTAATG | Inversion and Reversion |
| GAPDH-F (SEQ ID NO: 13) | CCCCTCAAGGGCATCCTGGGCTA | qPCR and RT-PCR |
| GAPDH-R (SEQ ID NO: 14) | GAGGTCCACCACCCTGTTGCTGTA | qPCR and RT-PCR |
| Oct4-F (SEQ ID NO: 15) | CCTCACTTCACTGCACTGTA | qPCR |
| Oct4-R (SEQ ID NO: 16) | CAGGTTTTCTTTCCCTAGCT | qPCR |
| Sox2-F (SEQ ID NO: 32) | CCCAGCAGACTTCACATGT | qPCR |
| Sox2-R (SEQ ID NO: 33) | CCTCCCATTTCCCTCGTTTT | qPCR |
| Lin28-F (SEQ ID NO: 34) | AGCCAAGCCACTACATTC | qPCR |
| Lin28-R (SEQ ID NO: 35) | AGATACGTCATTCGCACA | qPCR |
| Nanog-F (SEQ ID NO: 21) | TGAACCTCAGCTACAAACAG | qPCR |
| Nanog-R (SEQ ID NO: 22) | TGGTGGTAGGAAGAGTAAAG | qPCR |
| F8-F (SEQ ID NO: 23) | CTGCTTTAGTGCCACCAGAAGA | RT-PCR |
| F8-R (SEQ ID NO: 24) | GACTGACAGGATGGGAAGCC | RT-PCR |
| FOXA2-F (SEQ ID NO: 36) | CTACGCCAACATGAACTCCA | RT-PCR |
| FOXA2-R (SEQ ID NO: 37) | AAGGGGAAGAGGTCCATGAT | RT-PCR |
| Sox17-F (SEQ ID NO: 38) | AGCGCCCTTCACGTGTACTA | RT-PCR |
| Sox17-R (SEQ ID NO: 39) | CTTGCACACGAAGTGCAGAT | RT-PCR |
| GAPDH-F (SEQ ID NO: 40) | GAACATCATCCCTGCCTCTACTG | iPS generation (PCR) |
| GAPDH-R (SEQ ID NO: 41) | CAGGAAATGAGCTTGACAAAGTGG | iPS generation (PCR) |
| EBNA-1-F (SEQ ID NO: 42) | ATGGACGAGGACGGGGAAGA | iPS generation (PCR) |
| EBNA-1-R (SEQ ID NO: 43) | GCCAATGCAACTTGGACGTT | iPS generation (PCR) |
| 293-F (SEQ ID NO: 44) | GAGCAGGGAGGCAAGAATTA | TALENs activity screening |

TABLE 3-continued

Primers

| Primer name | Sequence (5' to 3') | Used for the experiment of |
|---|---|---|
| 293-R (SEQ ID NO: 45) | TGAGGGAAAACGCATCTAGG | TALENs activity screening |

Cell Cultures

HEK 293T/17 (ATCC; CRL-11268) and adult HDFs (Invitrogen; C-004-5C) were cultured in DMEM supplemented with FBS (10% vol/vol) and antibiotics (1%). Human ESC (hESC) lines (H9) obtained from WiCell, retrovirus-derived wild-type iPSCs (iPSC1), and iPSCs generated in this study were maintained in hESC medium composed of DMEM/F12 medium supplemented with 20% (vol/vol) knockout serum replacement (Invitrogen), 4.5 g/L L-glutamine, 1% nonessential amino acids, 0.1 mM 2-mercaptoethanol, and 4 ng/mL basic FGF (PeproTech) as described (Kim D S, et al. (2010) Robust enhancement of neural differentiation from human ES and iPS cells regardless of their innate difference in differentiation propensity. Stem Cell Rev 6(2):270-281).

Validation of TALENs Targeting the F8 Locus in HEK 293T Cells

To validate the genome-editing activities of the TALENs designed for this study, each TALEN pair was transfected into HEK 293T cells, and their activities were measured by using the T7E1 assay (Kim H J, Lee H J, Kim H, Cho S W, Kim J S (2009) Targeted genome editing in human cells with zinc finger nucleases constructed via modular assembly. Genome Res 19(7): 1279-1288). To measure the frequency of targeted inversions induced by TALENs targeting the F8 locus, HEK 293T/17 cells were seeded at 80% confluency before transfection and transfected by using Lipofectamine 2000 (Invitrogen) with TALEN-encoding plasm ids. Genomic DNA samples were isolated and subjected to PCR analysis to confirm chromosomal inversion as described (Kim S, Lee H J, Kim E, Kim J S (2010) Analysis of targeted chromosomal deletions induced by zinc finger nucleases. Cold Spring Harb Protoc 10.1101/pdb.prot5477).

Generation of iPSCs and in Vitro Differentiation into Three Germ Layers

Episomal vectors encoding defined reprogramming factors were used as reported (Okita K, et al. (2011) A more efficient method to generate integration-free human iPS cells. Nat Methods 8(5):409-412). In brief, HDFs grown in DMEM supplemented with 10% FBS were electroporated by using a microporator system (Neon; Invitrogen) with episomal vector mixtures (total 3 μg) according to the manufacturer's instructions. After being pulsed three times with a voltage of 1,650 for 10 ms, the cells were grown further in DMEM (containing 10% FBS). Seven days after transfection, cells were transferred onto a feeder layer.

iPSC colonies that looked similar to hESCs were picked up mechanically and further cultured for characterization. In vitro differentiation of the iPSCs into three germ layers was induced as described (Sugii S, et al. (2010) Human and mouse adipose-derived cells support feederindependent induction of pluripotent stem cells. Proc Natl Acad Sci USA 107(8): 3558-3563). Embryoid bodies (EBs), formed by partially dissociating iPSCs using collagenase type IV (Invitrogen), were transferred to ultralow attachment plates (Corning) and cultured in DMEM/F12 (1:1) medium supplemented with 20% knockout serum (Invitrogen), 4.5 g/L L-glutamine, 1% nonessential amino acids, 0.1 mM 2-mercaptoethanol, and 5% FBS. After a week of cultivation under these conditions, EBs were attached onto Matrigel-coated culture dishes and further cultured for 10 d. Spontaneous differentiation of EBs into cells representing the three germ layer lineages was detected by immunostaining with appropriate antibodies.

Differentiation of iPSCs

To induce differentiation of iPSCs into the endoderm lineage, we used a described method (Si-Tayeb K, et al. (2010) Highly efficient generation of human hepatocyte-like cells from induced pluripotent stem cells. Hepatology 51(1): 297-305). In brief, iPSC colonies were cultured in mTeSR-1 hESC growth medium (StemCell Technology) for feederfree culture. Undifferentiated iPSCs were incubated to obtain definitive endoderm cells in RPMI/B27 (RPMI-1640 from Sigma; B27 supplement from Invitrogen) medium supplemented with 100 ng/mL Activin A (PeproTech) and 5 μM phosphatidylinositol 3—kinase inhibitor (LY-294002; Sigma) for 5 d. Cells that had differentiated into endoderm were harvested for isolation of total RNAs, which were used as template for cDNA synthesis.

To induce differentiation of iPSCs into the endothelial cells, we used a described method (Yoo CH, et al. (2013) Endothelial progenitor cells from human dental pulp-derived iPS cells as a therapeutic target for ischemic vascular diseases. Biomaterials 34(33):8149-8160) with slight modifications. In brief, EBs were cultured in hESC medium supplemented with 20 ng/mL bone morphogenic protein 4 (R&D Systems) and 10 ng/mL Activin A (PeproTech). On day 3 of EB formation, the EBs were attached onto Matrigel-coated dishes and induced to differentiate into endothelial cells for up to 10 d in medium supplemented with 100 ng/mL VEGF (PeproTech) and 50 ng/mL basic FGF (R&D Systems).

TALEN Transfections for Inducing Inversion and Reversion in iPSCs

Cultured iPSCs were harvested by treating with collagenase type IV. After washing with PBS, the cells were further treated with Accutase (Invitrogen) to create singlecell suspensions as described (Desbordes S C, et al. (2008) High-throughput screening assay for the identification of compounds regulating self-renewal and differentiation in human embryonic stem cells. Cell Stem Cell 2(6):602-612). These single cells were mixed with 10 μg of TALEN-encoding plasmids (5 μg of each plasmid) and pulsed with a voltage of 850 for 30 ms. Cells were then seeded onto feeder cells and allowed to grow for 10 d. To detect genomic inversion or reversion events, cells from individual colonies were lysed in 20 μL of lysis buffer [1× Ex-taq buffer (pH 8.0) containing proteinase K] at 56° C. for 3 h. After inactivation of proteinase K, 2 μL of genomic DNA solution was subjected to PCR by using Ex-taq DNA polymerase (Takara) and specific primers. PCR products were analyzed by agarose gel electrophoresis. Specific primer sequences are shown in Table 5.

Isolation of Clonal Populations of Cells, PCR Analysis, and DNA Sequencing of Breakpoints To isolate clonal populations of inverted (or reverted) cells, each colony that had been identified by PCR as containing the desired genomic event was dissociated into single cells by using collagenase and Accutase as described above and replated. After three rounds of passaging, several clones (six clones for inversion, four clones for reversion) were chosen for sequencing and further experiments. For sequence determination, amplified PCR products were electrophoresed, eluted from the agarose gel by using a Gel Extraction kit (SolGent), and cloned into the pGEM-T vector (Promega). Cloned PCR products were sequenced by using T7 primers.

RNA Isolation, RT-PCR, and qPCR

Total RNAs were purified from cells by using TRIzol reagent (Invitrogen) according to the manufacturer's instructions. cDNAs were synthesized from total RNAs (1 µg) by using the DiaStar cDNA synthesis kit (SolGent). To confirm the expression of Factor VIII, FOXA2, Sox17, and GAPDH, PCR was performed with Ex-Taq (Takara) by using the synthesized cDNAs as template. For qPCR, SYBR Premix Ex-Taq (Takara) was used according to the manufacturer's instructions. Specific primer sequences used for RT-PCR or qPCR are shown in Table 5.

Alkaline Phosphatase Staining and Immunostaining

Alkaline phosphatase activity was measured with the leukocyte alkaline phosphatase staining kit (Sigma) according to the manufacturer's instructions. For the immunostaining of pluripotent stem cell markers, cells were fixed in 4% paraformaldehyde solution and permeabilized with 0.2% Triton X-100. After washing with PBS, the cells were incubated with a PBS solution containing 5% normal goat serum and 2% BSA. The cells were then incubated with primary antibodies for 2 h at room temperature, washed with PBS, and incubated with fluorescence-conjugated secondary antibodies (Alexa Fluor 488 or 594; Invitrogen) for 1 h at room temperature. The cells were mounted with an antifade mounting medium containing DAPI (Vector Laboratories) for nuclei visualization. The images were captured and analyzed by using an Olympus IX71 microscope or FSX system.

DNA Fingerprinting and Karyotype Analysis

To confirm the dermal fibroblast origin of iPSC lines, PCR-based short tandem repeat (STR) analysis was carried out at the Gene-Analysis Institute of Human Pass Inc. In brief, STR loci were amplified from genomic DNA samples isolated from iPSC lines and their parental cells by using the AmpFISTR PCR system (Applied Biosystems). The amplified products were analyzed by using an ABI PRISM 3130XL genetic analyzer and Genemapper (Version 3.2; Applied Biosystems). For karyotype analysis, chromosomes were stained with Giemsa for G-banding analysis and analyzed by the Chromosome Image Processing System at GenDix.

Statistical Analysis. Data are presented as means±SEs

Student t test was used for statistical analysis. P<0.05 was considered statistically significant.

Results

Generation and Characterization of Human iPSCs

Figure 5A:
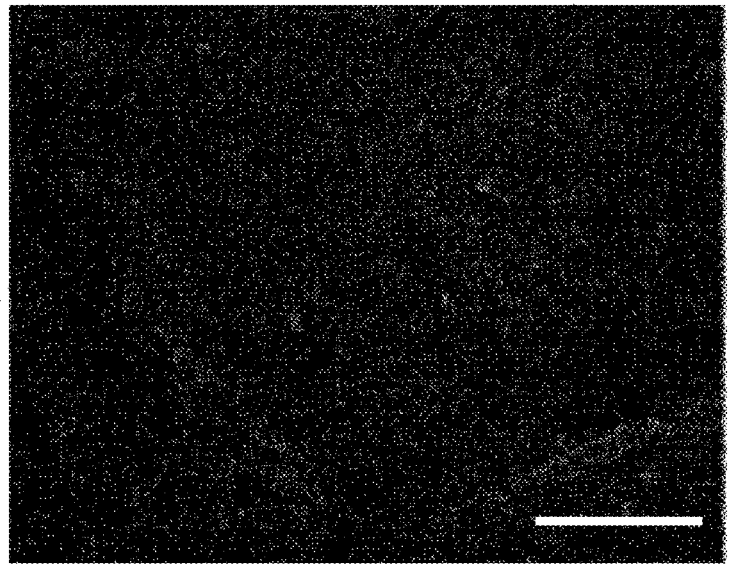
FIGS. 5a to 5g show generation of iPSC clones from HDFs using episomal reprogramming vectors. (5a) Morphology of the expanded human iPSCs (clone Epi3). (Scale bar, 200 μm.) (5b) Alkaline phosphatase staining of iPSCs (clone Epi3). (Scale bar, 500 μm.) (5c) Detection of an episomal vector sequence (EBNA-1) that remained in established iPSC lines (Epi1-Epi8). The GAPDH gene was used as a quality control for isolated total DNA. Total DNA isolated from the cells before (naïve) and after (day 6) electroporation was used as negative and positive controls for episomal vector DNA. A retrovirus-derived wild-type iPSC line (iPSC1) was also analyzed as a negative control. (5d) The expression of OCT4 and SSEA-4, which are human ESC-specific markers, was detected by immunocytochemistry. DAPI signals indicate the total cell presence in the image. (Scale bars, 100 μm.) (5e) RT-PCR analysis to determine the transcriptional levels of OCT4, SOX2, LIN28, NANOG, and GAPDH using gene-specific primers (listed in Table S3). mRNA levels were measured in HDFs, human ES line (H9), a wild-type iPSC line (WT-iPSCEpi3), and inversion clones (Inv 1 and Inv 2) derived from the WT-iPSCEpi3 line (1, HDFs; 2, H9; 3, WT-iPSC; 4, Inv 1; 5, Inv 2). (5f) Quantification of OCT4, SOX2, and LIN28 mRNAs in the indicated cell lines as determined by qPCR and normalized to GAPDH expression. (5 g) Expression of marker proteins representing ectoderm (Nestin), mesoderm (α-smooth muscle actin; α-SMA), and endoderm (α-fetoprotein; AFP). (Scale bars, 50 μm.)
Figure 5B:
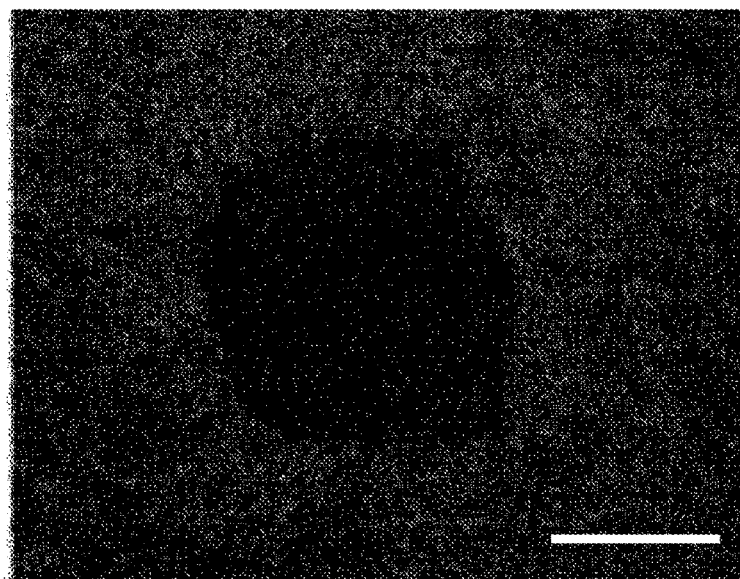
Figure 5C:
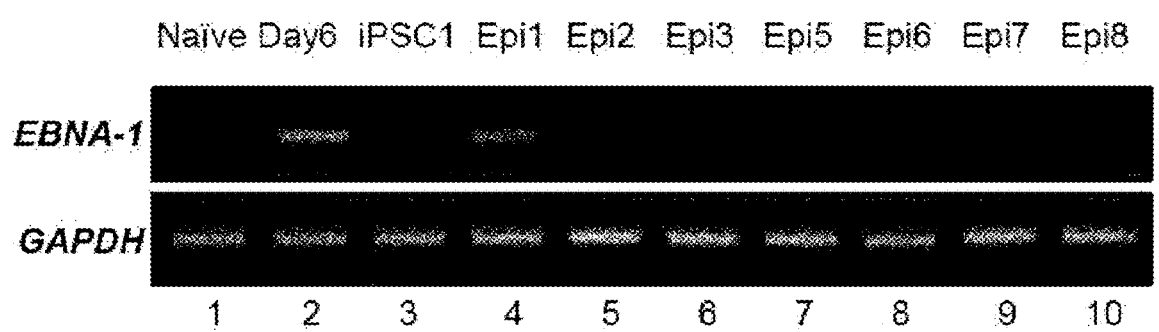
Figure 10A:
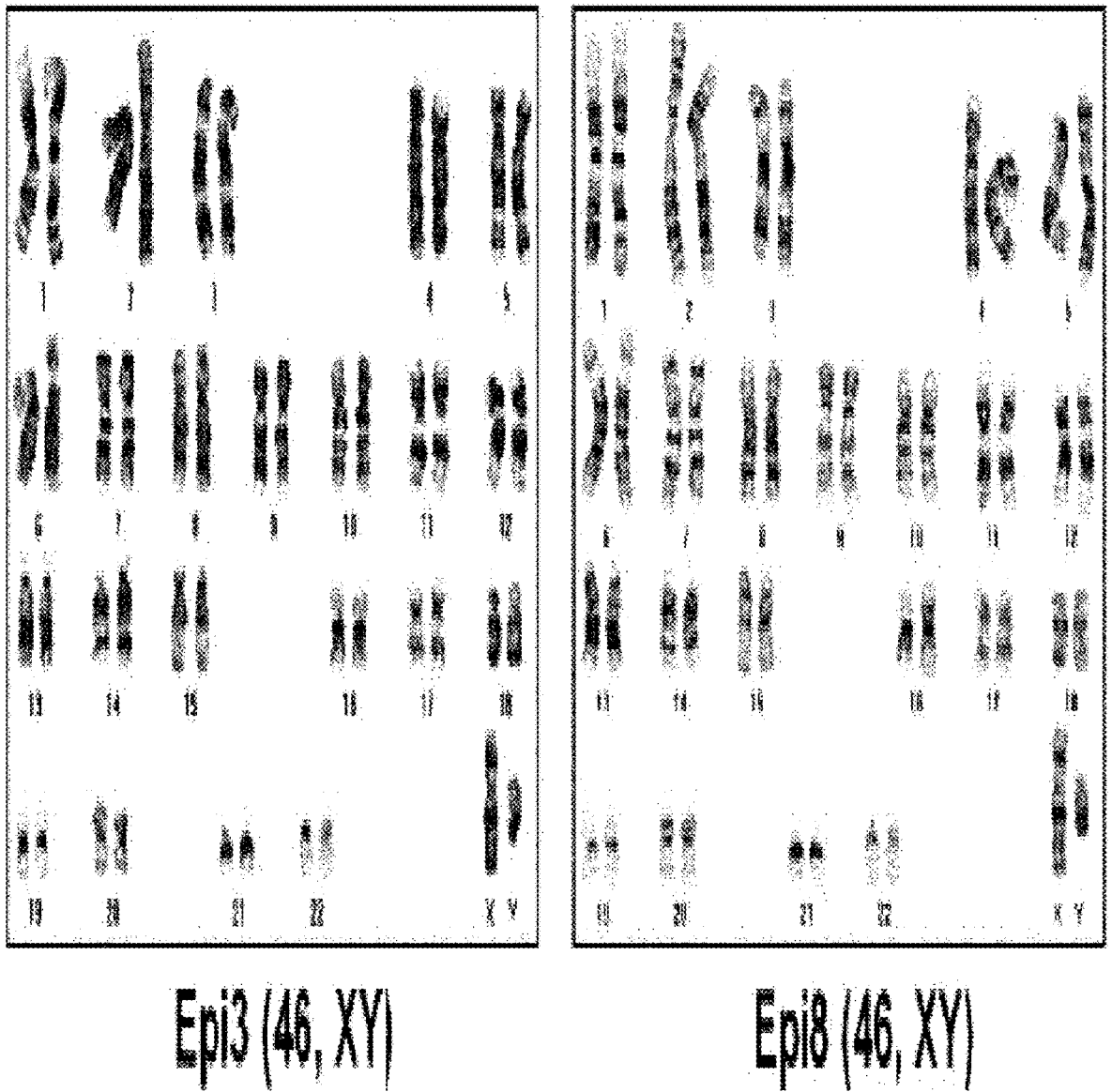
FIGS. 10a to 10c show characterization of human induced pluripotent stem cells (iPSCs) generated by episomal reprogramming vectors. (10a) Karyotype analyses were performed on chromosomes from WT-iPSC lines at passages 10 (Epi3) and 12 (Epi8). (10b) Expression of Nanog and TRA-1-60, which are human embryonic stem cell (ESC)-specific surface markers, was detected by immunocytochemistry. DAPI signals indicate the total cell presence in the image. (Scale bars, 100 μm.) (10c) The expression of marker proteins representing ectoderm (Pax6), mesoderm (Brachyury), and endoderm [hepatocyte nuclear factor 3-β (HNF3β)]. (Scale bars, 50 μm.)

We derived wildtype iPSCs from human dermal fibroblasts (HDFs) using episomal vectors that encode the four Yamanaka factors, which we introduced into cells by electroporation. Embryonic stem cell (ESC)-like colonies appeared 10 d after replating of transfected cells onto a feeder cell layer. We selected a total of eight colonies (termed Epi1-Epi8) exhibiting alkaline phosphatase activities (FIGS. 5a and 5b). To confirm the absence of episomal vectors in these clones after seven or eight passages, we used PCR with specific primers for the EBNA-1 sequence, which is encoded in the vectors. Only one clone (Epi1) contained the EBNA-1 sequence; this clone was excluded from further analyses (FIG. 5c). Next, we checked the karyotypes of two iPSC lines (Epi3 and Epi8). As shown in FIG. 10a, they had a normal karyotype. We also confirmed that these iPSC lines were derived from parental HDFs using DNA fingerprinting analysis (Table 4). After these initial characterizations, we chose the Epi3 line for further experiments.

TABLE 4

Short tandem repeat (STR) analyses of iPS cell lines

| Locus | HDF | Epi3 | Epi4 | Epi8 |
|---|---|---|---|---|
| D8S1179 | 11 15 | 11 15 | 11 15 | 11 15 |
| D21S11 | 29 30 | 29 30 | 29 30 | 29 30 |
| D7S82 | 10 11 | 10 11 | 10 11 | 10 11 |
| CSF1PO | 11 13 | 11 13 | 11 13 | 11 13 |
| D3S1358 | 16 18 | 16 18 | 16 18 | 16 18 |
| TH01 | 8 9 | 8 9 | 8 9 | 8 9 |
| D13S317 | 8 10 | 8 10 | 8 10 | 8 10 |
| D16S539 | 9 13 | 9 13 | 9 13 | 9 13 |
| D2S1338 | 20 23 | 20 23 | 20 23 | 20 23 |
| D19S433 | 13 14 | 13 14 | 13 14 | 13 14 |
| vWA | 14 18 | 14 18 | 14 18 | 14 18 |
| TPOX | 8 11 | 8 11 | 8 11 | 8 11 |
| D18S51 | 14 24 | 14 24 | 14 24 | 14 24 |
| D5S818 | 12 12 | 12 12 | 12 12 | 12 12 |
| FGA | 23 26 | 23 26 | 23 26 | 23 26 |

Figure 5D:
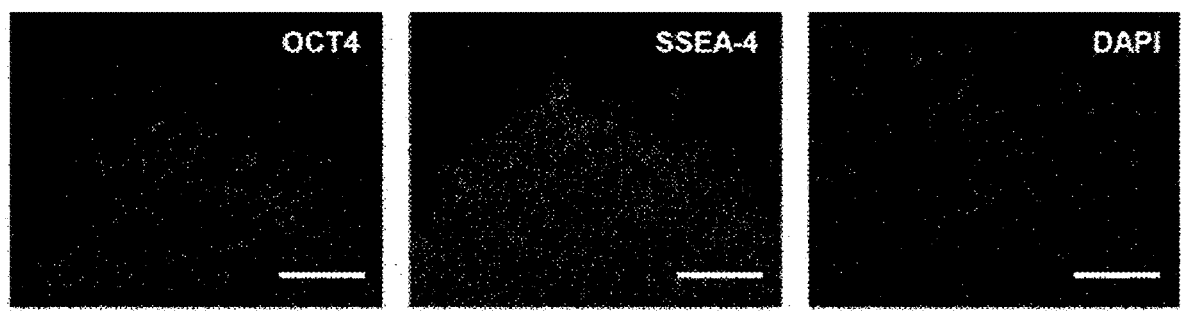
Figure 5E:
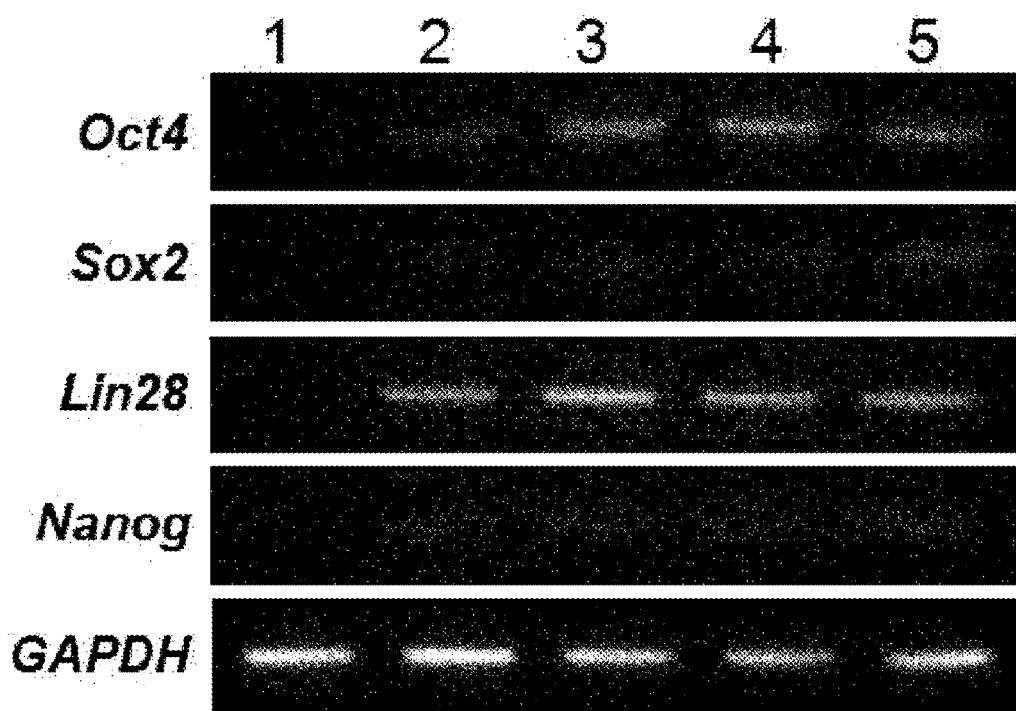
Figure 5F:
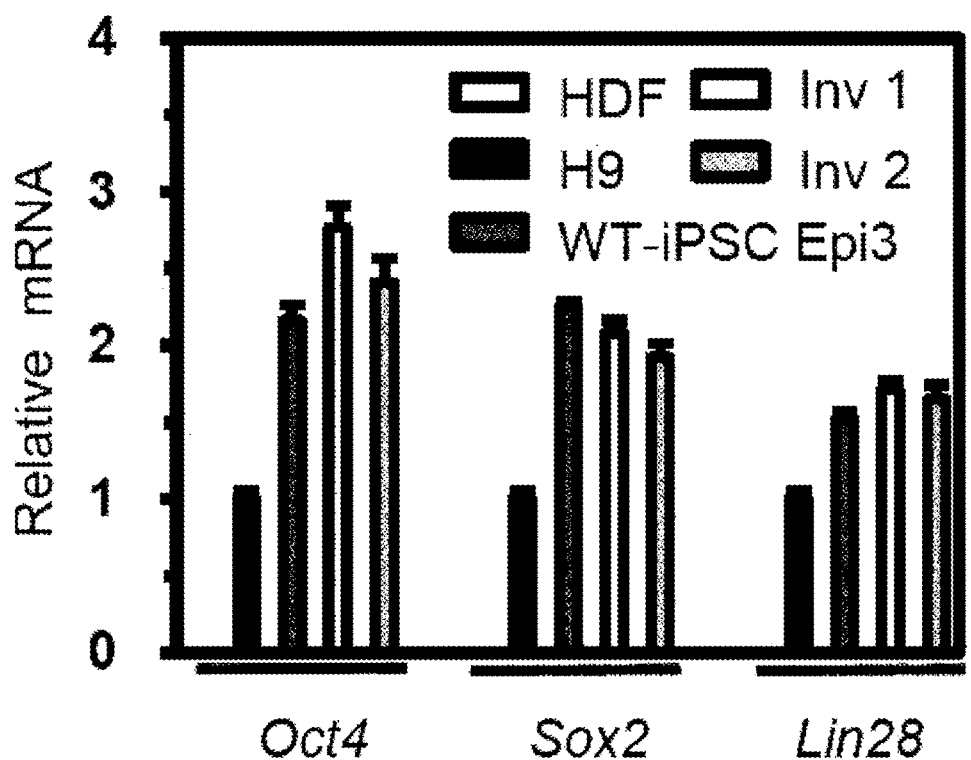
Figure 5G:
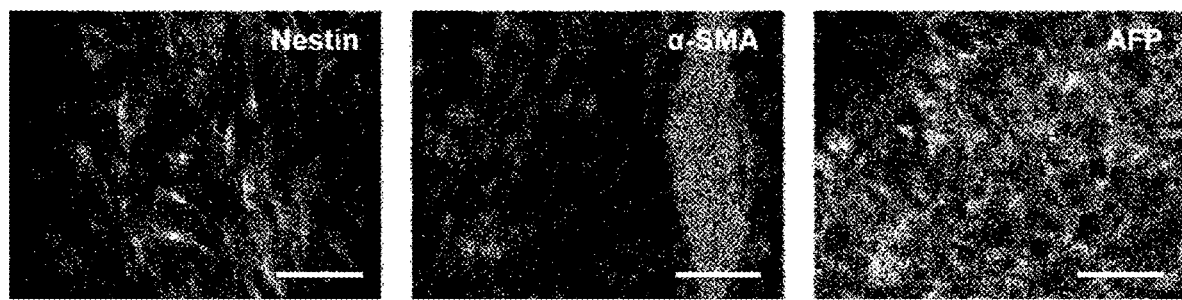
Figure 10B:
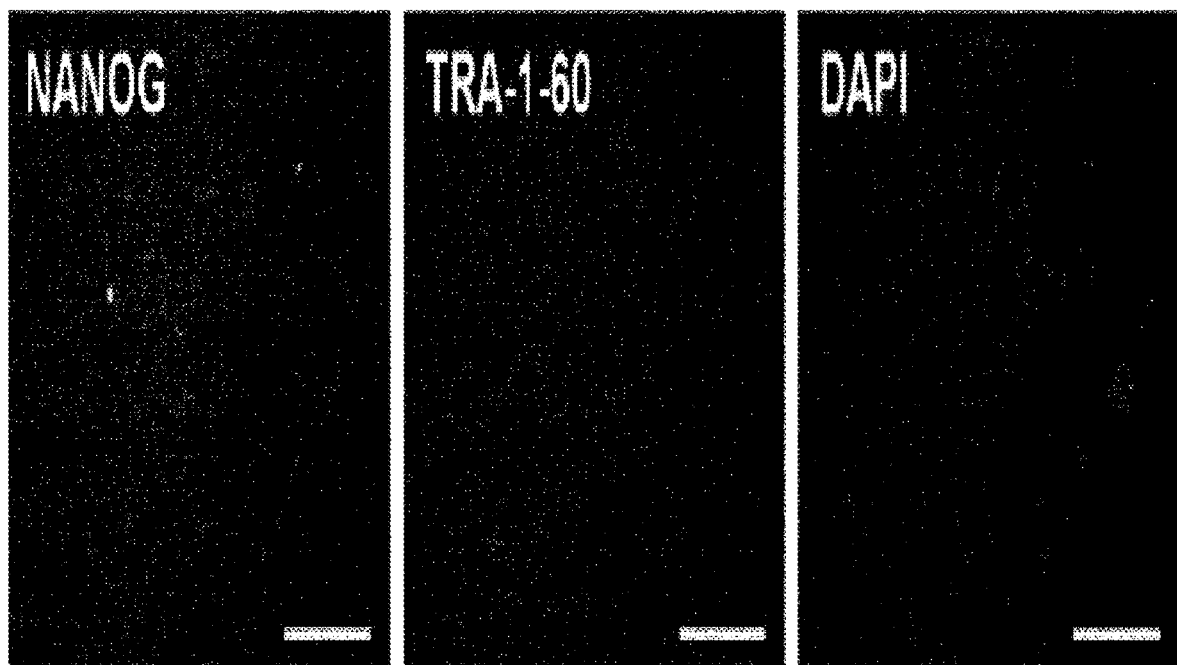
Figure 10C:
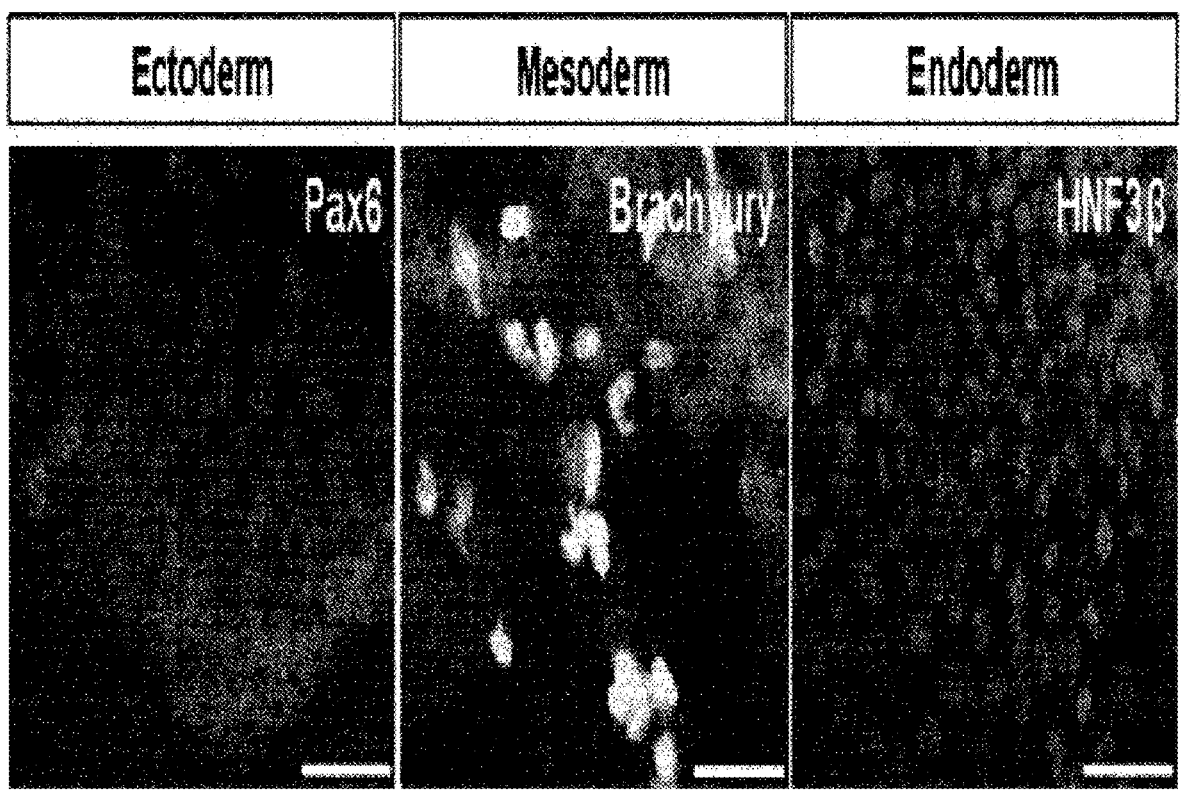

This iPSC line expressed the typical ESC marker proteins such as OCT4, NANOG, SSEA-4, and TRA-1-60 (FIG. 5d and FIG. 10b). RT-PCR and quantitative PCR (qPCR) analyses showed that pluripotent marker genes were expressed at higher levels in this iPSC line than in the human ESC line H9 (FIGS. 5e and 5f). Next, we determined the differentiation potential of the Epi3 iPSC line. Embryonic bodies were derived and attached to gelatin-coated culture plates for spontaneous differentiation into three germ layers in vitro. As expected, marker proteins for ectoderm (Nestin and Pax6), mesoderm [α-smooth muscle actin (α-SMA) and Brachyury], and endoderm [α-fetoprotein (AFP) and hepatocyte nuclear factor 3-β(HNF3β)] lineages were expressed in the differentiated cells (FIG. 5g and FIG. 10c). These data indicate that the Epi3 line derived from adult HDFs is pluripotent.

Targeted Inversion of the F8 Locus in iPSCs Using a TALEN Pair

Figure 6A:
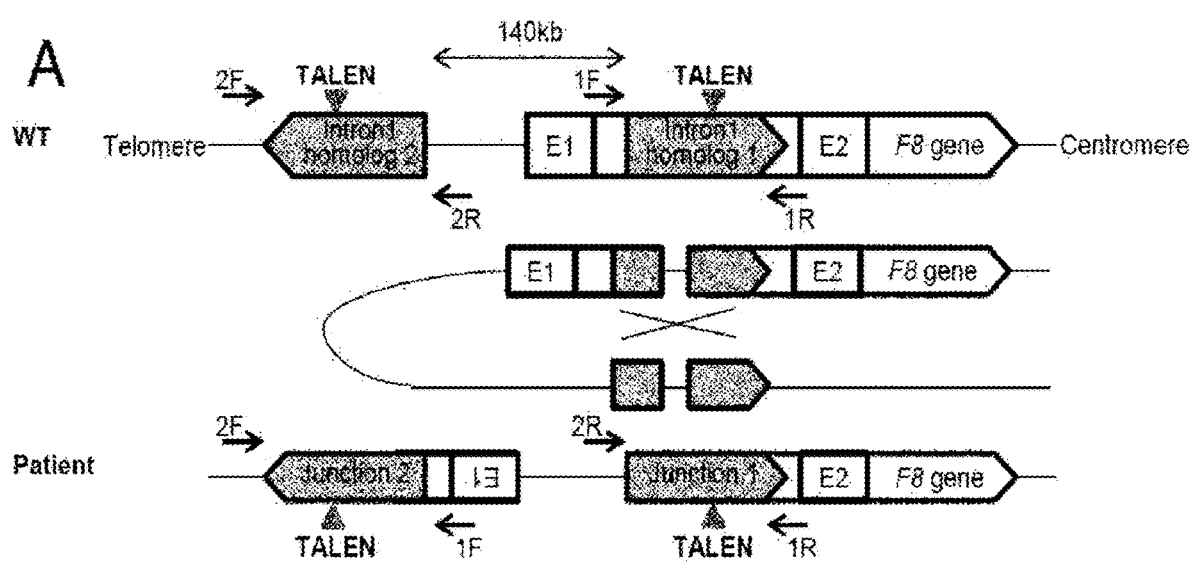
FIGS. 6a to 6b show TALEN-mediated inversion of the F8 gene in HEK 293T cells. (6a) Proposed mechanism of a chromosomal inversion found in patients with severe hemophilia A. Inversions of 140-kbp chromosomal segments spanning the F8 gene are associated with two homologous regions oriented in opposite directions: homolog 1 located in intron1 of the F8 gene and homolog 2 located in the 140-kbp upstream region. Colored triangles show TALEN target sites, and arrows indicate the primers designed to detect 140-kbp inversions. (6b) T7E1 assay results of the 11 TALEN pairs we designed. The predicted positions of DNA bands cleaved by T7E1 are indicated by asterisks.
Figure 6B:
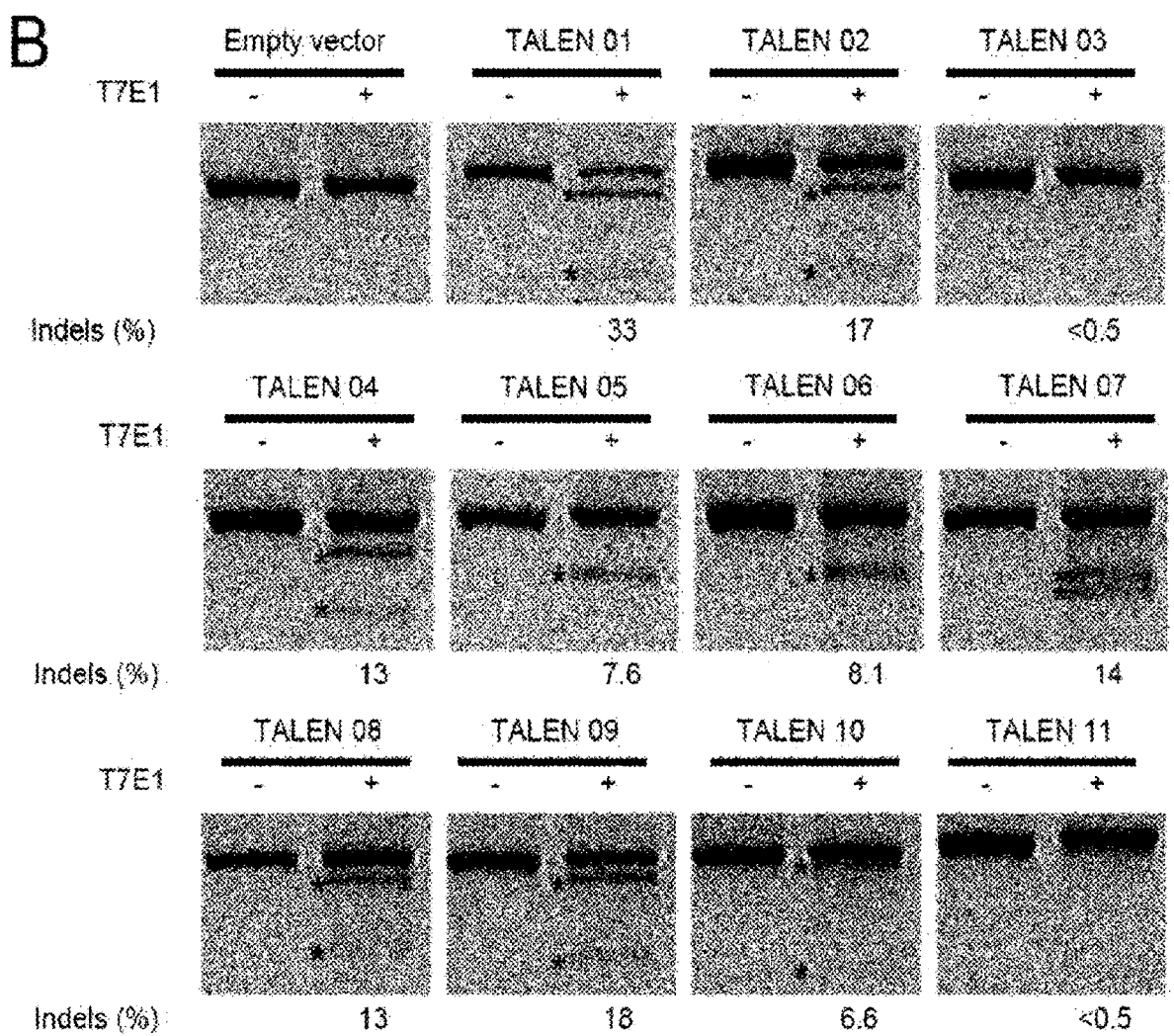
Figure 11A:
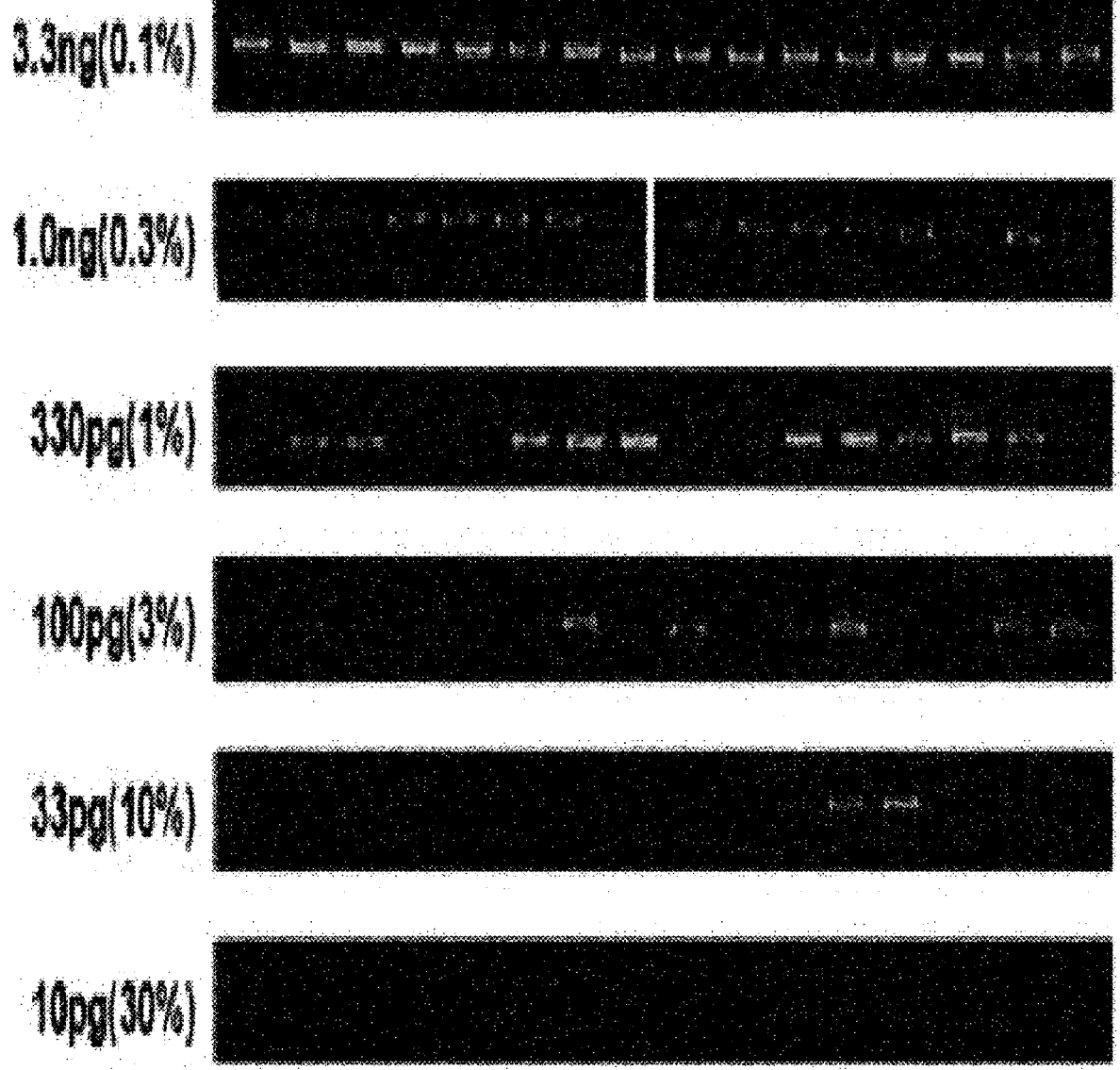
Figure 12:
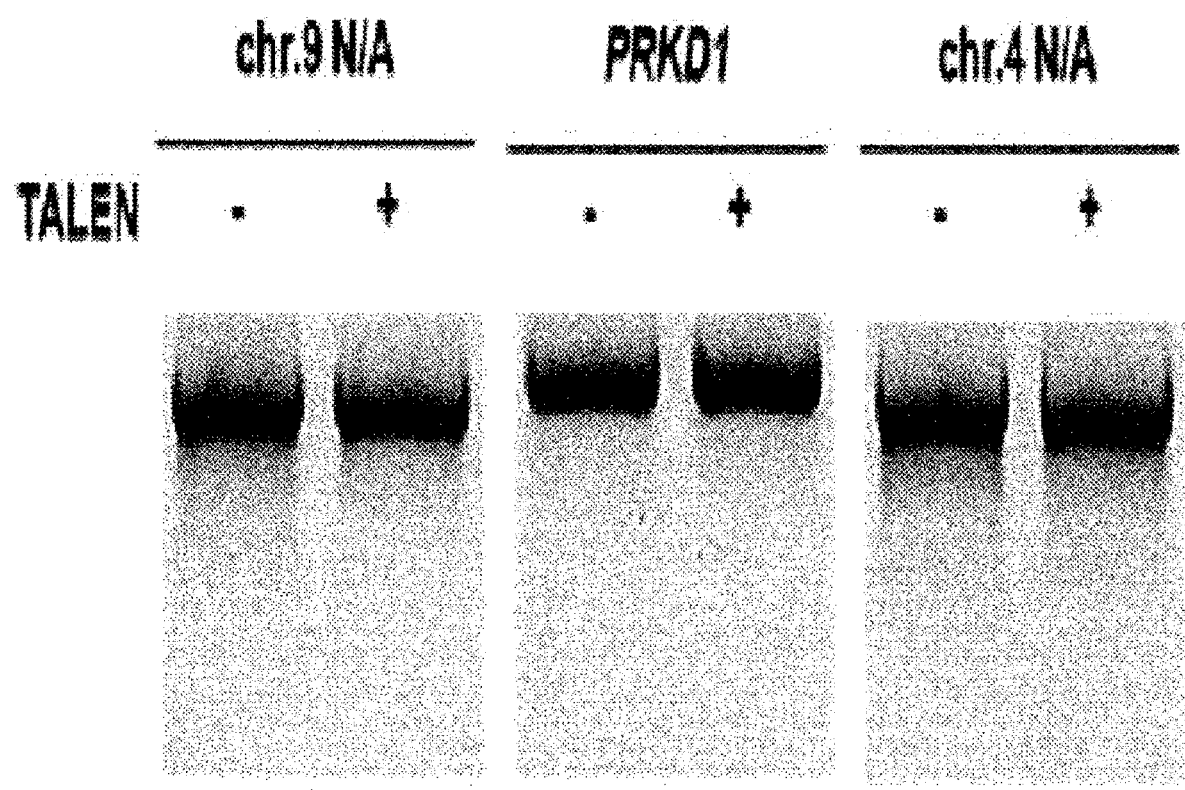
FIG. 12 shows analysis of TALEN off-target effects. Potential off-target sites of TALENs designed for this study were searched in silico. The three potential off-target sites most similar to the TALEN target site were selected and subjected to T7E1 analysis to confirm the off-target cleavage activities at these sites.
Figure 13:
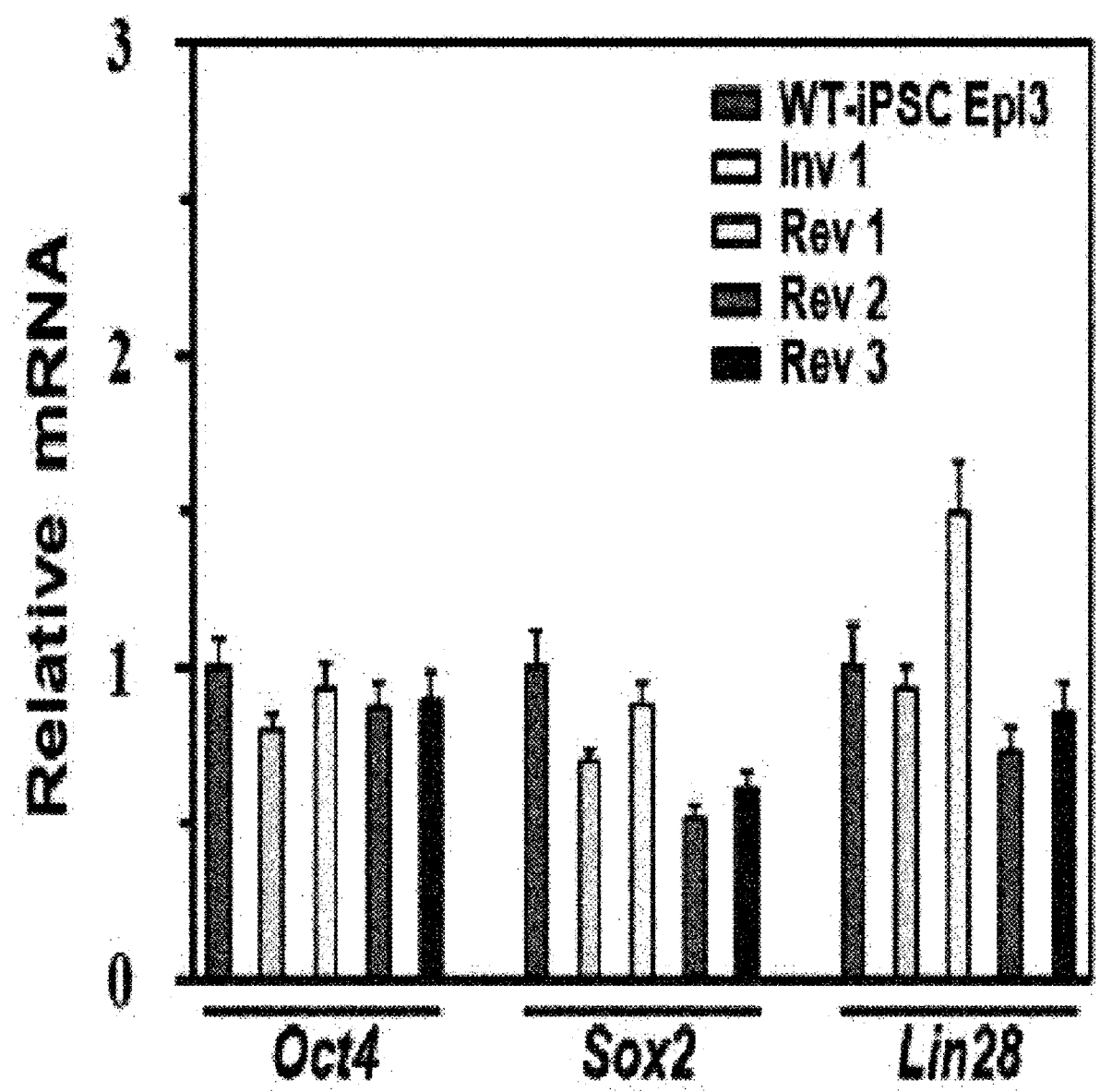
FIG. 13 shows expression of human ES markers from inverted and reverted clones. Oct4, Sox2, and Lin28 mRNA levels from wild-type iPSC line (WT-iPSCEpi3), inversion clone (Inv 1), and reverted clones (Rev 1, 2, and 3) were quantified by quantitative PCR (qPCR). GAPDH mRNA levels were used for normalization.

Structural variations (SVs) such as inversions are associated with genetic diseases including hemophilia A (Feuk L, Carson A R, Scherer S W (2006) Structural variation in the human genome. Nat Rev Genet 7(2):85-97). Almost half of all severe hemophilia A cases are caused by two different types of inversions that disrupt the integrity of the X-linked F8 gene. These inversions result from nonallelic HR (NAHR) that involves sequences present in intron 1 (1-4% of severe hemophilia A cases) or intron 22 (up to 50% of severe hemophilia A cases) and their corresponding homologous sequences located far upstream of the F8 gene (referred to as the intron 1 or 22 inversion, respectively) (Lakich D, Kazazian H H, Jr., Antonarakis S E, Gitschier J (1993) Inversions disrupting the factor VIII gene are a common cause of severe haemophilia A. Nat Genet 5(3):236-241). In this study, the inventors focused on the intron 1 inversion and constructed 11 pairs of TALENs that target the intron 1 homolog (FIG. 6a). The genome-editing activities of these TALENs were tested in HEK 293T cells by using T7 endonuclease I (T7E1) assays (Kim H J, Lee H J, Kim H, Cho S W, Kim J S (2009) Targeted genome editing in human cells with zinc finger nucleases constructed via modular assembly. Genome Res 19(7): 1279-1288) (FIG. 6b). We chose the most active TALEN pair (termed TALEN 01) that induced mutations with a frequency of 33% at the target site. Importantly, this TALEN induced the 140-kb inversion that involves the intron 1 homolog in HEK 293T cells at a frequency of 1.9% (FIG. 11). Next, we tested whether this TALEN had off-target effects at highly homologous sites. No off-target mutations were detected at these sites by using T7E1 assays (FIG. 12 and Table 5).

TABLE 5

Potential off-target sites of TALEN 01

| Chromo-some no. | Gene name | Left-half site (5' to 3') | Spacer (bp) | Right-half site (5' to 3') |
| --- | --- | --- | --- | --- |
| chr.9 | N/A | TATAGATTtGCCAtTtTCTC | 13 | TAAAaTATAAaGAAAAgTtT |
| chr.14 | PRKD1 | TgTAGATTGGtCAGTgTCTC | 12 | aAAAGcAaAcTcAAAACTGT |
| chr.4 | N/A | TtTtGATTGGCCAGcCTCTC | 12 | aAAAGaAaAcTGAAAACaGa |

Figure 7A:
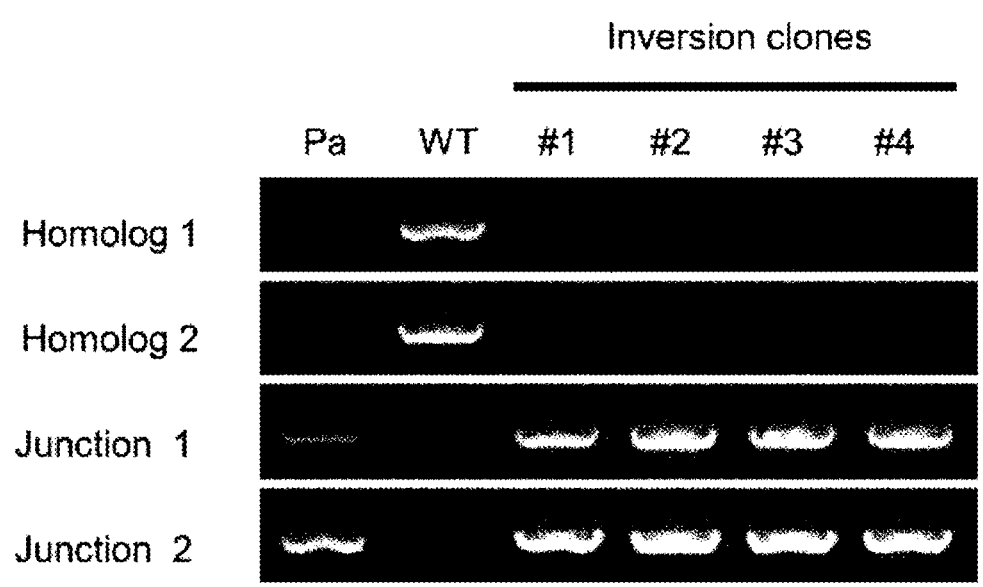

Then the inventors used the same TALEN pair to induce the 140-kb inversion in iPSCs and to create a hemophilia model cell line. Wild-type iPSCs were electroporated with the TALEN plasmids and cultured for 10 d to form colonies. Genomic DNA samples isolated from each colony were subjected to PCR by using specific primer sets that detect the inversion event. Six colonies of 432 (1.4%, comparable to that in HEK 293 cells) showed positive PCR bands for the two inversion breakpoint junctions. Four colonies were then further cultured to derive single cell clones. These clones produced PCR bands that are diagnostic of the 140-kb inversion but, importantly, did not produce PCR bands that correspond to the wild-type genotype (FIG. 7a). Next, we cloned these PCR products and determined their DNA sequences to confirm the inversion genotype. No indels were found at the TALEN target sites (FIG. 7b). This result suggests that a single DSB that was induced by the TALEN in either the intron 1 homolog 1 or homolog 2 triggered DNA inversion via error-free NAHR. However, we cannot rule out the possibility that the TALEN produced two concurrent DSBs—one in the intron homolog 1 and the other in homolog 2—and that these DSBs were joined seamlessly by NHEJ without leaving secondary mutations.

Targeted Reversion of the Inverted Segment in the iPSC System

In our previous study, we induced the targeted chromosomal inversion that involves the intron 1 homolog in the HEK 293 cell line using a ZFN pair and isolated heterozygous clones that harbor the inversion (Lee H J, Kweon J, Kim E, Kim S, Kim J S (2012) Targeted chromosomal duplications and inversions in the human genome using zinc finger nucleases. Genome Res 22(3): 539-548). However, HEK 293 cells do not express the F8 gene and cannot be used in cell therapy. Furthermore, HEK 293 cells carry three copies of the X chromosome. These limitations hampered our efforts to revert the inverted region back to the normal orientation to restore expression of the F8 gene, a demonstration required for therapeutic applications.

Figure 8A:
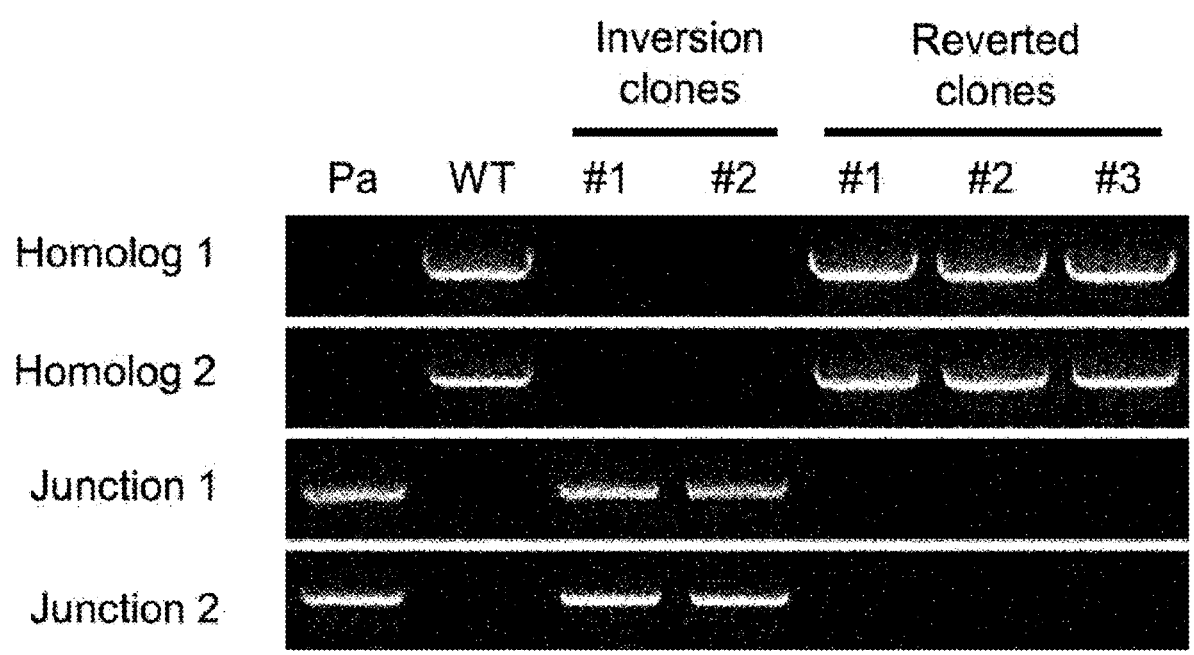
Figure 8C:
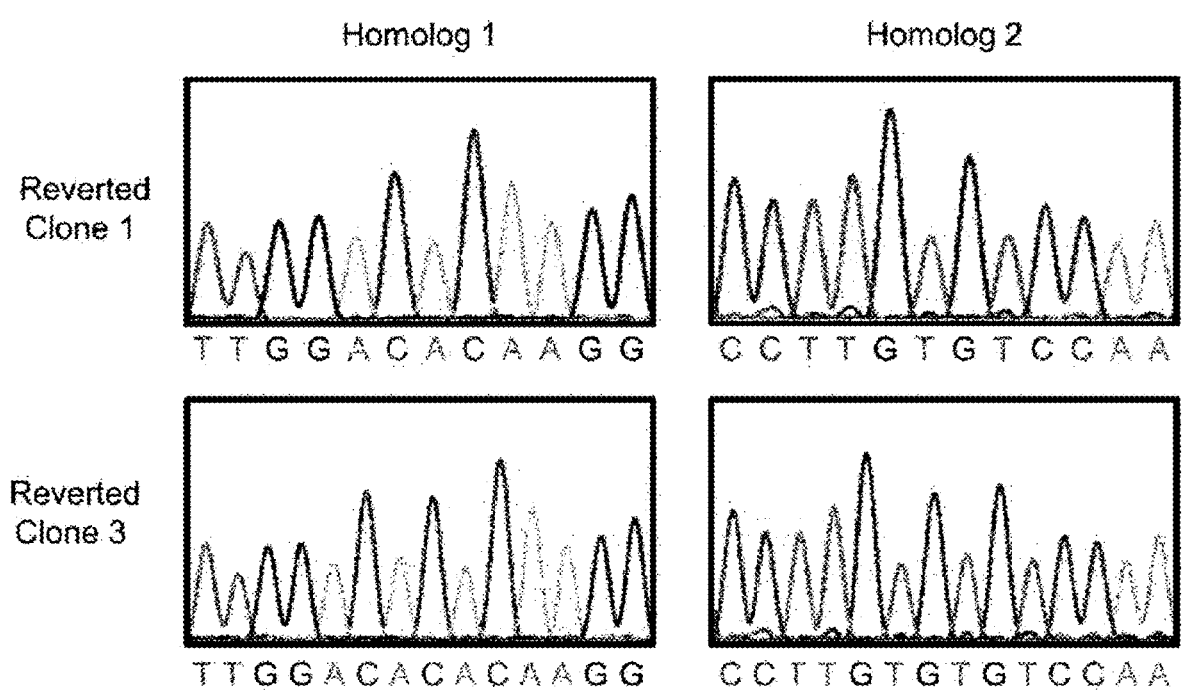

In this application, we investigated whether the inverted 140-kbp segment in the hemophilia model iPSC line could be corrected by reversion using the same TALEN pair. (Note that the TALEN site remains intact in the model cell line.) The TALEN plasmids were transfected into two iPSC clones containing the inversion (referred to here as "inversion clones"), and then genomic DNA samples isolated from several colonies were subjected to PCR to identify reverted cells. We obtained two reverted clones from each of the iPSC clones after screening a total of 300 colonies. Thus, the reversion frequency was 1.3% (4 of 300), on par with the inversion frequency. PCR analysis revealed that the genotype of these reverted clones was consistent with a reversion to wild type: No inversion-specific PCR bands were detected in the samples from these clones (FIG. 8a). We then cloned and sequenced these PCR products containing homolog 1 or 2. Two clones had no additional mutations, but the other two clones had 2-bp deletions at the two TALEN sites in both homologs 1 and 2 (FIG. 8b). These results show that the inversion genotype found in severe hemophilia A can be corrected by using the same TALEN pair that was used to generate the disease model.

Figure 14:
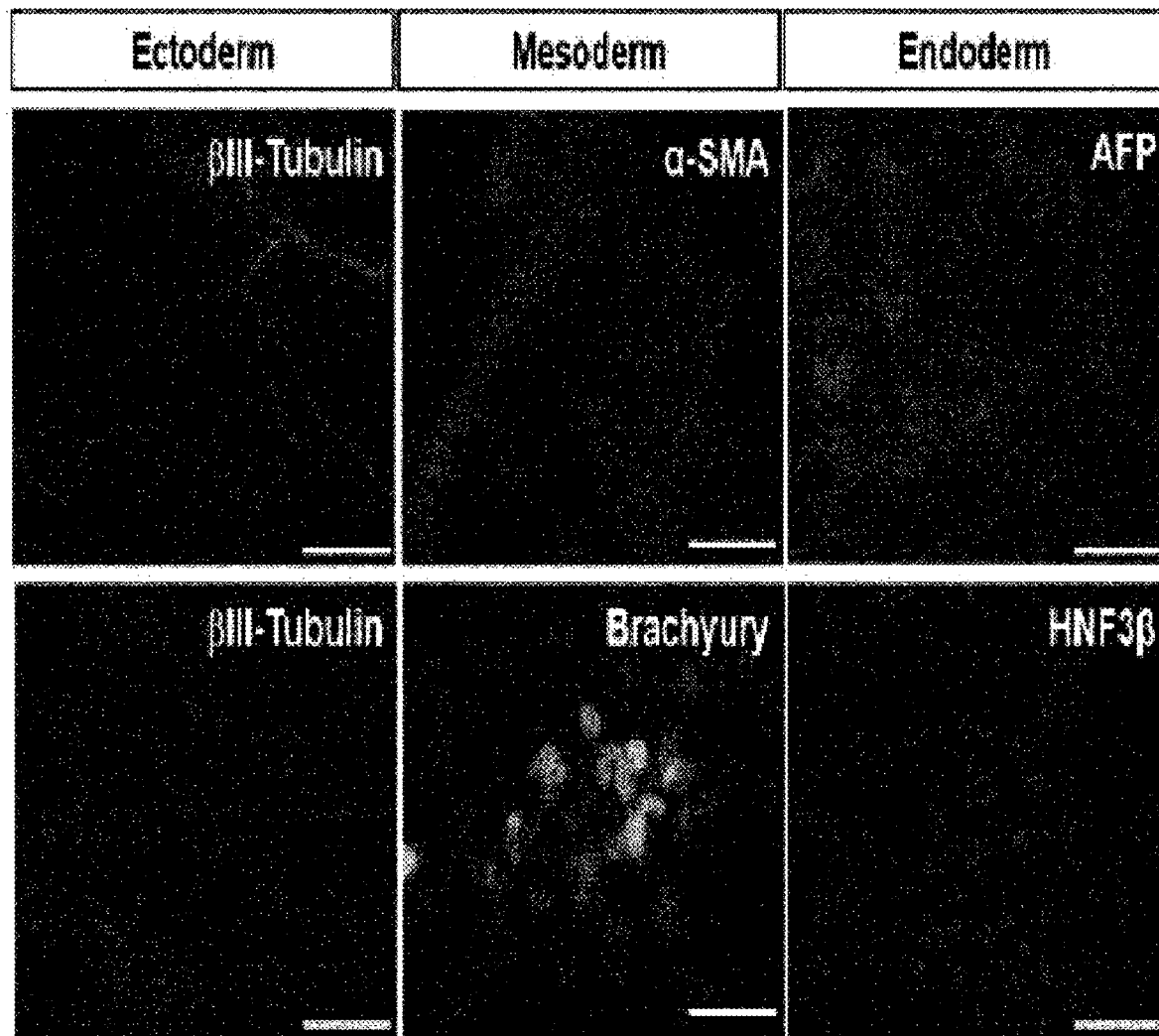
FIG. 14 shows in vitro differentiation of inverted and reverted clones. The expression of marker proteins representing ectoderm (βIII-Tubulin), mesoderm [α-smooth muscle actin (α-SMA) and Brachyury], and endoderm [α-fetoprotein (AFP) and HNF3β] in inversion clone 1 (Upper) and reverted clone 1 (Lower). (Scale bars, 50 μm.)

In addition, we investigated whether both the inversion clones and reverted clones remained pluripotent by checking their expression of human ES marker genes and their ability to undergo differentiation into the three primary germ layers. These clones expressed stem cell marker genes at levels comparable with those in wild-type iPSCs (FIG. 5f) and differentiated into three germ layers in vitro (FIG. 14). These results show that TALEN-mediated genome engineering does not negatively affect iPSC pluripotency.

Figure 9A:
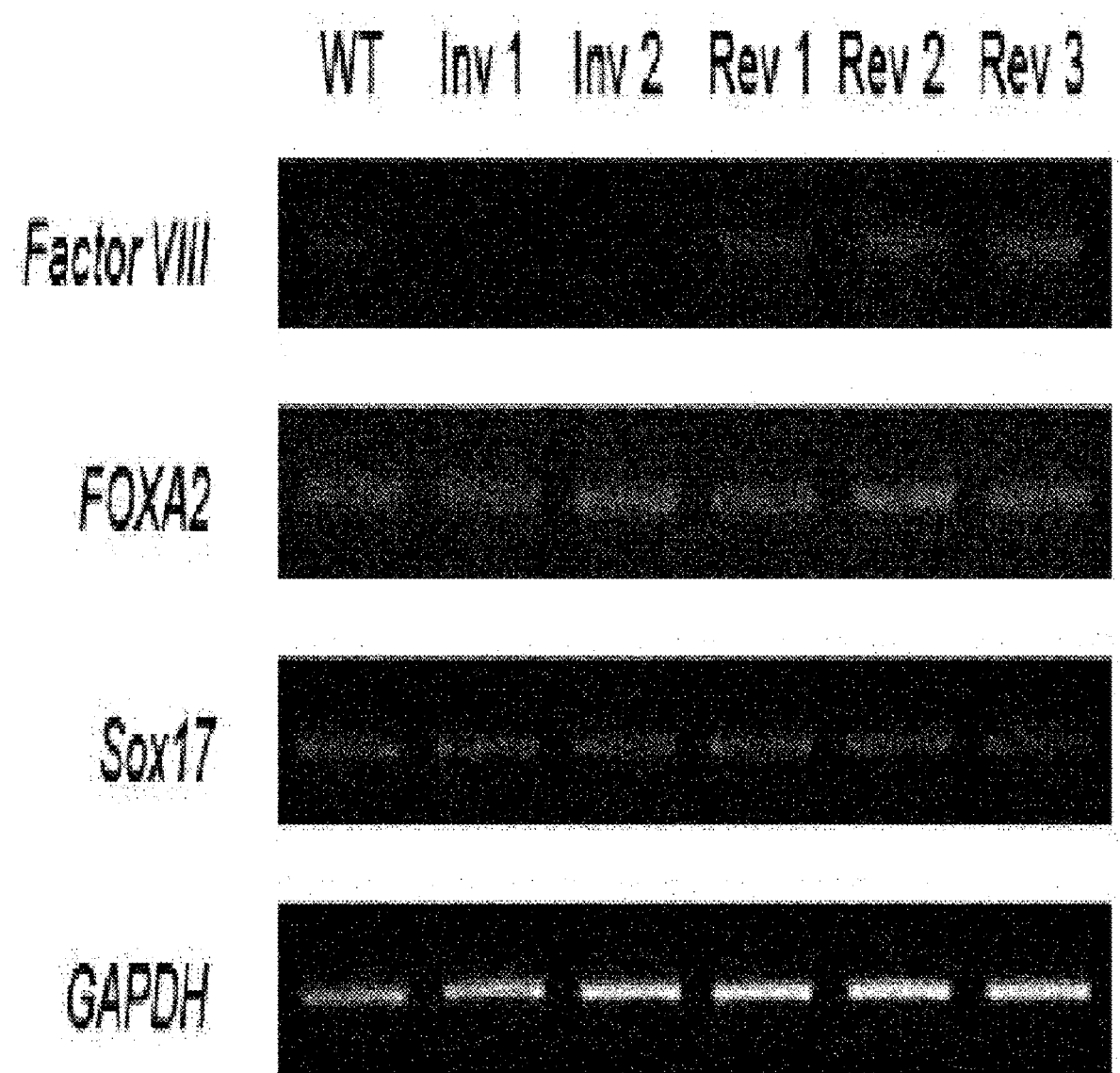
FIGS. 9a to 9b show characterization of inverted and reverted clones. (9a) F8 gene expression in cells derived from inverted and reverted clones. RT-PCR was used to detect expression of F8 and endoderm marker genes (FOXA2 and Sox17) in cells derived from wild-type iPSCs (WT), inversion clones (Inv 1 and 2), and reverted clones (Rev 1, 2, and 3). GAPDH served as a loading control. (9b) Expression of the F8 protein in endothelial cells differentiated from inverted and reverted clones. The differentiated cells were fixed and stained with the indicated antibodies. DAPI signals indicate the total cell presence in the image. FVIII, F8 protein; vWF, von Willebrand factor (a mature endothelial marker protein). (Scale bars, 100 μm.)
Figure 9B:
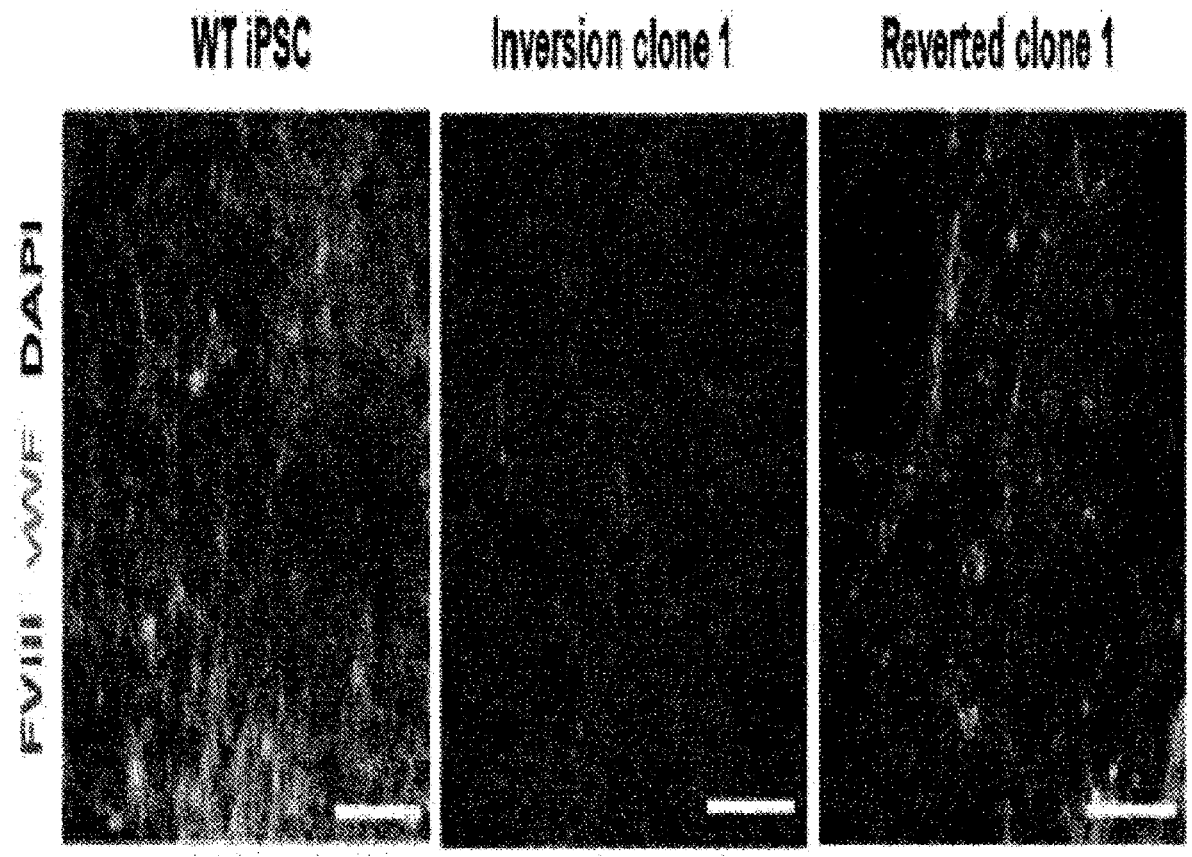

F8 Gene Expression in Cells Differentiated from Reverted iPSCs. The F8 gene is expressed in hepatocytes and endothelial cells (Zelechowska M G, van Mourik J A, Brodniewicz-Proba T (1985) Ultrastructural localization of factor VIII procoagulant antigen in human liver hepatocytes. Nature 317(6039):729-730; Hollestelle M J, et al. (2001) Tissue distribution of factor VIII gene expression in vivo; Shahani T, et al. (2010) Activation of human endothelial cells from specific vascular beds induces the release of a FVIII storage pool. Blood 115(23):4902-4909), which are derived from endoderm and mesoderm, respectively. First, we examined whether the F8 gene could be expressed in endodermal cells derived from the wild-type and reverted iPSC clones. We differentiated iPSCs into endoderm and performed an RT-PCR analysis to detect the F8 mRNA. As expected, the F8 mRNA was detected in cells differentiated from the wild-type and reverted iPSC clones (FIG. 9a). By contrast, no F8 mRNA was detected in cells derived from the iPSCs with the inversion, although these cells could differentiate into endoderm as efficiently as wild-type and reverted iPSCs. Next, we examined the expression of the F8 protein in endothelial cells, which are the main source of production of the F8 protein (Shahani T, et al. (2010) Activation of human endothelial cells from specific vascular beds induces the release of a FVIII storage pool. Blood 115(23):4902-4909). We differentiated iPSCs into endothelial cells and performed immunostaining to detect the F8 protein. As expected, the cells differentiated from wild-type and reverted iPSC clones expressed the F8 protein (FIG. 9b). However, the F8 protein was not detected in the cells differentiated from the inversion clone, although this iPSC clone differentiated successfully into endothelial cells as shown by the expression of von Willebrand factor, a mature endothelial cell marker protein. These results prove that the integrity of the F8 gene is restored in reverted iPSCs, which supports expression of the F8 gene in endodermal cells and mesoderm-derived endothelial cells.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A composition comprising a polypeptide comprising the following or a nucleotide sequence encoding the polypeptide:
   (a) a pair of endonucleases; and
   (b) a pair of transcription activator-like (TAL) effector domains, each of which is linked to each of the endonucleases and comprises an amino acid sequence specifically recognizing an inverted region of the F8 gene,
   wherein the pair of transcription activator-like (TAL) effector domains specifically bind to nucleotide sequences at first and second locations, wherein the nucleotide sequences at the first and second locations are the nucleotide sequences of SEQ ID NO:46 and SEQ ID NO:47, respectively.

2. The composition of claim 1, wherein the amino acid sequence specifically binding to the nucleotide sequence of SEQ ID NO:46 includes the amino acid sequence of SEQ ID NO:29.

3. The composition of claim 1, wherein the amino acid sequence specifically binding to the nucleotide sequence of SEQ ID NO:47 includes the amino acid sequence of SEQ ID NO:30.

4. The composition of claim 1, wherein the endonuclease is FokI endonuclease.

5. A method for correcting an inversion of the blood coagulation factor VIII (F8) gene, the method comprising:
   bringing somatic cells of a hemophilia A patient into contact with the composition of claim 1 or transfecting the somatic cells with a gene delivery system having the composition inserted thereinto.

6. A method for preparing induced pluripotent stem cells having an inversion-corrected blood coagulation factor VIII (F8) gene, the method comprising:
   (a) reprogramming somatic cells isolated from a hemophilia A patient to obtain induced pluripotent stem cells; and
   (b) bringing the induced pluripotent stem cells into contact with the composition of claim 1 or transfecting the induced pluripotent stem cells with a gene delivery system having the composition inserted thereinto.

7. The method of claim 6, wherein in step (a), the somatic cells isolated from the hemophilia A patient are transfected with at least one gene selected from the group consisting of OCT4, NANOG, SOX2, LIN28, KLF4, and c-MYC.

8. A method for treating hemophilia A, the method comprising:
   administering a composition comprising induced pluripotent stem cells as an active ingredient to a subject in need thereof, wherein the induced pluripotent stem cells are prepared by the method comprising:
(a) reprogramming somatic cells isolated from a hemophilia A patient to obtain induced pluripotent stem cells; and
(b) bringing the induced pluripotent stem cells into contact with the composition of claim 1 or transfecting the induced pluripotent stem cells with a gene delivery system having the composition inserted thereinto.

9. A composition comprising a polypeptide comprising the following or a nucleotide sequence encoding the polypeptide:
(a) a pair of endonucleases;
(b) a transcription activator-like (TAL) effector domain, which is linked to one of (a) and comprises an amino acid sequence specifically binding to a nucleotide sequence at a first location on the F8 gene; and
(c) a transcription activator-like (TAL) effector domain, which is linked to one of (a) and comprises an amino acid sequence specifically binding to a nucleotide sequence at a second location on the F8 gene, or a nucleotide sequence encoding the effector domain, wherein the nucleotide sequences at the first and second locations have the nucleotide sequences of SEQ ID NO:46 and SEQ ID NO:47, respectively.

10. The composition of claim 9, wherein an amino acid sequence specifically binding to the nucleotide sequence at the first location and an amino acid sequence specifically binding to the nucleotide sequence at the second location include the amino acid sequences of SEQ ID NO:29 and SEQ ID NO:30, respectively.

11. A method for inducing an inversion of the blood coagulation factor VIII (F8) gene, the method comprising:
introducing the composition of claim 9 into normal somatic cells.

* * * * *

UNITED STATES PATENT AND TRADEMARK OFFICE
CERTIFICATE OF CORRECTION

| | |
|---|---|
| PATENT NO. | : 11,197,935 B2 |
| APPLICATION NO. | : 15/807850 |
| DATED | : December 14, 2021 |
| INVENTOR(S) | : Dong Wook Kim et al. |

It is certified that error appears in the above-identified patent and that said Letters Patent is hereby corrected as shown below:

On the Title Page

Item (73) The 2nd Assignee is missing. Assignees should be listed as:
Industry Academic Cooperation Foundation of Yonsei University, Seoul (KR); and
INSTITUTE FOR BASIC SCIENCE, Daejeon (KR)

Signed and Sealed this
Thirteenth Day of December, 2022

Katherine Kelly Vidal
*Director of the United States Patent and Trademark Office*